United States Patent
Stewart et al.

(10) Patent No.: US 12,215,095 B2
(45) Date of Patent: Feb. 4, 2025

(54) COMPOUNDS FOR THE TREATMENT OF RESPIRATORY DISEASES

(71) Applicant: Tianli Biotech Pty Ltd, The University of Melbourne (AU)

(72) Inventors: Alastair Stewart, The University of Melbourne (AU); Spencer Williams, The University of Melbourne (AU); Zalihe Hakki, The University of Melbourne (AU)

(73) Assignee: The University of Melbourne, Melbourne (AU)

( * ) Notice: Subject to any disclaimer, the term of this patent is extended or adjusted under 35 U.S.C. 154(b) by 808 days.

(21) Appl. No.: 17/291,707

(22) PCT Filed: Nov. 7, 2019

(86) PCT No.: PCT/AU2019/051225
§ 371 (c)(1),
(2) Date: May 6, 2021

(87) PCT Pub. No.: WO2020/093098
PCT Pub. Date: May 14, 2020

(65) Prior Publication Data
US 2022/0002269 A1    Jan. 6, 2022

(30) Foreign Application Priority Data

Nov. 7, 2018 (AU) .............................. 2018904241
Nov. 7, 2018 (AU) .............................. 2018904242

(51) Int. Cl.
C07D 403/04    (2006.01)
A61P 11/00    (2006.01)
(Continued)

(52) U.S. Cl.
CPC ............ *C07D 403/04* (2013.01); *A61P 11/00* (2018.01); *C07D 403/14* (2013.01);
(Continued)

(58) Field of Classification Search
CPC .. C07D 403/04; C07D 403/14; C07D 405/14; A61P 11/06
See application file for complete search history.

(56) References Cited

U.S. PATENT DOCUMENTS 5,593,991 A    1/1997    Adams et al.
5,593,992 A    1/1997    Adams et al.
(Continued)

FOREIGN PATENT DOCUMENTS

CN    103784451 A    5/2014
EP    2589385 A1    5/2013
(Continued)

OTHER PUBLICATIONS

Kim et al. Bioorg. Med. Chem. Lett., 18 (2008), p. 2122. (Year: 2008).*
(Continued)

*Primary Examiner* — Matthew P Coughlin
*Assistant Examiner* — Ashli Ariana Chicks
(74) *Attorney, Agent, or Firm* — McCarter & English, LLP; Michael J. DeGrazia

(57) ABSTRACT

The present invention relates to new compounds that are useful in the prevention or treatment of respiratory diseases, such as asthma, acute and chronic inflammatory conditions, and fibrotic diseases or conditions in which fibrosis contributes to the pathology of the condition. The invention also relates to the preparation of the compounds, and to compositions including the compounds. The present invention also relates to the use of the compounds, as well as compositions including the compounds, in treating or preventing respira-
(Continued)

tory diseases, acute and chronic inflammatory conditions, and fibrotic diseases or conditions in which fibrosis contributes to the pathology of the condition.

20 Claims, 18 Drawing Sheets

(51) Int. Cl.
   *C07D 403/14* (2006.01)
   *C07D 405/14* (2006.01)
   *C07D 409/14* (2006.01)

(52) U.S. Cl.
   CPC ......... *C07D 405/14* (2013.01); *C07D 409/14* (2013.01); *C07B 2200/05* (2013.01)

(56) References Cited

U.S. PATENT DOCUMENTS

| | | | |
|---|---|---|---|
| 5,670,527 | A | 9/1997 | Adams et al. |
| 5,827,699 | A | 10/1998 | Yanenko et al. |
| 6,057,307 | A | 5/2000 | Sequeira et al. |
| 6,218,537 | B1 | 4/2001 | Adams et al. |
| 6,369,068 | B1 | 4/2002 | Adams et al. |
| 6,598,603 | B1 | 7/2003 | Andersson et al. |
| 6,730,683 | B2 * | 5/2004 | Gallagher ............ A61P 31/12 544/122 |
| 8,518,944 | B2 | 8/2013 | Subramanyam et al. |
| 2004/0209805 | A1 | 10/2004 | Phillips et al. |
| 2008/0188443 | A1 | 8/2008 | Cheng et al. |
| 2009/0099237 | A1 | 4/2009 | Aud et al. |
| 2011/0098272 | A1 | 4/2011 | Subramanyam et al. |
| 2011/0166153 | A1 | 7/2011 | Watterson et al. |
| 2012/0184557 | A1 | 7/2012 | Meijer et al. |
| 2013/0115309 | A1 | 5/2013 | Grandori et al. |
| 2019/0175596 | A1 | 6/2019 | de Maeyer et al. |
| 2020/0079757 | A1 | 3/2020 | Williams et al. |
| 2022/0281846 | A1 | 9/2022 | Stewart et al. |
| 2022/0380343 | A1 | 12/2022 | Williams et al. |

FOREIGN PATENT DOCUMENTS

| | | | | |
|---|---|---|---|---|
| JP | 2016-193861 | A | 11/2016 | |
| WO | 1995/02591 | A1 | 1/1995 | |
| WO | 1996/021654 | A1 | 7/1996 | |
| WO | 1996/040143 | A1 | 12/1996 | |
| WO | 1997/035586 | A1 | 10/1997 | |
| WO | 1997/035856 | A1 | 10/1997 | |
| WO | 1999/001136 | A1 | 1/1999 | |
| WO | 1999/18942 | A1 | 4/1999 | |
| WO | 1999/032121 | A1 | 7/1999 | |
| WO | 2004/028545 | A1 | 4/2004 | |
| WO | 2005/074918 | A1 | 8/2005 | |
| WO | 2005/103240 | A1 | 11/2005 | |
| WO | 2008/071605 | A2 | 6/2008 | |
| WO | 2010/043981 | A1 | 4/2010 | |
| WO | 2011/127202 | A2 | 10/2011 | |
| WO | 2012/080727 | A2 | 6/2012 | |
| WO | 2014/018691 | A1 | 1/2014 | |
| WO | 2014/023271 | A1 | 2/2014 | |
| WO | 2014/054526 | A1 | 4/2014 | |
| WO | 2014/100533 | A1 | 6/2014 | |
| WO | 2014/100540 | A1 | 6/2014 | |
| WO | 2015/114638 | A2 | 8/2015 | |
| WO | 2016/149756 | A1 | 9/2016 | |
| WO | 2017/083971 | A1 | 5/2017 | |
| WO | 2018/081575 | A1 | 5/2018 | |
| WO | WO-2018201192 | A1 * | 11/2018 | ............ A61P 11/06 |
| WO | 2020/049190 | A1 | 3/2020 | |
| WO | 2020/093097 | A1 | 5/2020 | |
| WO | 2020/093098 | A1 | 5/2020 | |

OTHER PUBLICATIONS

U.S. Appl. No. 16/610,168, filed Nov. 1, 2019, 2020-0079757, Abandoned.
U.S. Appl. No. 17/690,855, filed Mar. 9, 2022, Pending.
U.S. Appl. No. 17/291,694, filed May 5, 2021, Pending.
Badura et al., An inhibitor of casein kinase I epsilon induces phase delays in circadian rhythms under free-running and entrained conditions. J Pharmacol Exp Ther. Aug. 2007;322(2):730-8.
Barnes et al., How do corticosteroids work in asthma? Ann Intern Med. Sep. 2, 2003;139(5 Pt 1):359-70.
Barnes, Inhaled Corticosteroids. Pharmaceuticals (Basel). Mar. 8, 2010;3(3):514-540.
Bell et al., The future of cystic fibrosis care: a global perspective. Lancet Respir Med. Jan. 2020;8(1):65-124.
Boucher, Muco-Obstructive Lung Diseases. N Engl J Med. May 16, 2019;380(20):1941-1953.
Buckingham et al., A randomized, double-blind, placebo-controlled trial of dexamethasone in severe respiratory syncytial virus (RSV) infection: effects on RSV quantity and clinical outcome. J Infect Dis. May 1, 2002;185(9):1222-8.
Littlewood, History of cystic fibrosis. Hodson and Geddes' Cystic Fibrosis, Andrew Bush (Ed.), 3rd ed. CRC Press, Boca Raton, Florida. pp. 3-19, (2007).
Marchant et al., Toll-like receptor 4-mediated activation of p38 mitogen-activated protein kinase is a determinant of respiratory virus entry and tropism. J Virol. Nov. 2010;84(21):11359-73.
Mccarron et al., Airway disease phenotypes in animal models of cystic fibrosis. Respir Res. Apr. 2, 2018;19(1):54, 12 pages.
PubChem CID 9959143, N-[4-[3-Cyclohexyl-5-(4-fluorophenyl)imidazol-4-yl]pyrimidin-2-yl]-N',N'-diphenylpropane-1,3-diamine. 6 pages, Oct. 31, 2020.
Sheppard et al., Structure and function of the CFTR chloride channel. Physiol Rev. Jan. 1999;79(1 Suppl):S23-45.
Sur et al., Treatment of allergic rhinitis. Am Fam Physician. Jun. 15, 2010;81(12):1440-6.
Vogt et al., The specificities of small molecule inhibitors of the TGFß and BMP pathways. Cell Signal. Nov. 2011;23(11):1831-42.
Walton et al., Selective inhibition of casein kinase 1 epsilon minimally alters circadian clock period. J Pharmacol Exp Ther. Aug. 2009;330(2):430-9.
Wuyts et al., Combination therapy: the future of management for idiopathic pulmonary fibrosis? Lancet Respir Med. Nov. 2014;2(11):933-942.
Yamaya et al., Virus infection-induced bronchial asthma exacerbation. Pulm Med. 2012;2012:834826, 14 pages.
Ziobro et al., Ceramide mediates lung fibrosis in cystic fibrosis. Biochem Biophys Res Commun. May 17, 2013;434(4):705-9.
Copending U.S. Appl. No. 17/690,855, filed Mar. 9, 2022.
Copending U.S. Appl. No. 17/291,694, filed May 5, 2021.
CAS Registry No. 1349012-04-9, STN Entry Date: Dec. 5, 2011; 2-Pyrimidinamine, N-(3-[1, 1'-biphenyl]-3-ylpropyl)-4-[1-cyclohexyl-4-(4-fluorophenyl)-1H-imidazol-5-yl]-.
Keenan et al. Casein kinase Igamma/epsilon inhibitor, PF670462 attenuates the fibrogenic effects of transforming growth factor-beta pulmonary fibrosis. Front Pharmacol. 9(738): 15 pages (2018).
Kim, et al. Synthesis and biological evaluation of trisubstituted imidazole derivatives as inhibitors of p38alpha mitogen-activated protein kinase. Bioorganic & Medicinal Chemistry Letters. 18: 4006-4010 (2008).
Li et al., In silico prediction of spleen tyrosine kinase inhibitors using machine learning approaches and an optimized molecular descriptor subset generated by recursive feature elimination method. Comput Biol Med. May 2013;43(4):395-404.
Pinsetta et al., Rational Design of Novel Potential p38a MAPK Inhibitors with Drug-like Properties Using Pharmacophore and Similarity-based Virtual Screening Procedures. Current Bioactive Compounds. 2013;9:3-13.
Rudolph et al., Slow inhibition and conformation selective properties of extracellular signal-regulated kinase 1 and 2 inhibitors. Biochemistry. Jan. 13, 2015;54(1):22-31.
Vinh et al., Virtual screening using a conformationally flexible target protein: models for ligand binding to p38a MAPK. J Comput Aided Mol Des. Apr. 2012;26(4):409-23.

(56) References Cited

OTHER PUBLICATIONS

Wager et al., Casein kinase 1gamma/e inhibitor PF-5006739 attenuates opioid drug-seeking behavior. ACS Chem Neurosci. Dec. 17, 2014;5(12):1253-65.

* cited by examiner

COMPOUNDS FOR THE TREATMENT OF RESPIRATORY DISEASES

RELATED APPLICATIONS

This application is a 35 U.S.C. § 371 national stage filing of International Application No. PCT/AU2019/051225, filed on Nov. 7, 2019, which claims priority to AU2018904241 and AU2018904242, filed on Nov. 7, 2018. The entire contents of each of the aforementioned applications are incorporated herein by reference.

This application claims priority to AU2018904241 and AU2018904242 (each filed on 7 Nov. 2018). The entire contents of each of AU2018904241 and AU2018904242 is incorporated herein by reference.

FIELD OF THE INVENTION

The present invention provides imidazole-based compounds that show potential in the treatment of respiratory diseases, such as asthma and related conditions, acute and chronic inflammatory conditions, and fibrotic diseases or conditions in which fibrosis contributes to the pathology of the condition.

BACKGROUND OF THE INVENTION

Asthma is a syndrome that encompasses various different types of diseases, which vary in their severity and in their causes and triggers. The common features of the asthma syndrome are reversible airway obstruction, airway hyper-responsiveness and airway inflammation, with infiltration of the airway wall by eosinophils and T lymphocytes the most prominent features in addition to activation of mast cells.

Current asthma medications include short- and long-acting $\beta_2$-adrenoceptor selective agonists (SABA and LABA) and inhaled corticosteroids (ICS). Ultra-LABA are now also available. Short and long-acting muscarinic receptor antagonists (SAMA and LAMA) are used in some patients, usually in combination with other bronchodilators and anti-inflammatory drugs, especially ICS. Leukotriene receptor antagonists (LTRA) may also be added to different therapeutic regimens. More recently, the monoclonal antibody mepolizumab, which neutralises a chemoattractant for eosinophils, interleukin-5, has been shown to have benefit additional to the ICS and LABA combinations in selected patients. Nevertheless, for severe asthma in particular, patients are still symptomatic and have periodic worsening of disease, referred to as exacerbations. There is a considerable unmet need in the drug treatment of severe asthma. In the majority of cases these asthma exacerbations are considered to be caused by respiratory viral infection of the lower respiratory tract. The viruses that cause these exacerbations include respiratory syncytial virus, influenza virus and rhinoviruses, which infect the respiratory epithelium. The epithelium of asthmatic individuals is considered to be especially susceptible to such infections and is implicated in the worsening of the inflammatory response.

Research has shown that TGF-$\beta$ is able to compromise the effectiveness of ICS. Furthermore, the inventors have demonstrated that viral infection of the airway epithelium compromises ICS activity through induction of TGF-$\beta$ activity. Drug targeting of TGF-$\beta$ carries risk of autoimmune and mitral valve defects. The inventors surprisingly identified casein kinase 1δ/ε as a mediator of TGF-$\beta$ induced ICS insensitivity, using the compound PF670462 (WO2016/149756), and demonstrated the utility of this agent to reverse steroid insensitivity.

It would be useful to develop alternative compounds that may be useful for preventing or treating one or more respiratory diseases, acute and chronic inflammatory conditions, and fibrotic diseases or conditions in which fibrosis contributes to the pathology of the condition.

SUMMARY OF THE INVENTION

Described herein is a compound of formula (II) or a salt, solvate, N-oxide, tautomer, stereoisomer, polymorph and/or prodrug thereof:

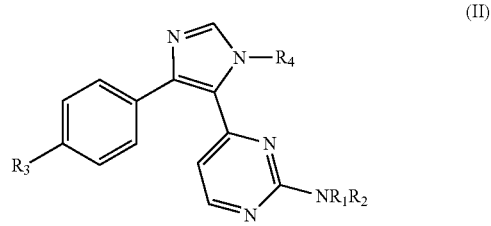

(II)

wherein:

$R_1$ and $R_2$ are each independently selected from the group consisting of H, $C_{1-3}$alkyl$C_{6-12}$aryl, $C_{1-3}$alkyl$C_{5-11}$heteroaryl, $C_{1-3}$alkyl$C_{3-6}$cycloalkyl and $C_{1-3}$alkyl$C_{3-6}$heterocyclyl;

$R_3$ is selected from the group consisting of H, F, Cl and $CH_3$;

$R_4$ is selected from the group consisting of $C_{0-3}$alkyl$C_{3-12}$cycloalkyl and $C_{1-12}$alkyl;

wherein each of $R_1$, $R_2$, $R_3$ and $R_4$ is optionally substituted.

In some embodiments, the compound of formula (II) is a compound of formula (I)

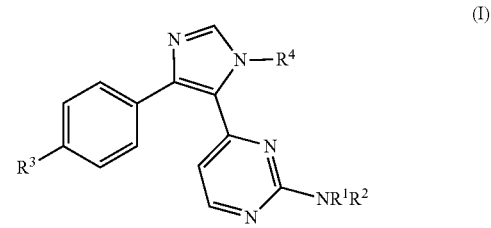

(I)

wherein:

$R^1$ is selected from the group consisting of $C_{2-3}$alkyl$C_{6-12}$aryl, $C_1$alkyl$C_{10-12}$aryl, $C_{1-3}$alkyl$C_{5-11}$heteroaryl, $C_{1-3}$alkyl$C_{3-6}$cycloalkyl and $C_{1-3}$alkyl$C_{3-6}$heterocyclyl;

$R^2$ is H;

$R^3$ is selected from the group consisting of H, F, Cl and $CH_3$;

$R^4$ is selected from the group consisting of $C_{0-3}$alkyl$C_{3-12}$cycloalkyl and $C_{1-12}$alkyl;

wherein each of $R^1$, $R^2$, $R^3$ and $R^4$ is optionally substituted, with the proviso that the compound is not selected from:
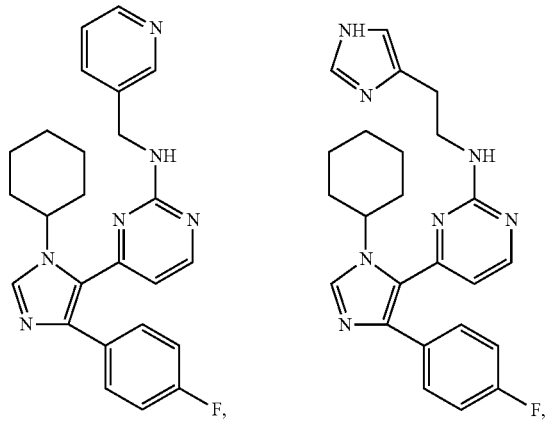
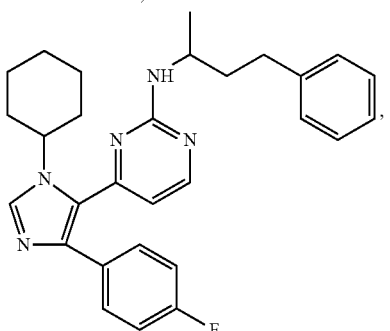
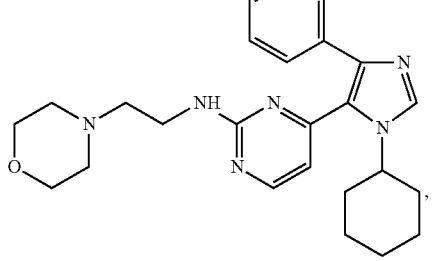
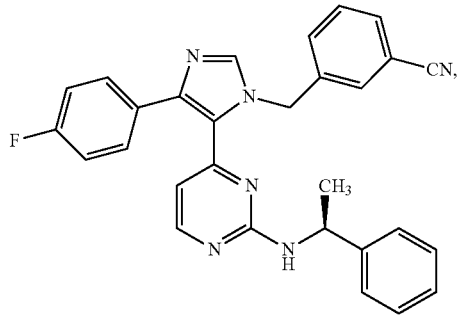
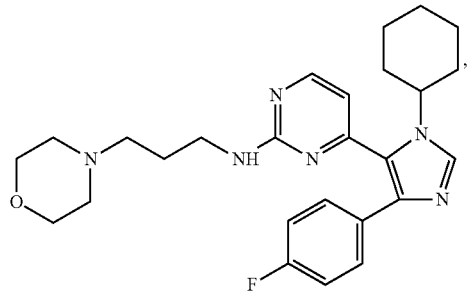
-continued
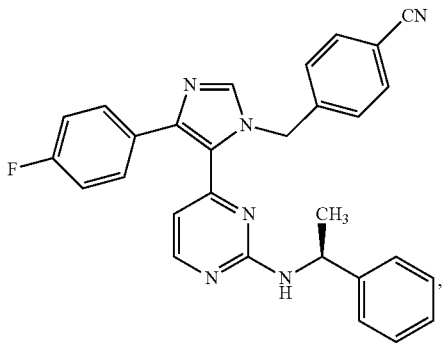
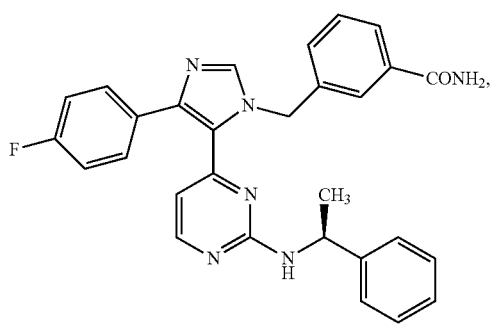
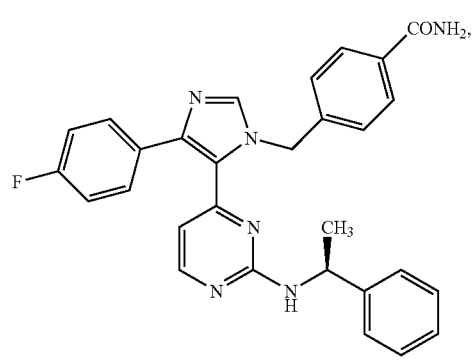

-continued

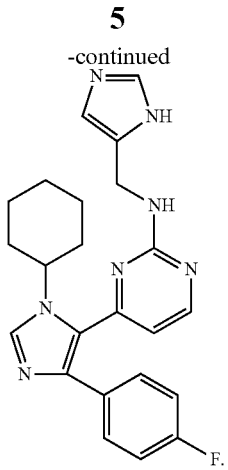

In another aspect, there is provided a method of treating or preventing a respiratory disease in a subject in need thereof, the method comprising administering to the subject a therapeutically effective amount of a compound of formula (I) or (II) or a salt, solvate, N-oxide, tautomer, stereoisomer, polymorph and/or prodrug thereof, thereby treating or preventing a respiratory disease in a subject.

There is further provided a compound of formula (I) or (II), or a salt, solvate, N-oxide, tautomer, stereoisomer, polymorph and/or prodrug thereof for use in the treatment or prevention of a respiratory disease in a subject.

The respiratory disease may be selected from asthma, chronic obstructive pulmonary disease, interstitial lung diseases (such as idiopathic pulmonary fibrosis) and other conditions relating to tissue remodelling, primary or secondary lung tumour, hayfever, chronic and acute sinusitis, and chronic and acute viral, fungal and bacterial infections of the respiratory tract.

In another aspect, there is provided a method of improving respiratory function in a subject in need thereof, the method comprising administering to the subject a therapeutically effective amount of a compound of formula (I) or (II), or a salt, solvate, N-oxide, tautomer, stereoisomer, polymorph and/or prodrug thereof, thereby improving respiratory function of the subject.

There is further provided a compound of formula (I) or (II) or a salt, solvate, N-oxide, tautomer, stereoisomer, polymorph and/or prodrug thereof for use in improving respiratory function in a subject.

The improvement in respiratory function may be selected from a decrease in the level of constriction of the lungs, a decrease in the elastic stiffness of the respiratory system, and/or an increase in the ease with which the respiratory system can be extended. Preferably, the improvement is selected from a decrease in the level of constriction of the lungs, and a decrease in the elastic stiffness of the respiratory system. In yet another aspect, there is provided a composition comprising a compound according to formula (I) or (II), or a salt, solvate, N-oxide, tautomer, stereoisomer, polymorph and/or prodrug thereof, and a pharmaceutically acceptable excipient.

The composition may be formulated for oral administration or administration by inhalation or injection.

Use of a compound or composition of the invention in the preparation of medicaments for the treatment or prevention of a respiratory disease in a subject is also described.

As used herein, except where the context requires otherwise, the term "comprise" and variations of the term, such as "comprising", "comprises" and "comprised", are not intended to exclude further additives, components, integers or steps.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

Further aspects of the present invention and further embodiments of the aspects described in the preceding paragraphs will become apparent from the following description, given by way of example and with reference to the accompanying drawings.

DETAILED DESCRIPTION

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

Described herein is a compound of formula (II) or a salt, solvate, N-oxide, tautomer, stereoisomer, polymorph and/or prodrug thereof:

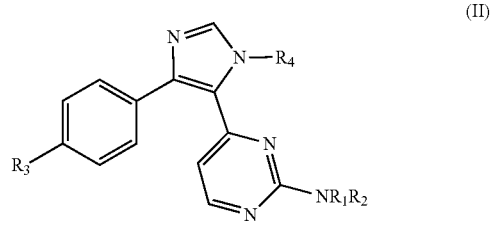

(II)

wherein:
R₁ and R₂ are each independently selected from the group consisting of H, $C_{1-3}$alkyl$C_{6-12}$aryl, $C_{1-3}$alkyl$C_{5-11}$heteroaryl, $C_{1-3}$alkyl$C_{3-6}$cycloalkyl and $C_{1-3}$alkyl$C_{3-6}$heterocyclyl;

R₃ is selected from the group consisting of H, F, Cl and CH₃;

R₄ is selected from the group consisting of $C_{0-3}$ alkyl$C_{3-12}$ cycloalkyl and $C_{1-12}$alkyl;

wherein each of R₁, R₂, R₃ and R₄ is optionally substituted.

In some embodiments, the compound of formula (II) is provided by a compound of formula (I)

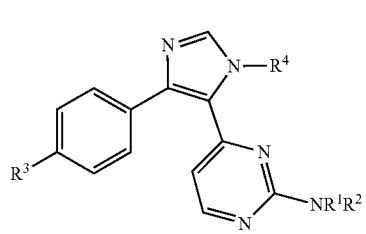

(I)

wherein:
R¹ is selected from the group consisting of $C_{2-3}$ alkyl$C_{6-12}$ aryl, $C_{1-3}$ alkyl$C_{5-11}$heteroaryl, $C_{1-3}$ alkyl$C_{3-6}$ cycloalkyl and $C_{1-3}$ alkyl$C_{3-6}$ heterocyclyl;

R² is H;

R³ is selected from the group consisting of H, F, Cl and CH₃;

R⁴ is selected from the group consisting of $C_{0-3}$ alkyl$C_{3-12}$ cycloalkyl and $C_{1-12}$ alkyl;

wherein each of R¹, R², R³ and R⁴ is optionally substituted, with the proviso that the compound is not selected from:

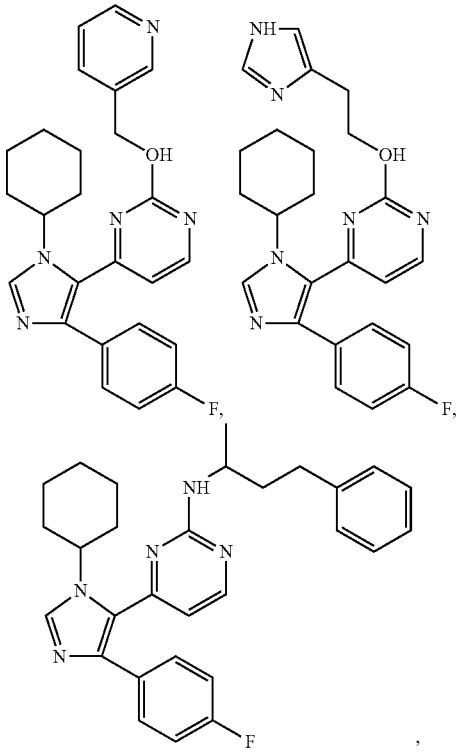

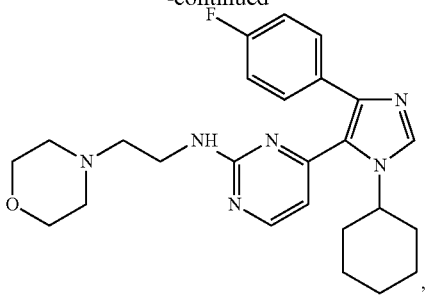

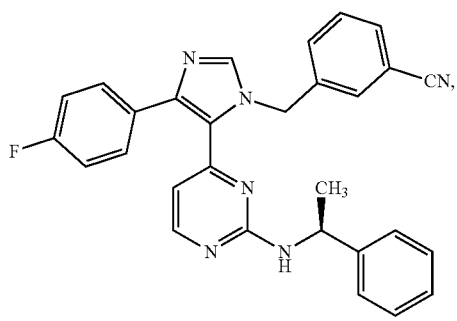

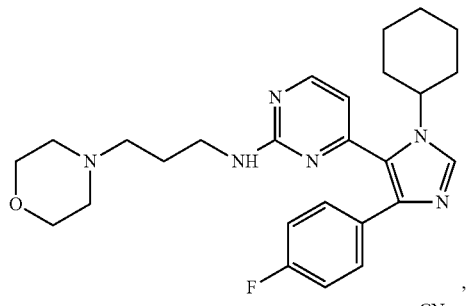

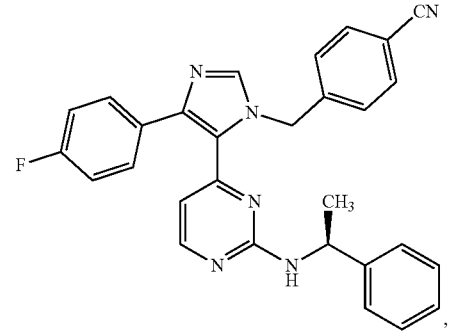

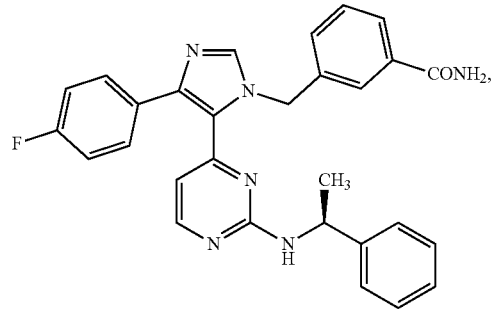

-continued

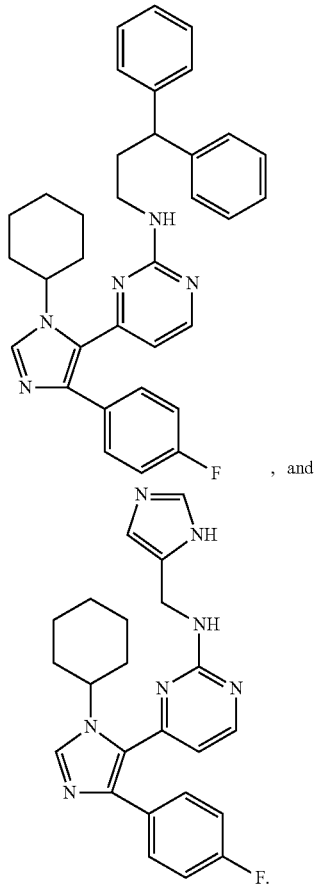

Figure 1:
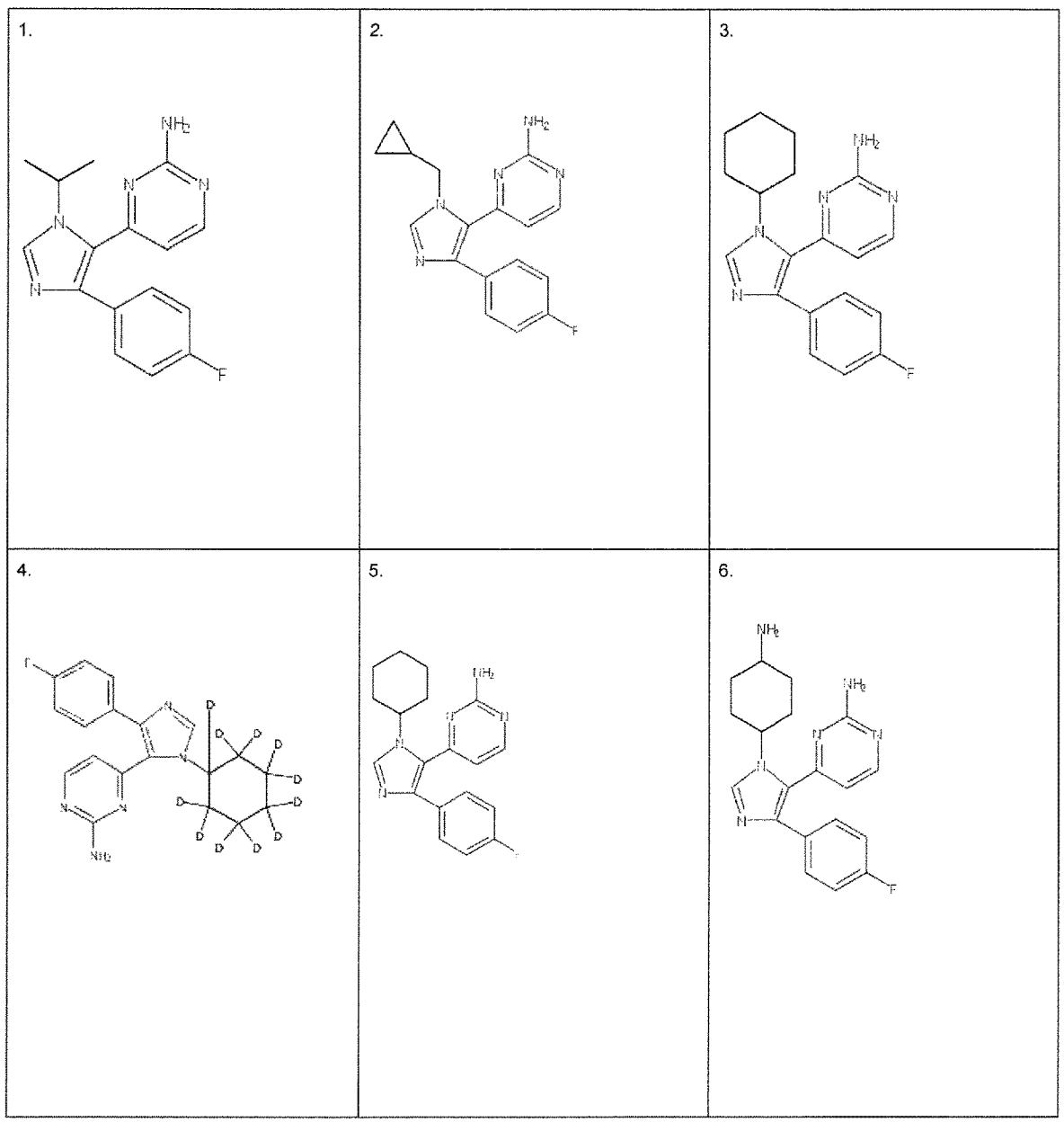
FIG. 1. Defines a number of known compounds.
Figure 1:
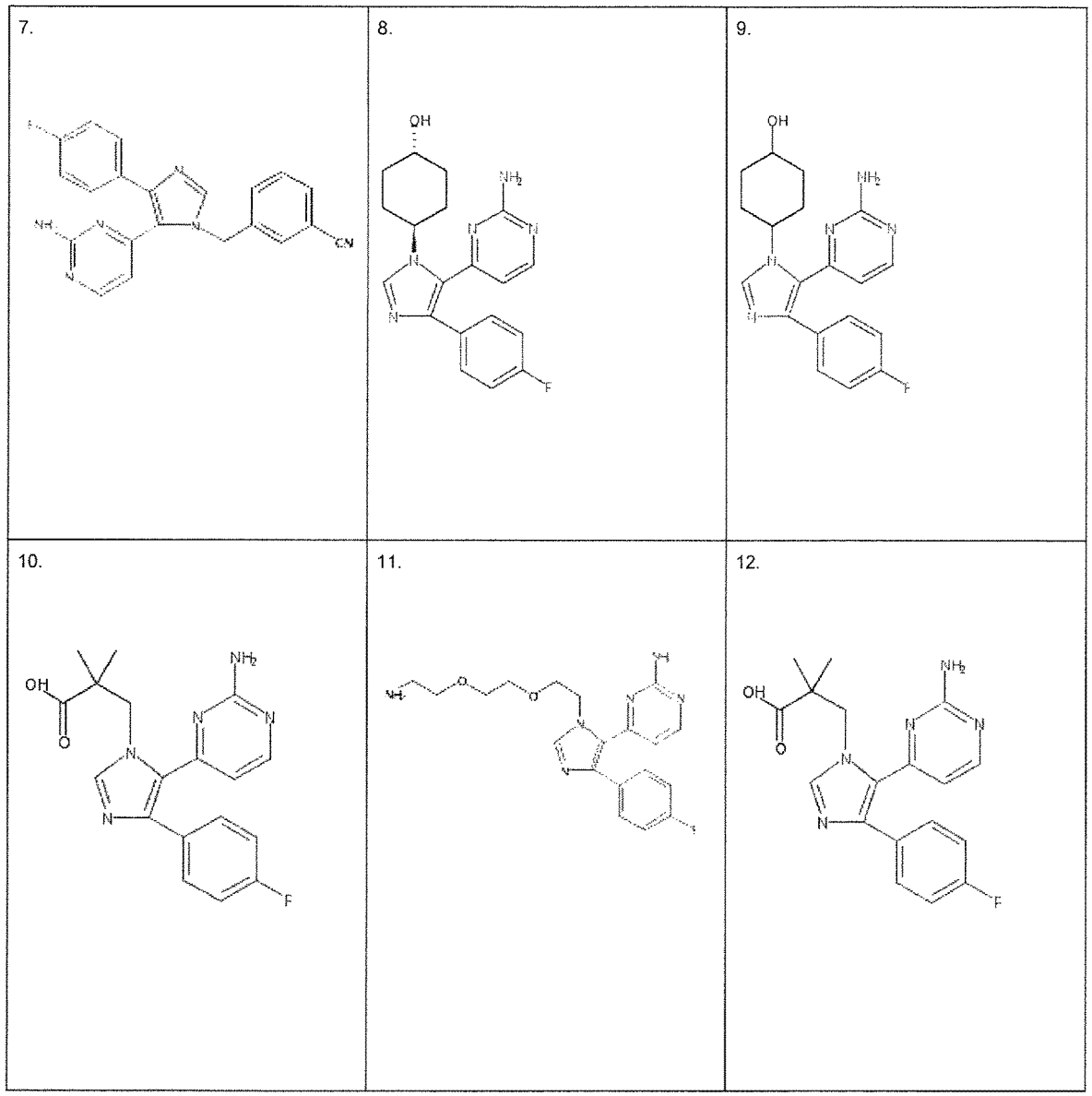
Figure 1:
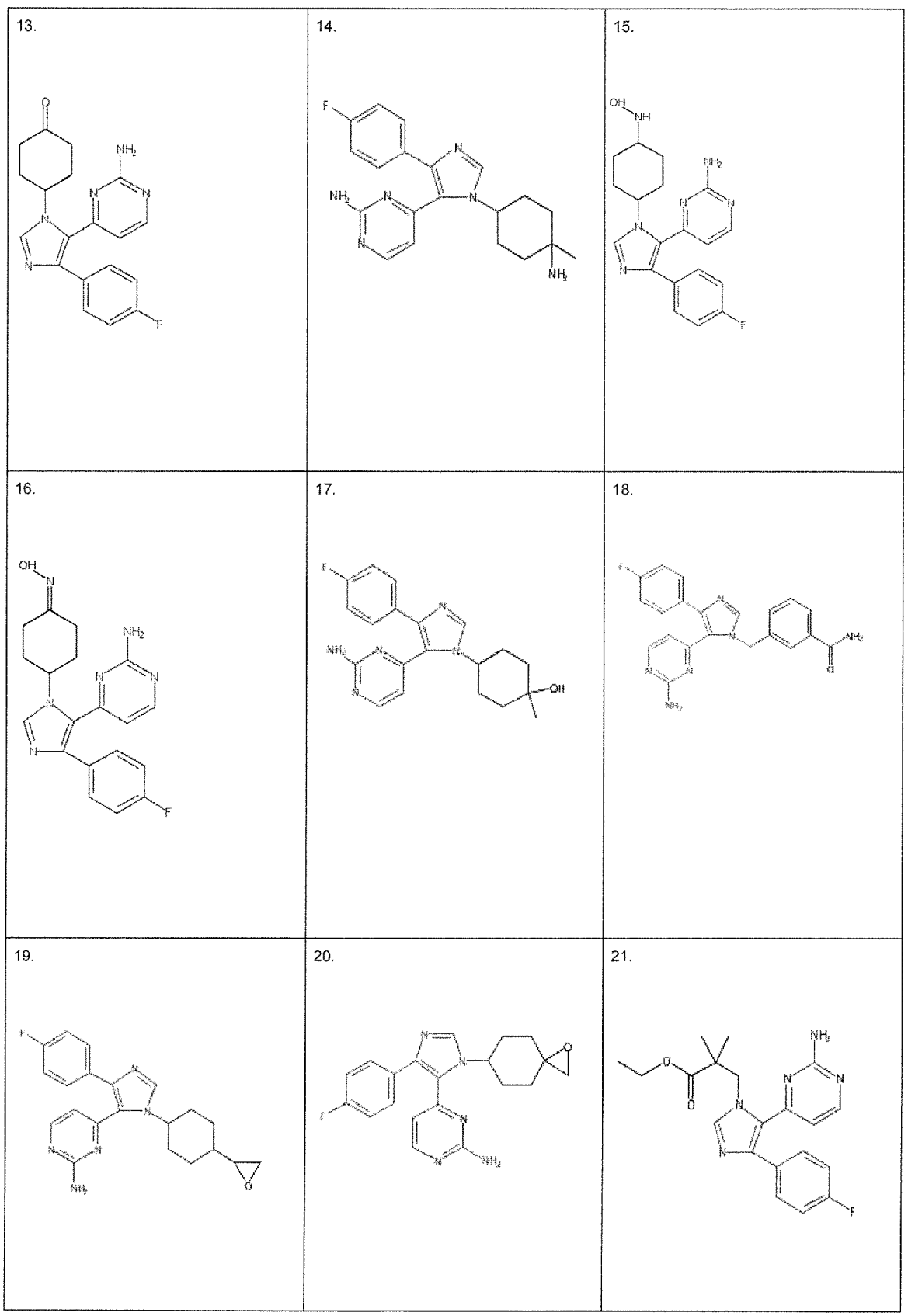
Figure 1:
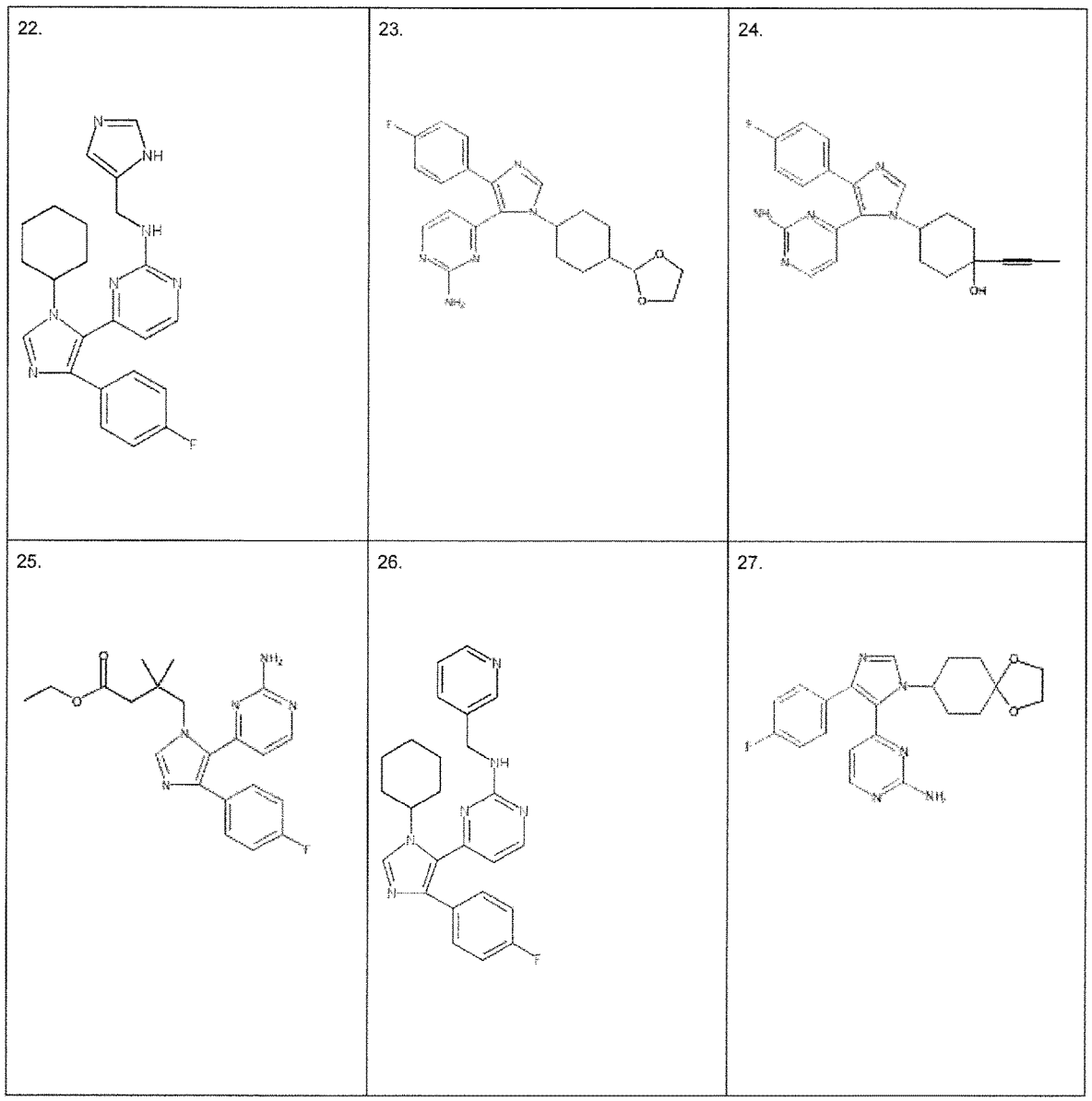
Figure 1:
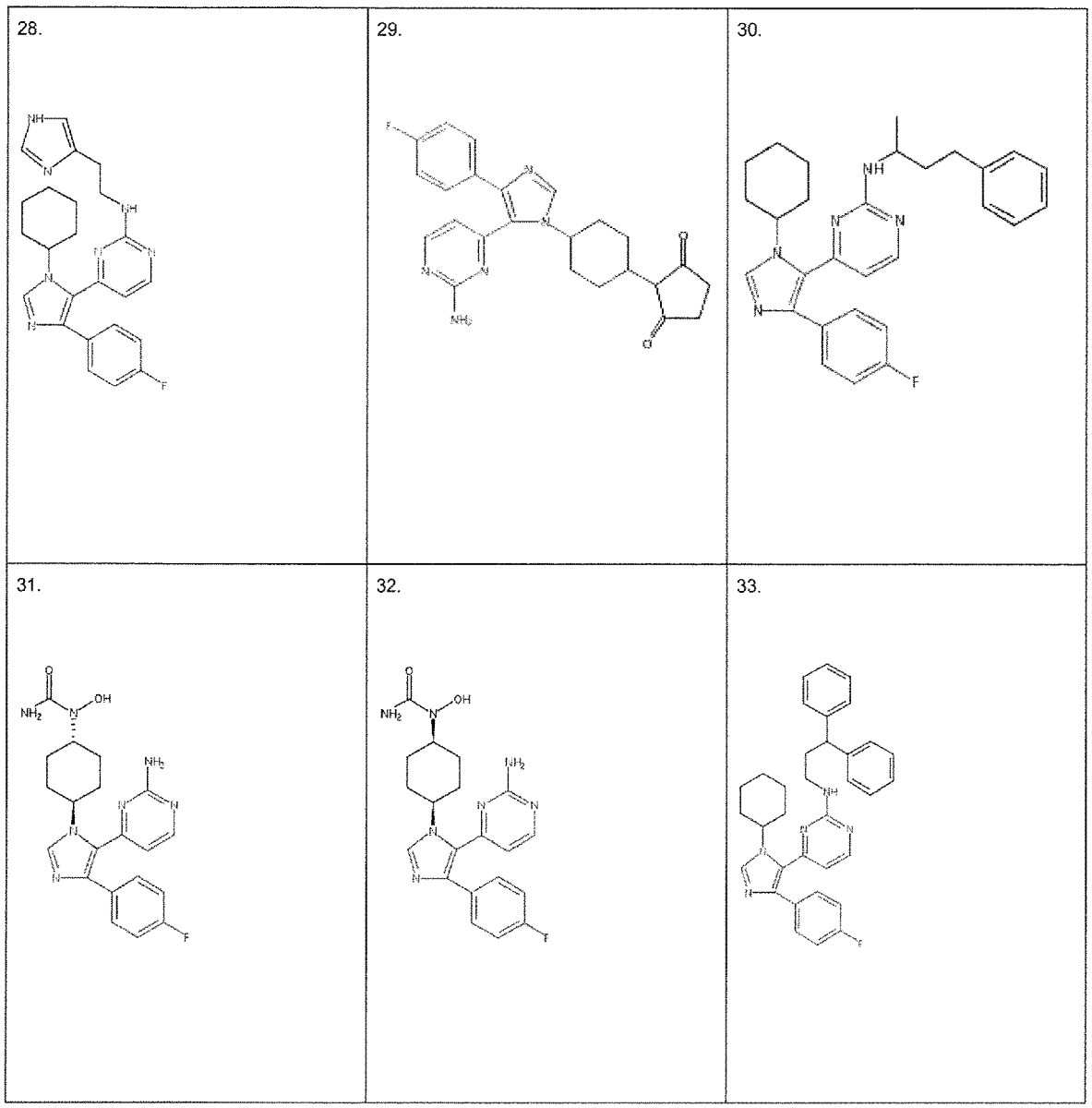
Figure 1:
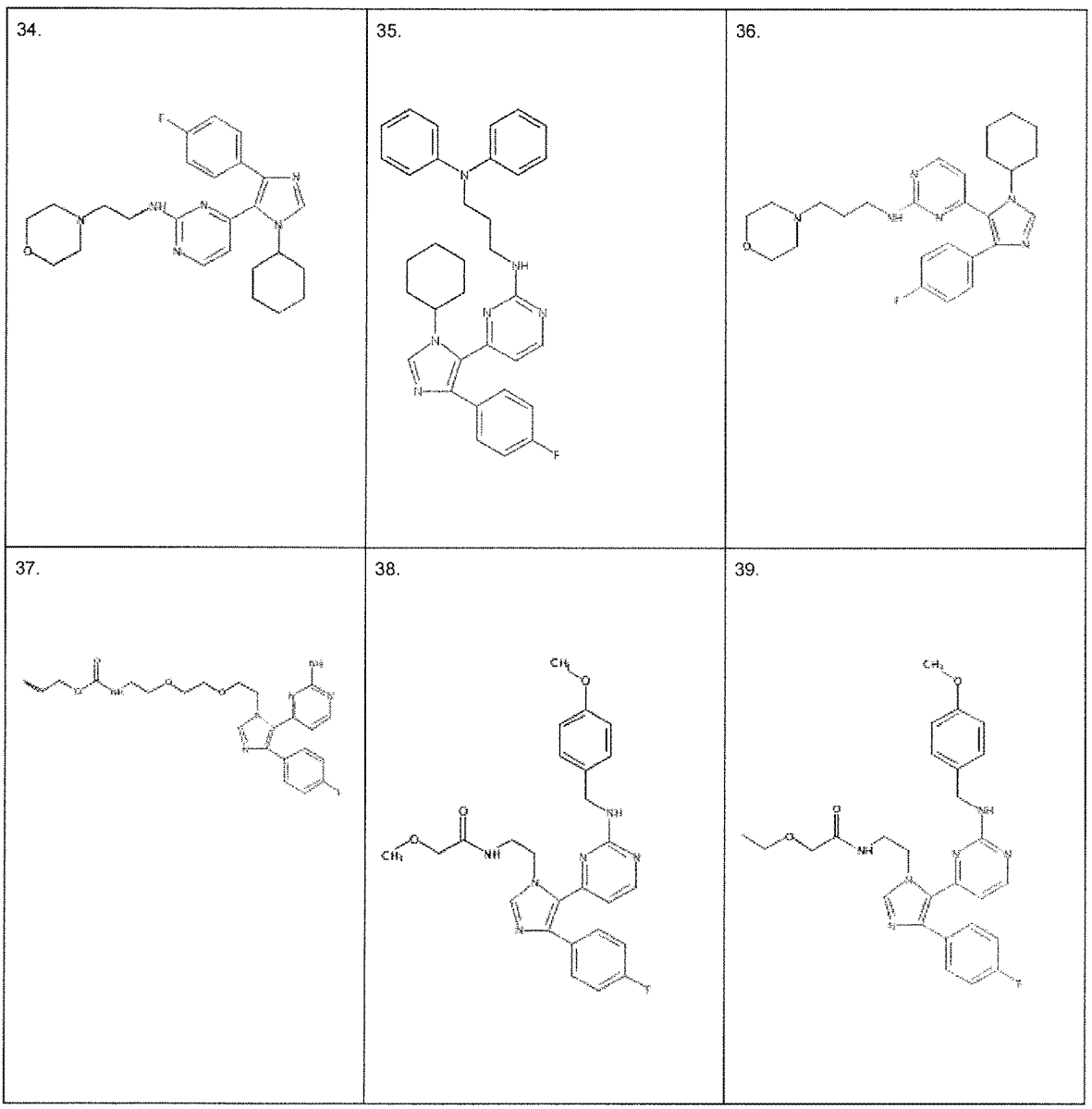
Figure 1:
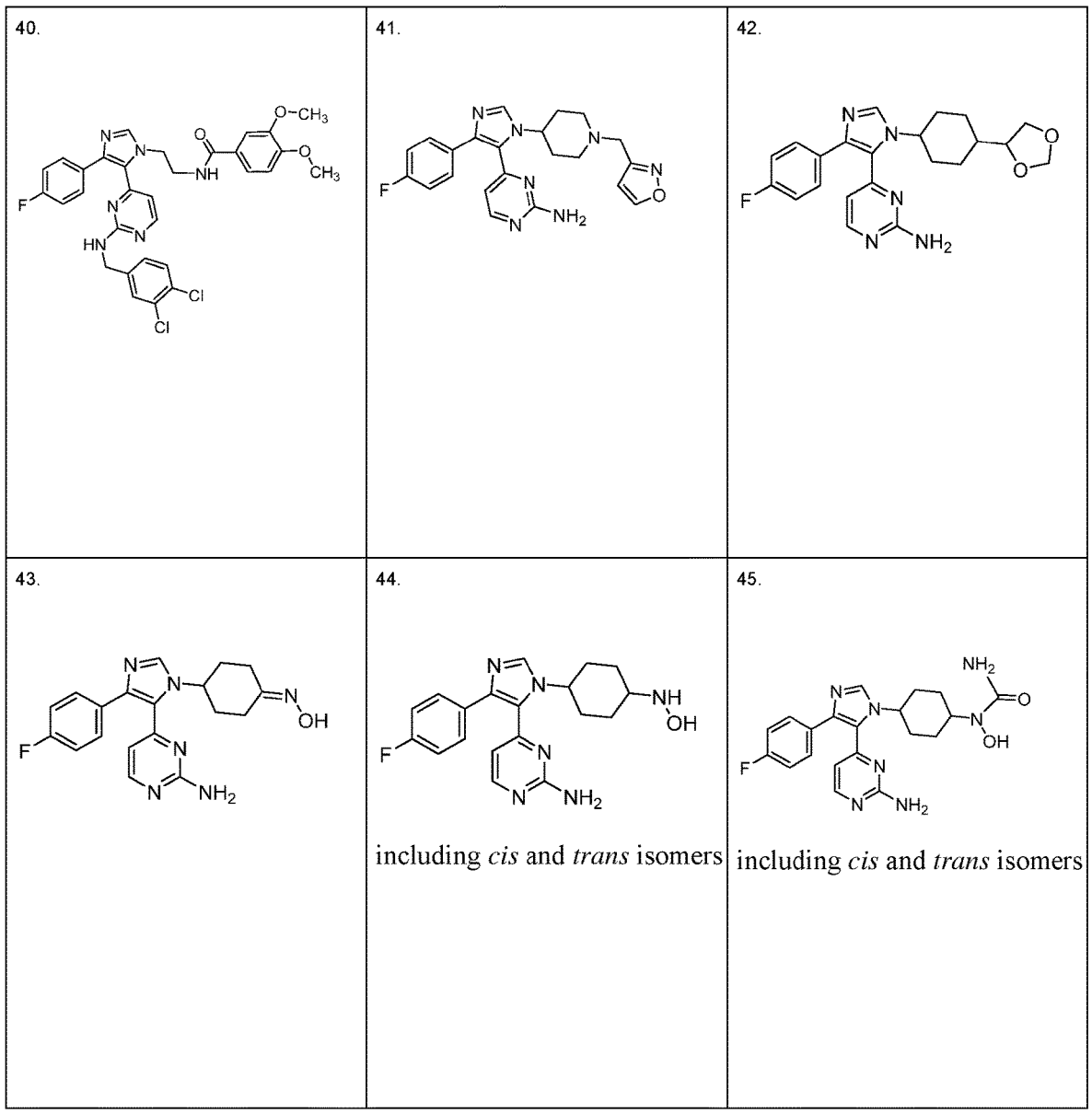
Figure 1:
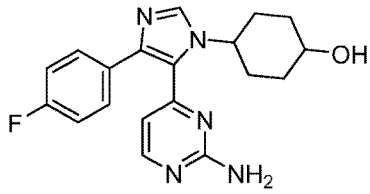
Figure 1:
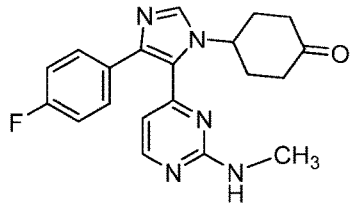
Figure 1:
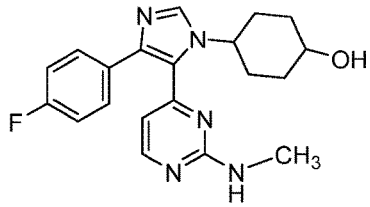
Figure 1:
Figure 1:
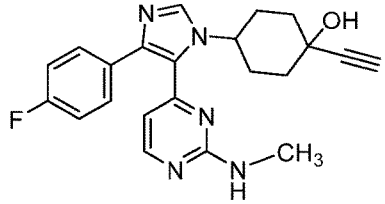
Figure 1:
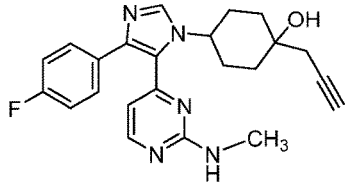
Figure 1:
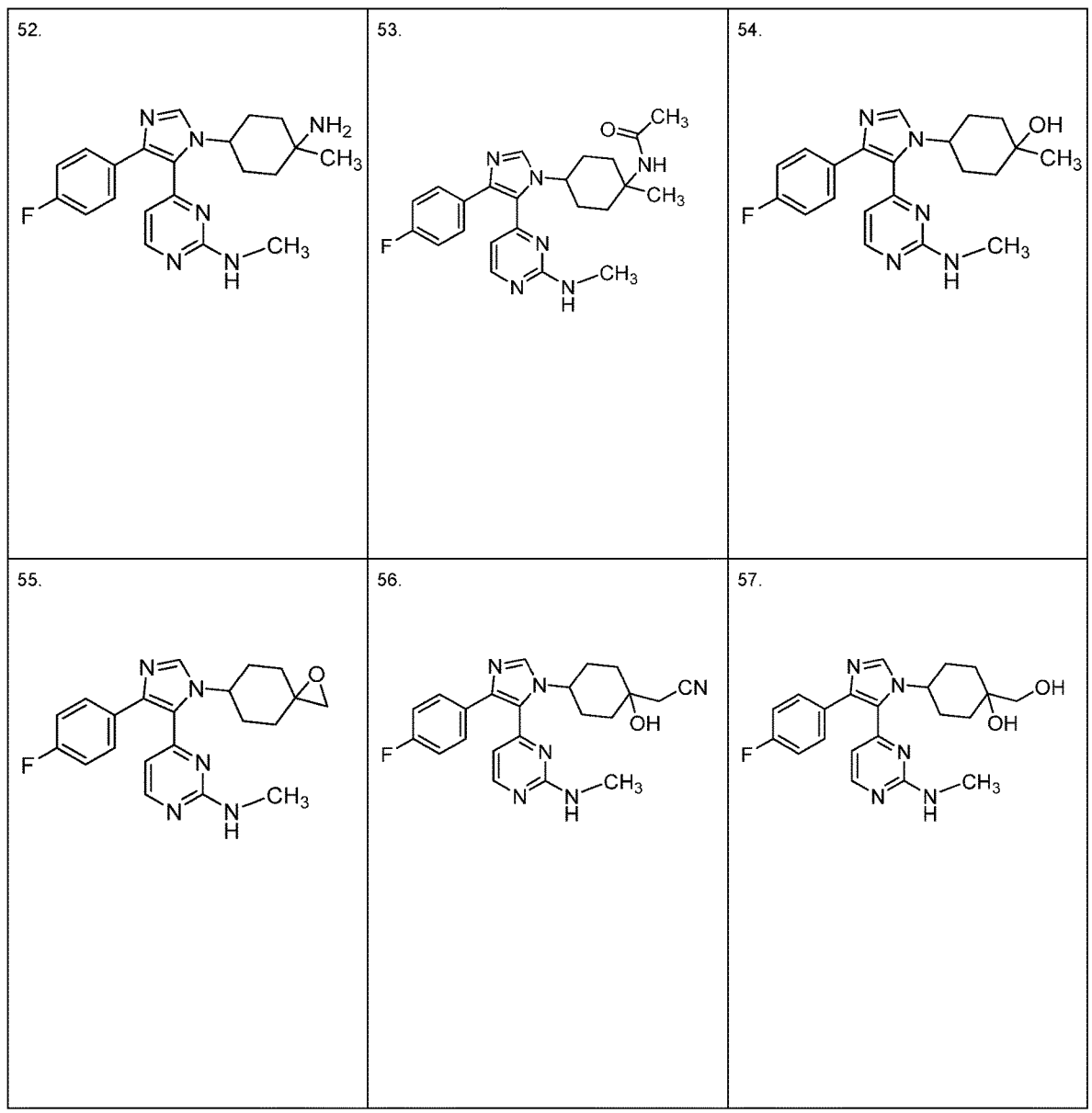
Figure 1:
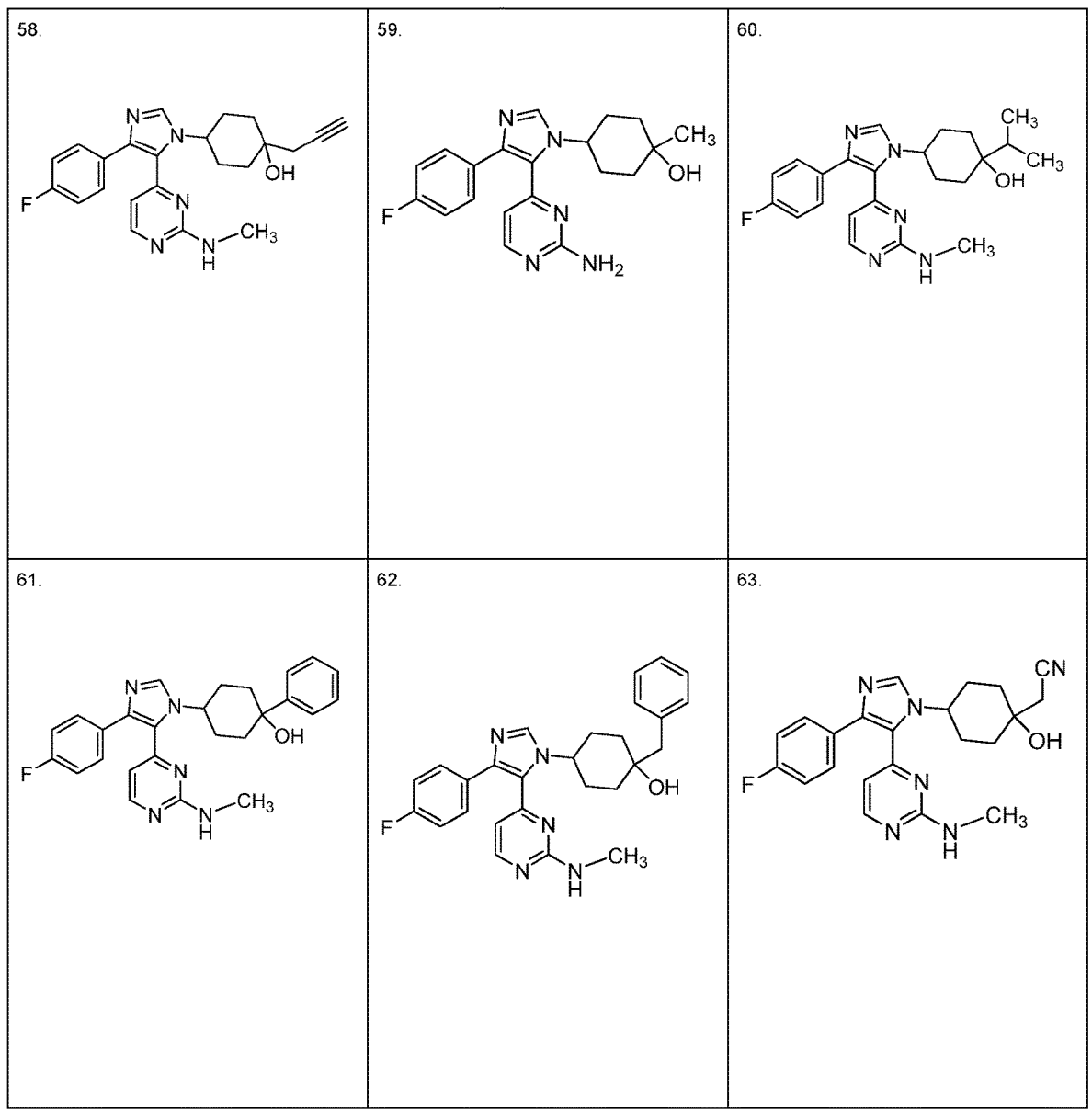
Figure 1:
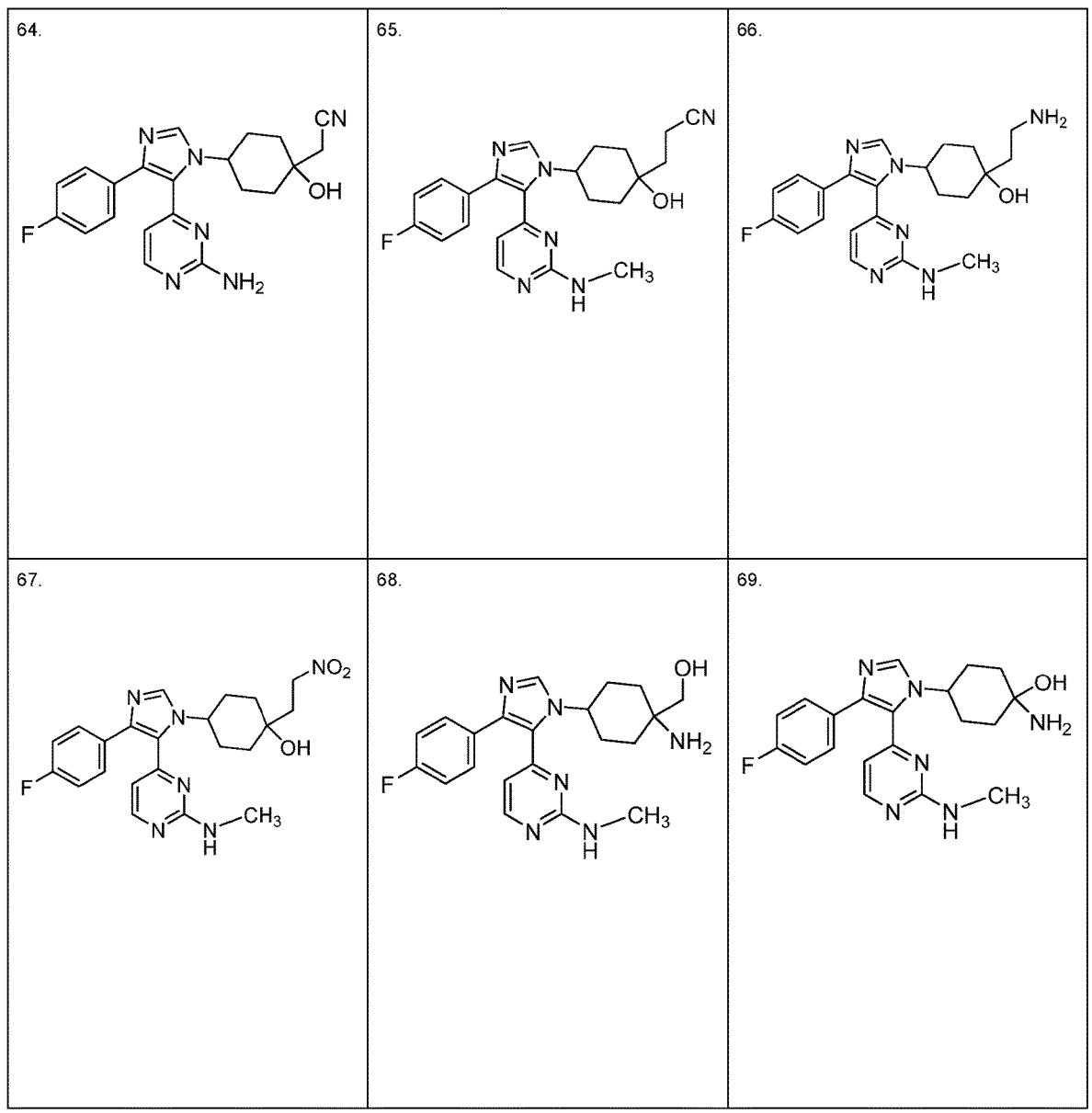
Figure 1:
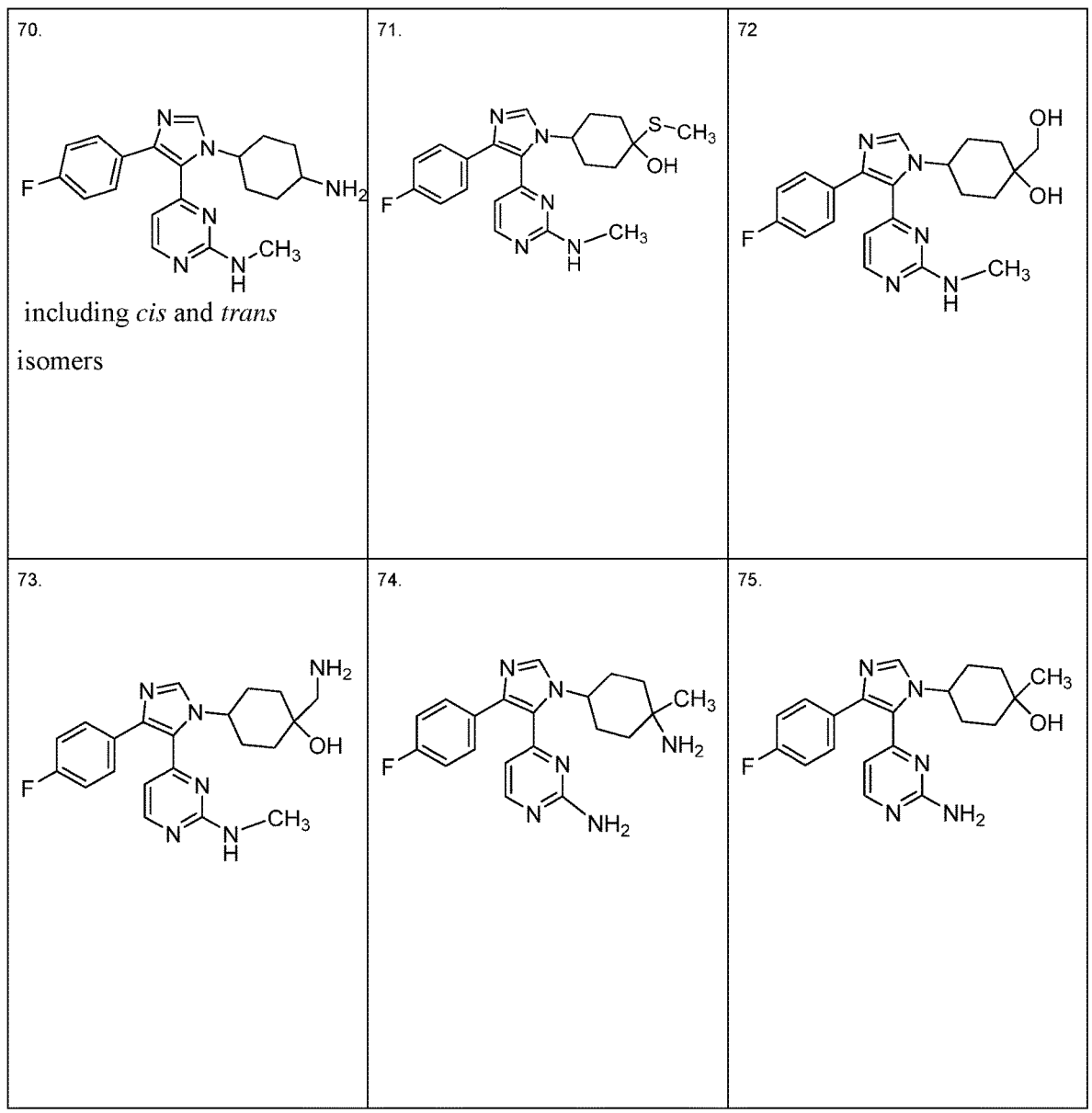
Figure 1:
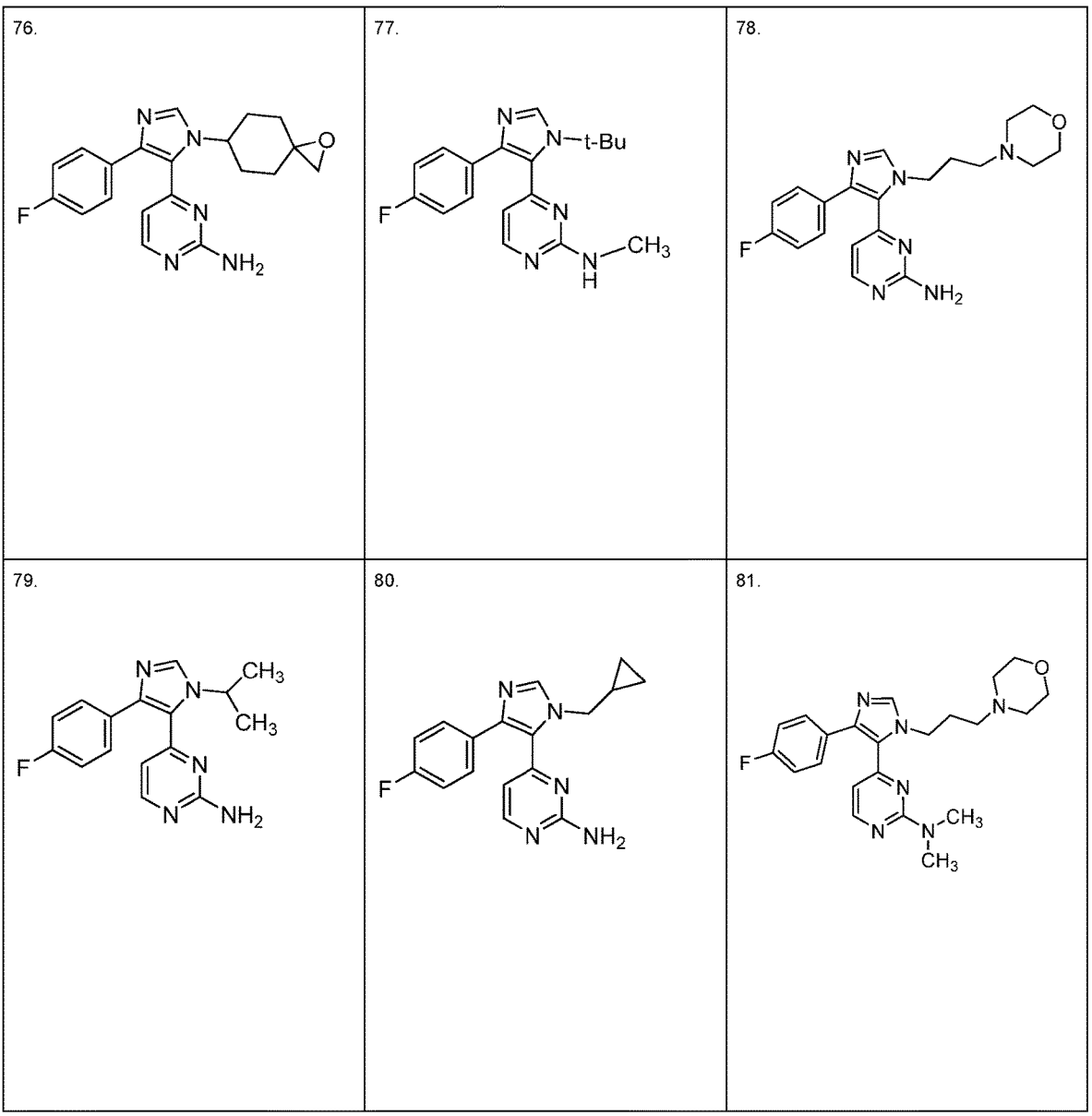
Figure 1:
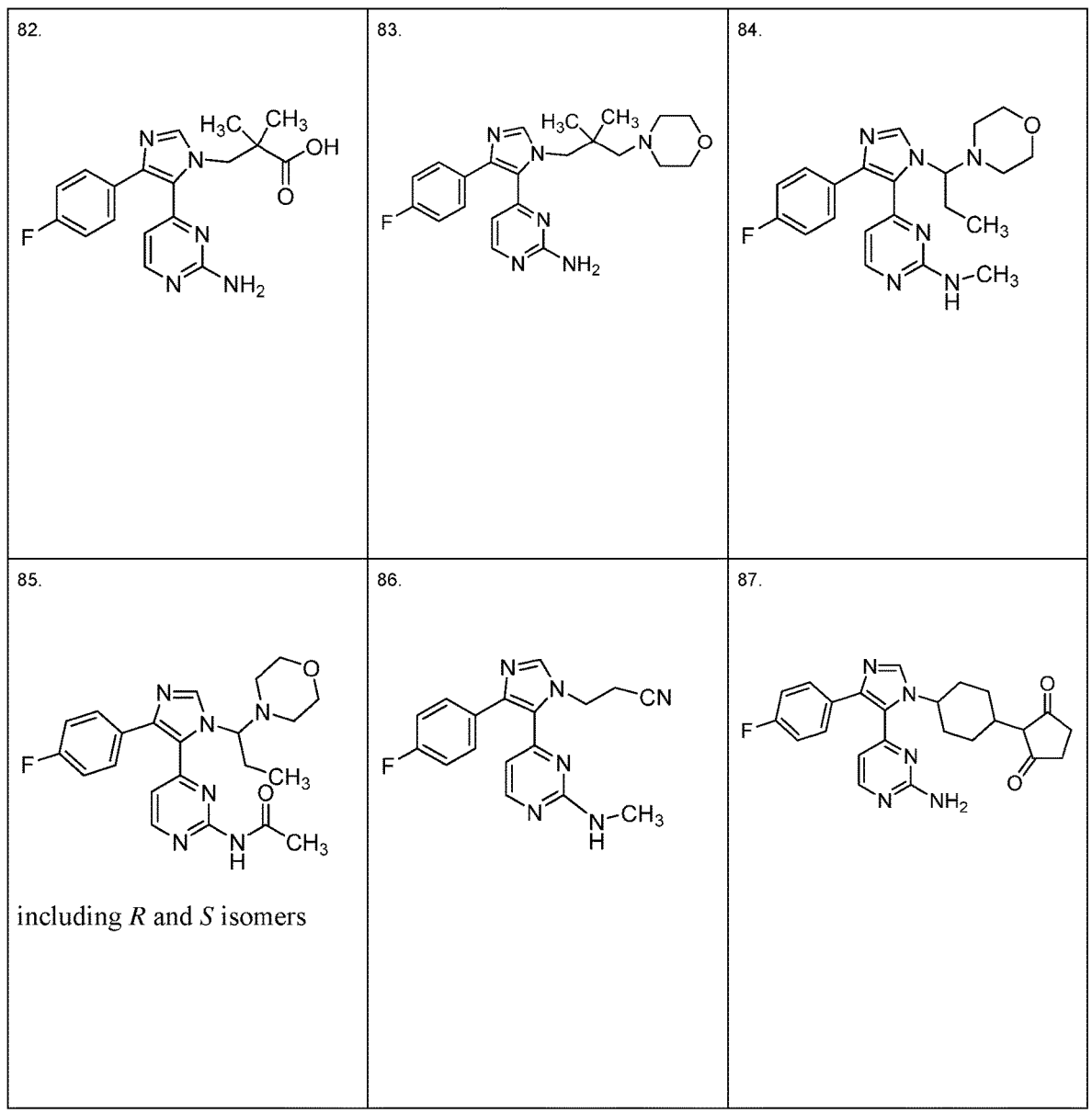
Figure 1:
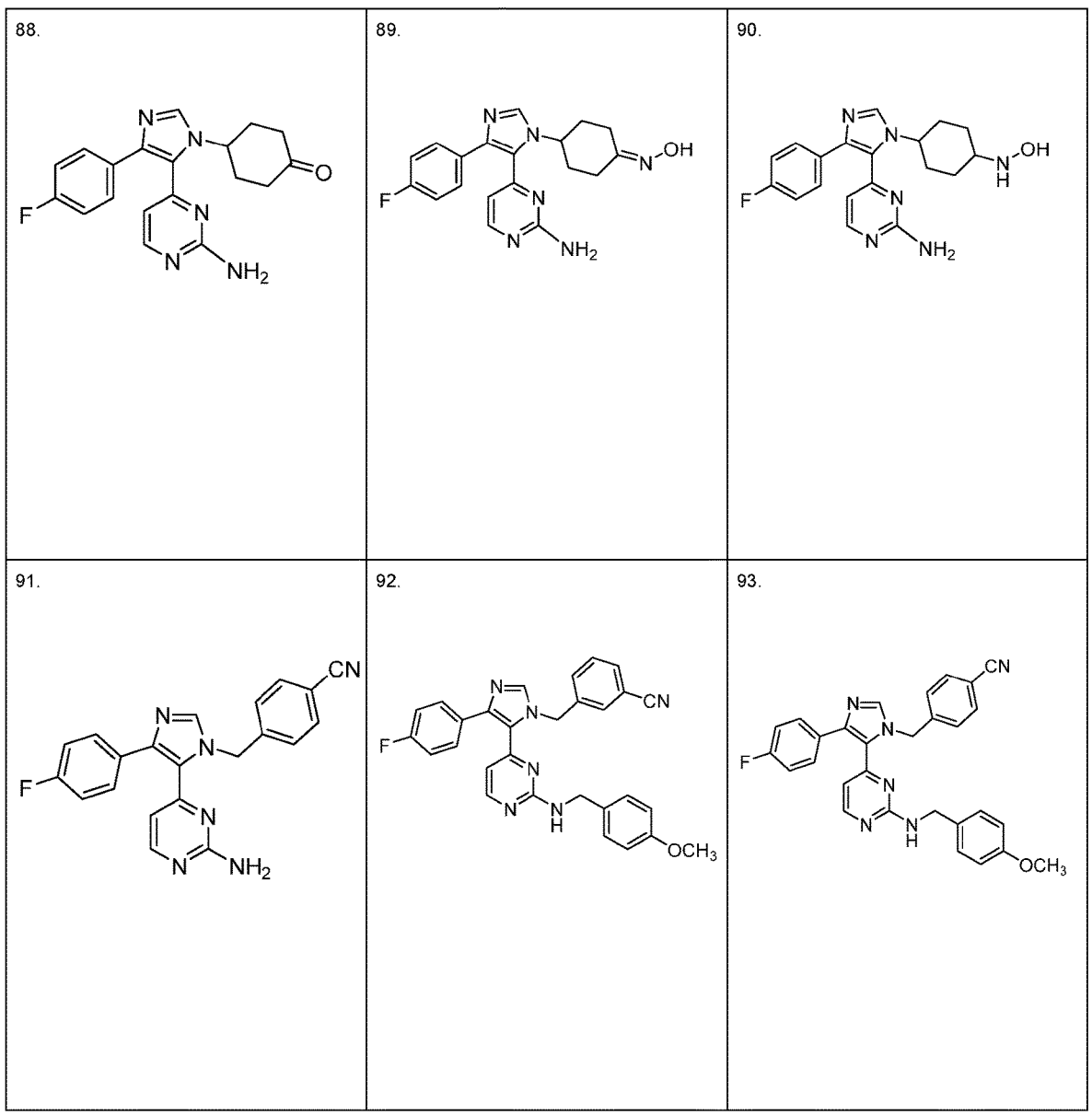
Figure 1:
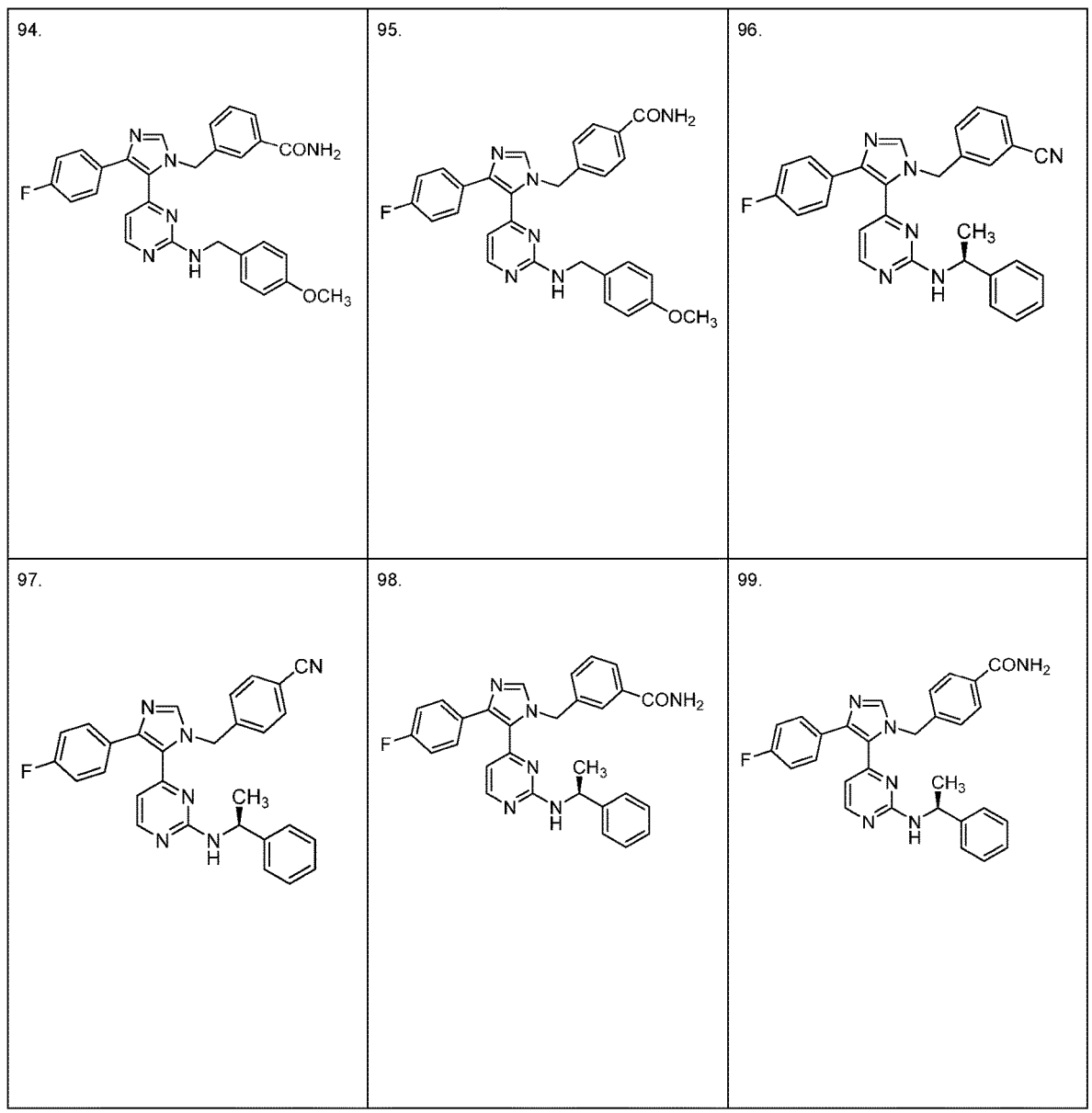
Figure 1:
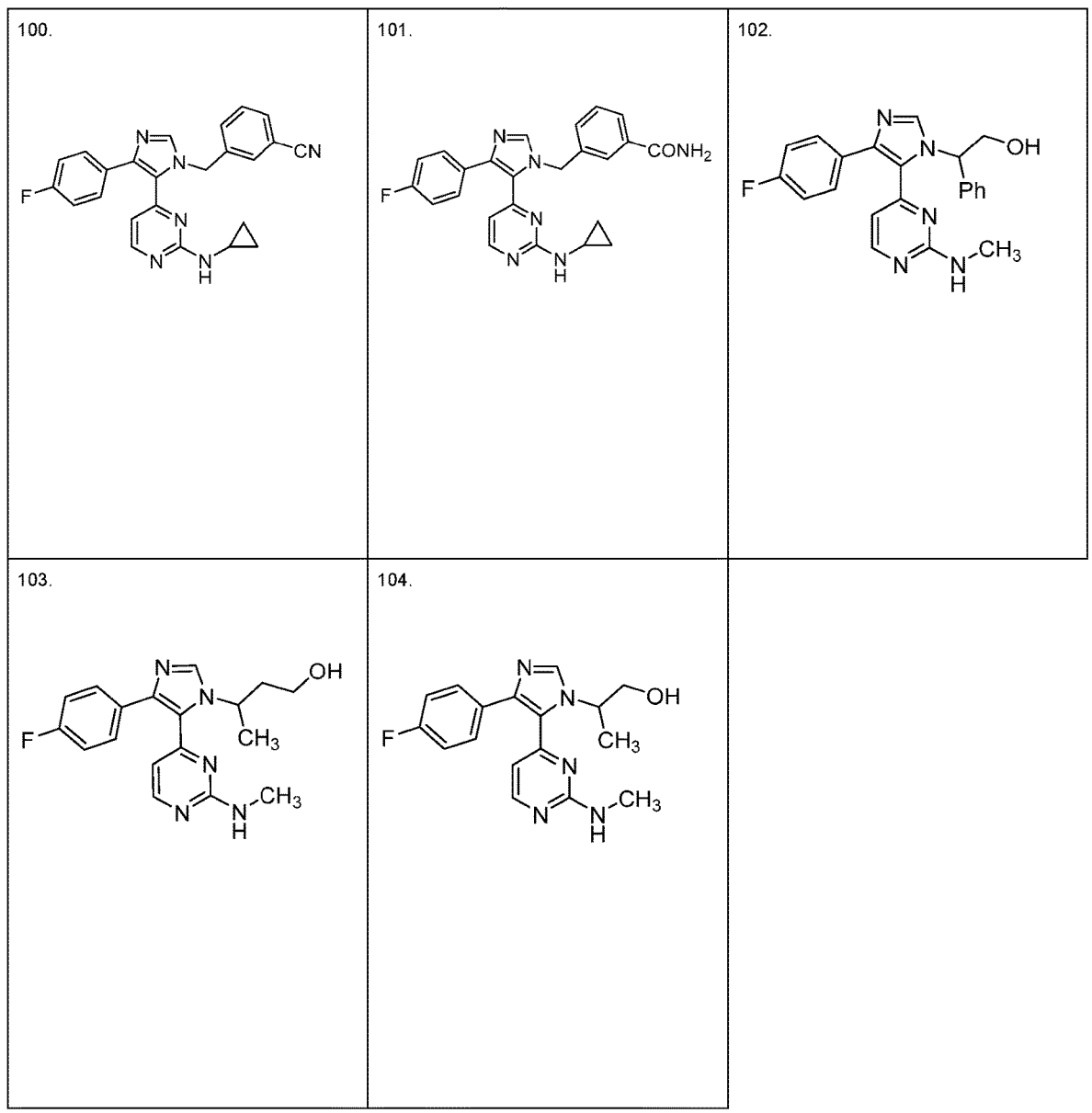

In any one of the embodiments, the present invention provides a compound of formula (I) or (II) provided that the compound is not selected from the list of compounds in FIG. 1. Various compounds are also described in Keenan, et al. *Frontiers in Pharmacology*, 2018, vol 9, article 738; WO2016/149756A1; WO1996/021654A1; WO1999/032121A1; WO1997/035856A1; Kim, D-K., et al. *Bioorganic & Medicinal Chemistry Letters*, 2008, 18, 4006-4010; WO1999/001136A1; U.S. Pat. No. 6,369,068B1; and WO2018/201192A1. In some embodiments, any specific compound described in one or more of these documents may be excluded by way of proviso.

In any one of the embodiments, the present invention provides a compound of formula (I) wherein $R^2$ is H.

In any one of the embodiments, $R_1$ is $C_{1-3}$alkyl$C_{6-12}$aryl. $R^1$ may be $C_{2-3}$alkyl$C_{6-12}$aryl or a $C_{1-3}$alkyl$C_{10-12}$aryl. In some embodiments, $R^1$ an optionally substituted $C_{2-3}$alkyl$C_{6-12}$aryl or a $C_{1-3}$alkyl$C_{10-12}$aryl (eg an unsubstituted $C_{1-3}$alkyl$C_{10-12}$aryl). In some embodiments, the $C_{2-3}$ alkyl$C_{6-12}$ aryl is a optionally substituted $C_{2-3}$ alkyl$C_6$aryl. The $C_{6-12}$ aryl group(s) may be composed of two ring systems. The ring joined to the $C_{1-3}$ alkyl group may have the second ring in any position i.e. ortho, meta or para. When $R^1$ is $C_{1-3}$ alkyl$C_{6-12}$ aryl, $R^2$ may be H.

In any one of the embodiments, $R^1$ is $C_{1-3}$ alkyl$C_{5-11}$heteroaryl. $R^1$ may be $C_{1-2}$alkyl$C_{5-11}$heteroaryl. The $C_{5-11}$heteroaryl group may be composed of two ring systems. The ring joined to the $C_{1-3}$ alkyl group may have the second ring in any position i.e. ortho, meta or para. The heteroaryl group may be selected from an oxygen-containing heteroaryl group, a nitrogen-containing heteroaryl group, or a sulphur-containing heteroaryl group, or a heteroaryl group containing a combination of two or more oxygen, nitrogen and sulphur atoms. Examples include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, and pyrimidyl. The heteroatom may be in the ortho and/or para position relative to the $C_{1-3}$ alkyl group. When $R^1$ is $C_{1-3}$ alkyl$C_{5-11}$heteroaryl, $R^2$ may be H.

In any one of the embodiments, $R^1$ is $C_{1-3}$ alkyl$C_{3-6}$ cycloalkyl. $R^1$ may be $C_{1-2}$alkyl$C_{3-6}$ cycloalkyl. The $C_{3-6}$ cycloalkyl group may be selected from cyclopropyl, cyclobutyl, cyclopentyl and cyclohexyl. When $R^1$ is $C_{1-3}$ alkyl$C_{3-6}$ cycloalkyl, $R^2$ may be H. When $R^1$ is $C_{1-3}$ alkyl$C_{3-6}$ cycloalkyl, $R^1$ may be substituted. The substituent may be selected from $C_{1-3}$ alkyl.

In any one of the embodiments, $R^1$ is $C_{1-3}$ alkyl$C_{3-6}$ heterocyclyl. $R^1$ may be $C_{1-2}$alkyl$C_{3-6}$ heterocyclyl. $R^1$ may be selected from an oxygen-containing heterocyclyl group, a nitrogen-containing heterocyclyl group, or a sulphur-containing heterocyclyl group, or a heterocyclyl group containing a combination of two or more oxygen, nitrogen and sulphur atoms. Examples include oxetanyl, thietanyl, pyrrolidinyl, pyridinyl, pyrazolidinyl, imidazolidinyl, terahydrofuranyl, 1,3-dioxolanyl, tetrahydropyranyl, tetrahydrothipheneyl, and 1,2- and 1,3-oxathiolanyl. When $R^1$ is $C_{1-3}$ alkyl$C_{3-6}$ heterocyclyl, $R^2$ may be H.

In any one of the embodiments, $R^1$ may be selected from any one of the following groups G1-G7:

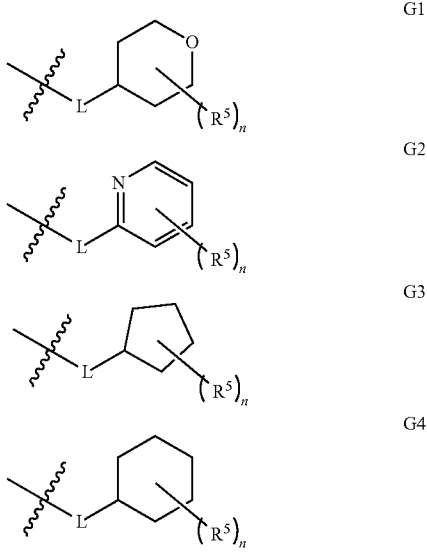

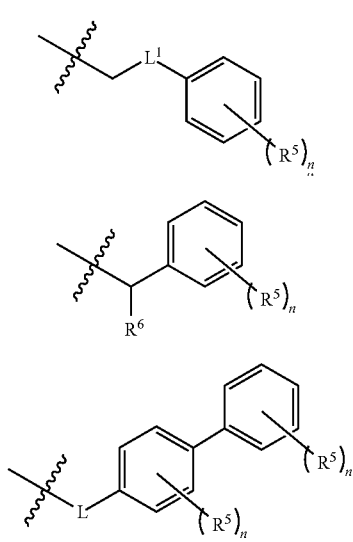

wherein
each $R^5$ is selected from any of the optional substituents described herein. In some embodiments, $R^5$ is selected from the group consisting of $C_{1-6}$ alkyl, $C_{1-6}$haloalkyl, $C_{1-6}$ haloalkoxy, $C_{1-6}$ hydroxyalkyl, $C_{3-7}$heterocyclyl, $C_{3-7}$ cycloalkyl, $C_{2-6}$alkoxy, $C_{1-6}$ alkylsulfanyl, $C_{1-6}$ alkylsulfenyl, $C_{1-6}$ alkylsulfonyl, $C_{1-6}$ alkylsulfonylamino, arylsulfonoamino, alkylcarboxy, alkylcarboxyamide, oxo, hydroxy, mercapto, amino, acyl, carboxy, carbamoyl, aryl, aryloxy, heteroaryl, aminosulfonyl, aroyl, aroylamino, heteroaroyl, acyloxy, aroyloxy, heteroaroyloxy, alkoxycarbonyl, nitro, cyano, fluoro, iodo, bromo, ureido or $C_{1-6}$ perfluoroalkyl, each of which may be optionally substituted;
$R^6$ is optionally substituted $C_{1-2}$ alkyl;
L is $(CR^7R^8)_m$;
$L^1$ is $(CR^7R^8)_p$ optionally substituted $C_{1-2}$ alkyl;
$R^7$ and $R^8$ are independently selected from H and optionally substituted $C_{1-6}$alkyl;
n is selected from 0, 1, 2 and 3;
m is selected from 1, 2 and 3; and
p is selected from 1 and 2.

In any one of the embodiments of groups G1-G7, n may be 0, 1 or 2.

In any one of the embodiments, $R^5$ is fluoro.

In any one of the embodiments, n is 0, 1 or 2.

In any one of the embodiments, $R^1$ may be selected from G1-G5.

In any one of the embodiments, $R^1$ may be G6. In some embodiments of G6, $R^6$ is optionally substituted methyl.

In any one of the embodiments, $R^1$ is a group selected from G1-G7 and $R^4$ is selected from $C_{3-12}$ cycloalkyl, $C_{1-12}$ alkyl and halo$C_{1-12}$alkyl. In some of these embodiments, $R^4$ may be unsubstituted. In some embodiments, $R^4$ is optionally substituted by one or more substituents selected from $C_{1-6}$ alkyl and halo.

In any one of the embodiments, the present invention provides a compound of formula (I) wherein $R^3$ is $CH_3$. $R^3$ may be F or Cl. Preferably, $R^3$ is F.

In any one of the embodiments, the present invention provides a compound of formula (I) wherein $R^4$ is $C_{0-3}$ alkyl$C_{3-12}$ cycloalkyl. $R^4$ may be $C_{0-3}$ alkyl$C_{3-12}$ cycloalkyl, wherein the $C_{3-12}$ cycloalkyl group is selected from cyclopropyl, cyclobutyl, cyclopentyl, cyclohexyl and cycloheptyl. In a preferred form, $R^4$ is $C_{3-12}$ cycloalkyl. More preferably, $R^4$ is selected from cyclopropyl, cyclobutyl, cyclopentyl, cyclohexyl and cycloheptyl. $R^4$ may be $C_{1-2}$ alkyl$C_{3-12}$ cycloalkyl. $R^4$ may be $C_1$alkyl$C_{3-12}$ cycloalkyl. In some embodiments, $R^4$ is selected from $C_{0-3}$ alkyl$C_{4-12}$ cycloalkyl, $C_3$cycloalkyl and $C_{2-3}$alkyl$C_3$cycloalkyl. The $C_{3-12}$ cycloalkyl group may be selected from cyclopropyl, cyclobutyl, cyclopentyl, cyclohexyl and cycloheptyl. When $R^4$ is $C_{0-3}$ alkyl$C_{3-12}$cycloalkyl, $R^4$ may be substituted. The $C_{3-12}$ cycloalkyl group may be substituted. The substituent may be selected from one or more $C_{1-6}$ alkyl groups, one or more halo groups, and one or more OH groups. In some embodiments, the substituent is selected from one or more $C_{1-6}$ alkyl groups and one or more halo groups (eg —F).

In any one of the embodiments, the present invention provides a compound of formula (I) wherein $R^4$ is $C_{1-12}$ alkyl. $R^4$ may be a methyl, ethyl, propyl or butyl group. $R^4$ may be a branched $C_{1-12}$ alkyl group, such as a branched $C_3$, $C_4$ or $C_5$ alkyl group. $R^4$ may be substituted by one or more groups selected from halo and OH. For example, $R^4$ may be substituted by one, two, or more halo groups.

In any one of the embodiments, $R^4$ is selected from $C_{5-6}$ cycloalkyl and halo$C_{2-5}$alkyl. In some embodiments, $R^4$ is selected from cyclohexyl and trifluoroethyl (eg —$CH_2CF_3$).

In any one of the embodiments, $R^1$, $R^2$, $R^3$ and $R^4$ are optionally substituted by one or more groups selected from OH, $C_{1-6}$ alkoxy, halo (eg fluoro), amino, mercapto and $C_{1-6}$ alkyl.

As used herein the term "$C_{1-12}$ alkyl" refers to a straight or branched chain hydrocarbon radical having from one to twelve carbon atoms, or any range between, i.e. it contains 1, 2, 3, 4, 5, 6, 7, 8, 9, 10, 11 or 12 carbon atoms. The alkyl group is optionally substituted with substituents, multiple degrees of substitution being allowed. Examples of "$C_{1-12}$ alkyl" as used herein include, but are not limited to, methyl, ethyl, n-propyl, isopropyl, n-butyl, isobutyl, t-butyl, n-pentyl, isopentyl, and the like.

"$C_{1-3}$alkyl", "$C_{1-4}$alkyl" and "$C_{1-6}$ alkyl" are preferred. These groups refer to an alkyl group containing 1-3, 1-4 or 1-6 carbon atoms, respectively, or any range in between (e.g. alkyl groups containing 2-5 carbon atoms, i.e. 2, 3, 4 or 5 carbon atoms, are also within the range of $C_{1-6}$). Where the term "$C_{0-2}$ alkyl", or the like, is used, there may be no alkyl group, or an alkyl group containing 1 or 2 carbon atoms.

The term "$C_{2-6}$ alkenyl" refers to optionally substituted straight chain or branched chain hydrocarbon groups having at least one double bond of either E or Z stereochemistry where applicable and 2 to 6 carbon atoms. Examples include vinyl, 1-propenyl, 1- and 2-butenyl and 2-methyl-2-propenyl. Unless the context requires otherwise, the term "$C_{2-6}$ alkenyl" also encompasses alkenyl groups containing one less hydrogen atom such that the group is attached via two positions i.e. divalent. "$C_{2-4}$ alkenyl" and "$C_{2-3}$ alkenyl" including ethenyl, propenyl and butenyl are preferred with ethenyl being particularly preferred.

The term "$C_{2-6}$ alkynyl" refers to optionally substituted straight chain or branched chain hydrocarbon groups having at least one triple bond and 2 to 6 carbon atoms. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl and the like. Unless the context indicates otherwise, the term "$C_{2-6}$ alkynyl" also encompasses alkynyl groups containing one less hydrogen atom such that the group is attached via two positions i.e. divalent. $C_{2-3}$ alkynyl is preferred.

As used herein, the term "halogen" refers to fluorine (F), chlorine (Cl), bromine (Br), or iodine (I) and the term "halo" refers to the halogen radicals fluoro (—F), chloro (—Cl), bromo (—Br), and iodo (—I). Preferably, 'halo' is fluoro.

As used herein, the term "cycloalkyl" refers to a non-aromatic cyclic hydrocarbon ring. The term "$C_{3-7}$ cycloalkyl" refers to a non-aromatic cyclic hydrocarbon ring having from three to seven carbon atoms, or any range of integers in between. For example, the $C_{3-7}$ cycloalkyl group would also include cycloalkyl groups containing 4 to 6 (i.e. 4, 5 or 6) carbon atoms. The alkyl group is as defined above, and may be substituted. Exemplary "$C_{3-7}$ cycloalkyl" groups useful in the present invention include, but are not limited to, cyclopropyl, cyclobutyl, cyclopentyl, cyclohexyl and cycloheptyl.

Cycloalkyl groups may optionally be fused to one or more heterocyclic or cycloalkyl rings. Cycloalkyl rings may be substituted at any of the carbon atoms on the ring with another cycloalkyl or heterocyclic moiety to form a spirocycloalkyl or spiroheteroalkyl compound.

Two non-adjacent atoms on the cycloalkyl group may be bridged by an alkyl or heteroalkyl group to form a bridged system. Preferably, the bridging group is 1-3 atoms in length.

As used herein, the terms "heterocyclic" or "heterocyclyl" refer to a non-aromatic heterocyclic ring, being saturated or having one or more degrees of unsaturation, containing one or more heteroatom substitution selected from S, S(O), S(O)$_2$, O, or N. The term "$C_{3-7}$heterocyclyl" refers to a non-aromatic cyclic hydrocarbon ring having from three to seven carbon atoms (i.e. 3, 4, 5, 6 or 7 carbon atoms) containing one or more heteroatom substitutions as referred to herein. The heterocyclic moiety may be substituted, multiple degrees of substitution being allowed. The term "$C_{3-7}$ heterocyclyl" also includes heterocyclyl groups containing $C_{4-5}$, $C_{5-7}$, $C_{6-7}$, $C_{4-7}$, $C_{4-6}$ and $C_{5-6}$ carbon atoms. Preferably, the heterocyclic ring contains four to six carbon atoms and one or two heteroatoms. More preferably, the heterocyclic ring contains five carbon atoms and one heteroatom, or four carbon atoms and two heteroatom substitutions, or five carbon atoms and one heteroatom. The heterocyclyl groups may be 3 to 10-membered ring systems, which denotes the total number of atoms (carbon atoms and heteroatoms) contained within the ring system. In this context, the prefixes 3-, 4-, 5-, 6-, 7-, 8-, 9- and 10-membered denote the number of ring atoms, or range of ring atoms, whether carbon atoms or heteroatoms. For example, the term "3-10 membered heterocylyl", as used herein, pertains to a heterocyclyl group having 3, 4, 5, 6, 7, 8, 9 or 10 ring atoms. Examples of heterocylyl groups include 5-6-membered monocyclic heterocyclyls and 9-10 membered fused bicyclic heterocyclyls. Accordingly, heterocyclyl rings described herein may be optionally fused to one or more other "heterocyclic" ring(s), cycloalkyl ring(s), aryl ring(s) or heteroaryl ring(s). Examples of "heterocyclic" moieties include, but are not limited to, tetrahydrofuran, pyran, oxetane, 1,4-dioxane, 1,3-dioxane, piperidine, piperazine, N-methylpiperazinyl, 2,4-piperazinedione, pyrrolidine, imidazolidine, pyrazolidine, morpholine, thiomorpholine, tetrahydrothiopyran, tetrahydrothiophene, and the like.

Heterocyclic groups may be substituted at any of the carbons on the ring with another heterocyclic or cycloalkyl moiety to form a spirocycloalkyl or spiroheteroalkyl compound.

Two non-adjacent atoms on the heterocyclic group may further be bridged by an alkyl or heteroalkyl group to form a bridged system. Preferably, the bridging group is 1-3 atoms in length.

As an example of substituted heterocyclic groups, the term "$C_{0-2}$ alkyl$C_{3-7}$heterocyclyl" includes heterocyclyl groups containing either no alkyl group as a linker between the compound and the heterocycle, or an alkyl group containing 1 or 2 carbon atoms as a linker between the compound and the heterocycle (i.e. heterocycle, —CH$_2$-heterocycle or —CH$_2$CH$_2$-heterocycle). These heterocycles may be further substituted.

Substituted cycloalkyl and heterocyclyl groups may be substituted with any suitable substituent as described below.

As used herein, the term "aryl" refers to an optionally substituted benzene ring or to an optionally substituted benzene ring system fused to one or more optionally substituted benzene rings to form, for example, anthracene, phenanthrene, or naphthalene ring systems. Examples of "aryl" groups include, but are not limited to, phenyl, 2-naphthyl, 1-naphthyl, biphenyl, as well as substituted derivatives thereof. Preferred substituted aryl groups include arylamino, arylalkyl, arylalkylhalo, arylhalo and aralkoxy groups.

As used herein, the term "heteroaryl" refers to a monocyclic five, six or seven membered aromatic ring, or to a fused bicyclic or tricyclic aromatic ring system comprising at least one monocyclic five, six or seven membered aromatic ring. These heteroaryl rings contain one or more nitrogen, sulfur, and/or oxygen heteroatoms, and may be optionally substituted with up to three members. N-containing heteroaryls may be in the form of an N-oxide and S-containing heteroaryls may be in the form of sulfur oxides and dioxides. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, benzimidazolyl, and substituted versions thereof.

The terms "hydroxy" and "hydroxyl" refer to the group —OH.

The term "oxo" refers to the group =O.

The term "$C_{1-6}$ alkoxy" refers to an alkyl group as defined above covalently bound via an O linkage containing 1 to 6 carbon atoms, such as methoxy, ethoxy, propoxy, isopropoxy, butoxy, tert-butoxy and pentoxy. "$C_{1-4}$ alkoxy" and "$C_{1-3}$ alkoxy" including methoxy, ethoxy, propoxy and butoxy are preferred with methoxy being particularly preferred.

The terms "halo$C_{1-6}$ alkyl" and "$C_{1-6}$ alkylhalo" refer to a $C_{1-6}$ alkyl which is substituted with one or more halogens. Halo$C_{1-3}$ alkyl groups are preferred, such as for example, —CH$_2$CF$_3$, and —CF$_3$.

The terms "halo$C_{1-6}$ alkoxy" and "$C_{1-6}$ alkoxyhalo" refer to a $C_{1-6}$ alkoxy which is substituted with one or more halogens. $C_{1-3}$ alkoxyhalo groups are preferred, such as for example, —OCF$_3$.

The term "carboxylate" or "carboxyl" refers to the group —COO— or —COOH.

The term "ester" refers to a carboxyl group having the hydrogen replaced with, for example a $C_{1-6}$ alkyl group ("carboxyl$C_{1-6}$ alkyl" or "alkylester"), an aryl or aralkyl group ("arylester" or "aralkylester") and so on. CO$_2$C$_{1-3}$ alkyl groups are preferred, such as for example, methylester (CO$_2$Me), ethylester (CO$_2$Et) and propylester (CO$_2$Pr) and includes reverse esters thereof (e.g. —OC(O)Me, —OC(O)Et and —OC(O)Pr).

The terms "cyano" and "nitrile" refer to the group —CN.

The term "nitro" refers to the group —NO$_2$.

The term "amino" refers to the group —NH$_2$.

The term "substituted amino" or "secondary amino" refers to an amino group having a hydrogen replaced with, for example a C$_{1-6}$ alkyl group ("C$_{1-6}$ alkylamino"), an aryl or aralkyl group ("arylamino", "aralkylamino") and so on. C$_{1-3}$ alkylamino groups are preferred, such as for example, methylamino (NHMe), ethylamino (NHEt) and propylamino (NHPr).

The term "disubstituted amino" or "tertiary amino" refers to an amino group having the two hydrogens replaced with, for example a C$_{1-6}$ alkyl group, which may be the same or different ("dialkylamino"), an aryl and alkyl group ("aryl (alkyl)amino") and so on. Di(C$_{1-3}$ alkyl)amino groups are preferred, such as for example, dimethylamino (NMe$_2$), diethylamino (NEt$_2$), dipropylamino (NPr$_2$) and variations thereof (e.g. N(Me)(Et) and so on).

The term "aldehyde" refers to the group —C(=O)H.

The term "acyl" refers to the group —C(O)CH$_3$.

The term "ketone" refers to a carbonyl group which may be represented by —C(O)—.

The term "substituted ketone" refers to a ketone group covalently linked to at least one further group, for example, a C$_{1-6}$ alkyl group ("C$_{1-6}$ alkylacyl" or "alkylketone" or "ketoalkyl"), an aryl group ("arylketone"), an aralkyl group ("aralkylketone") and so on. C$_{1-3}$ alkylacyl groups are preferred.

The term "amido" or "amide" refers to the group —C(O)NH$_2$.

The term "substituted amido" or "substituted amide" refers to an amido group having a hydrogen replaced with, for example a C$_{1-6}$ alkyl group ("C$_{1-6}$ alkylamido" or "C$_{1-6}$ alkylamide"), an aryl ("arylamido"), aralkyl group ("aralkylamido") and so on. C$_{1-3}$ alkylamide groups are preferred, such as for example, methylamide (—C(O)NHMe), ethylamide (—C(O)NHEt) and propylamide (—C(O)NHPr) and includes reverse amides thereof (e.g. —NHMeC(O)—, —NHEtC(O)— and —NHPrC(O)—).

The term "disubstituted amido" or "disubstituted amide" refers to an amido group having the two hydrogens replaced with, for example a C$_{1-6}$ alkyl group ("di(C$_{1-6}$alkyl)amido" or "di(C$_{1-6}$ alkyl)amide"), an aralkyl and alkyl group ("alkyl (aralkyl)amido") and so on. Di(C$_{1-3}$ alkyl)amide groups are preferred, such as for example, dimethylamide (—C(O)NMe$_2$), diethylamide (—C(O)NEt$_2$) and dipropylamide ((—C(O)NPr$_2$) and variations thereof (e.g. —C(O)N(Me)Et and so on) and includes reverse amides thereof.

The term "thiol" refers to the group —SH.

The term "C$_{1-6}$ alkylthio" refers to a thiol group having the hydrogen replaced with a C$_{1-6}$ alkyl group. C$_{1-3}$ alkylthio groups are preferred, such as for example, thiolmethyl, thiolethyl and thiolpropyl.

The terms "thioxo" refer to the group =S.

The term "sulfinyl" refers to the group —S(=O)H.

The term "substituted sulfinyl" or "sulfoxide" refers to a sulfinyl group having the hydrogen replaced with, for example a C$_{1-6}$ alkyl group ("C$_{1-6}$ alkylsulfinyl" or "C$_{1-6}$ alkylsulfoxide"), an aryl ("arylsulfinyl"), an aralkyl ("aralkyl sulfinyl") and so on. C$_{1-3}$alkylsulfinyl groups are preferred, such as for example, —SOmethyl, —SOethyl and —SOpropyl.

The term "sulfonyl" refers to the group —SO$_2$H.

The term "substituted sulfonyl" refers to a sulfonyl group having the hydrogen replaced with, for example a C$_{1-6}$ alkyl group ("sulfonylC$_{1-6}$ alkyl"), an aryl ("arylsulfonyl"), an aralkyl ("aralkylsulfonyl") and so on. SulfonylC$_{1-3}$ alkyl groups are preferred, such as for example, —SO$_2$Me, —SO$_2$Et and —SO$_2$Pr.

The term "sulfonylamido" or "sulfonamide" refers to the group —SO$_2$NH$_2$.

The term "substituted sulfonamido" or "substituted sulphonamide" refers to an sulfonylamido group having a hydrogen replaced with, for example a C$_{1-6}$ alkyl group ("sulfonylamidoC$_{1-6}$ alkyl"), an aryl ("arylsulfonamide"), aralkyl ("aralkylsulfonamide") and so on. SulfonylamidoC$_{1-3}$ alkyl groups are preferred, such as for example, —SO$_2$NHMe, —SO$_2$NHEt and —SO$_2$NHPr and includes reverse sulfonamides thereof (e.g. —NHSO$_2$Me, —NHSO$_2$Et and —NHSO$_2$Pr).

The term "disubstituted sufonamido" or "disubstituted sulphonamide" refers to an sulfonylamido group having the two hydrogens replaced with, for example a C$_{1-6}$alkyl group, which may be the same or different ("sulfonylamidodi(C$_{1-6}$ alkyl)"), an aralkyl and alkyl group ("sulfonamido(aralkyl) alkyl") and so on. Sulfonylamidodi(C$_{1-3}$alkyl) groups are preferred, such as for example, —SO$_2$NMe$_2$, —SO$_2$NEt$_2$ and —SO$_2$NPr$_2$ and variations thereof (e.g. —SO$_2$N(Me)Et and so on) and includes reserve sulfonamides thereof (e.g. —N(Me)SO$_2$Me and so on).

The term "sulfate" refers to the group OS(O)$_2$OH and includes groups having the hydrogen replaced with, for example a C$_{1-6}$ alkyl group ("alkylsulfates"), an aryl ("arylsulfate"), an aralkyl ("aralkylsulfate") and so on. C$_{1-3}$sulfates are preferred, such as for example, OS(O)$_2$OMe, OS(O)$_2$OEt and OS(O)$_2$OPr.

The term "sulfonate" refers to the group SO$_3$H and includes groups having the hydrogen replaced with, for example a C$_{1-6}$ alkyl group ("alkylsulfonate"), an aryl ("arylsulfonate"), an aralkyl ("aralkylsulfonate") and so on. C$_{1-3}$sulfonates are preferred, such as for example, SO$_3$Me, SO$_3$Et and SO$_3$Pr.

A "substituent" as used herein, refers to a molecular moiety that is covalently bonded to an atom within a molecule of interest. For example, a "ring substituent" may be a moiety such as a halogen, alkyl group, or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterized and tested for biological activity.

The terms "optionally substituted" or "may be substituted" and the like, as used throughout the specification, denotes that the group may or may not be further substituted or fused (so as to form a polycyclic system), with one or more non-hydrogen substituent groups. Suitable chemically viable substituents for a particular functional group will be apparent to those skilled in the art. In some embodiments, an optionally substituted moiety may or may not be further substituted with 1, 2, 3, 4 or more groups, preferably 1, 2 or 3, more preferably 1 or 2 groups.

Examples of substituents include but are not limited to: C$_{1-6}$ haloalkyl, C$_{1-6}$ haloalkoxy, C$_{1-6}$ hydroxyalkyl, C$_{3-7}$ heterocyclyl, C$_{3-7}$cycloalkyl, C$_{1-6}$ alkoxy, C$_{1-6}$ alkylsulfanyl, C$_{1-6}$ alkylsulfenyl, C$_{1-6}$ alkylsulfonyl, C$_{1-6}$alkylsulfonylamino, arylsulfonoamino, alkylcarboxy, alkylcarboxyamide, oxo, hydroxy, mercapto, amino, acyl, carboxy, carbamoyl, aryl, aryloxy, heteroaryl, aminosulfonyl, aroyl, aroylamino, heteroaroyl, acyloxy, aroyloxy, heteroaroyloxy, alkoxycarbonyl, nitro, cyano, halo, ureido, $C_{1-6}$ perfluoroalkyl, $C_{2-6}$ alkenyl, $C_{2-6}$alkynyl, $C_{1-6}$ alkoxyaryl, esters, substituted amino, disubstituted amino, acyl, ketones, substituted ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl$C_{1-6}$ alkyl, heterocyclyl$C_{1-6}$ alkyl, and $C_{3-7}$ cycloalkyl$C_{1-6}$ alkyl, wherein each alkyl, alkenyl, alkynyl, cycloalkyl, aryl and heterocyclyl and groups containing them may be further optionally substituted. In some embodiments, a moiety may be optionally substituted by any subset of optional substituents selected from those described above.

Optional substituents in the case of heterocycles (heterocyclyl and heteroaryl groups) containing N may also include but are not limited to $C_{1-6}$ alkyl i.e. N—$C_{1-3}$ alkyl, more preferably methyl particularly N-methyl.

In one embodiment, cyclic or heterocyclic substituents may form a spirocycloalkyl or spiroheteroalkyl substituent with a carbon in the moiety from which the cyclic or heterocyclic group is substituted. In another embodiment, cyclic or heterocyclic substituents may be bridged.

For optionally substituted "$C_{1-6}$ alkyl", "$C_{2-6}$ alkenyl" and "$C_{2-6}$ alkynyl", the optional substituent or substituents are preferably selected from halo, aryl, heterocyclyl, $C_{3-8}$ cycloalkyl, $C_{1-6}$ alkoxy, hydroxyl, oxo, aryloxy, halo$C_{1-6}$ alkyl, halo$C_{1-6}$alkoxyl and carboxyl. In some embodiments, the optionally substituted "$C_{1-6}$ alkyl", "$C_{2-6}$alkenyl" and "$C_{2-6}$ alkynyl" may be optionally substituted by any subset of optional substituents selected from those described above.

Any of these groups may be further substituted by any of the above-mentioned groups, where appropriate. For example, alkylamino, or dialkylamino, $C_{1-6}$ alkoxy, etc.

Examples of the compounds of the present invention are given below in Table 1.

TABLE 1

Examples of compounds of the present invention.

| Number | Structure |
|---|---|
| 15 (ZH2-102) | 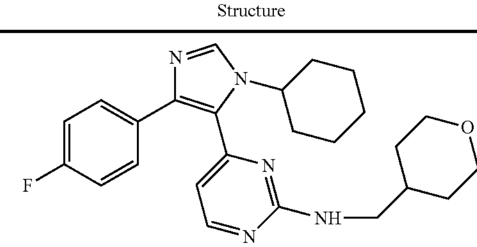 |
| 19 (ZH2-130) | 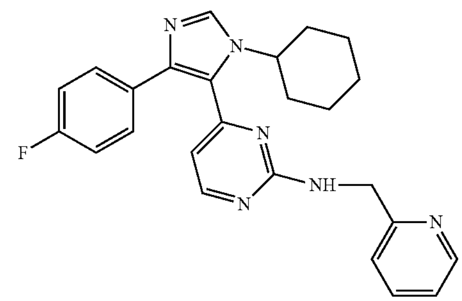 [SMILES: Fc1ccc(-c2ncn(C3CCCCC3)c2-c2ccnc(NCc3ccccn3)n2)cc1] |
| 25 (ZH2-66) | 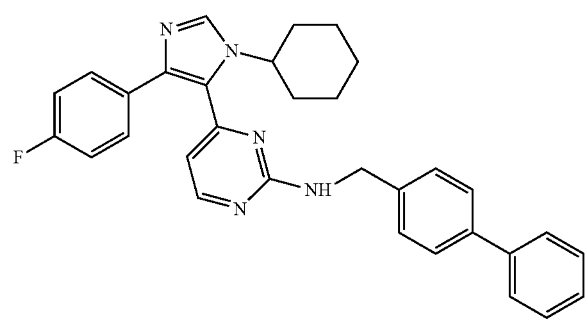 [SMILES: Fc1ccc(-c2ncn(C3CCCCC3)c2-c2ccnc(NCc3ccc(-c4ccccc4)cc3)n2)cc1] |
| 27 (ZH2-86) | 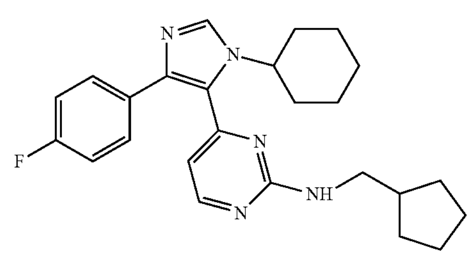 [SMILES: Fc1ccc(-c2ncn(C3CCCCC3)c2-c2ccnc(NCC3CCCC3)n2)cc1] |

TABLE 1-continued

Examples of compounds of the present invention.

| Number | Structure |
|---|---|
| 28 (ZH2-98) | 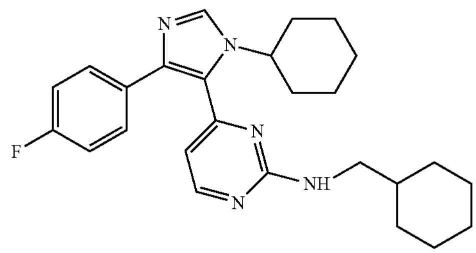 [SMILES: Fc1ccc(-c2ncn(C3CCCCC3)c2-c2ccnc(NCC3CCCCC3)n2)cc1] |
| 32 (ZH3-74) | 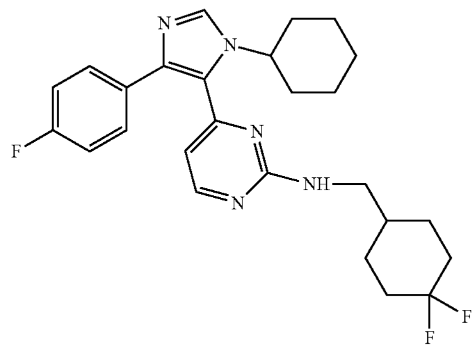 [SMILES: Fc1ccc(-c2ncn(C3CCCCC3)c2-c2ccnc(NCC3CCC(F)(F)CC3)n2)cc1] |
| 34 (ZH3-90) | 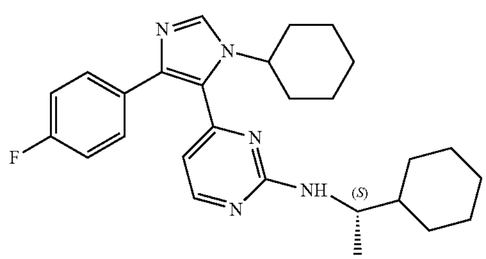 |
| 35 (ZH3-94) | 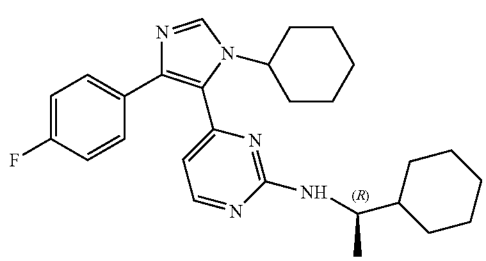 |
| 36 (ZH3-98) | 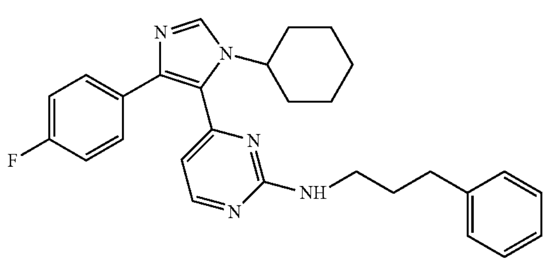 [SMILES: Fc1ccc(-c2ncn(C3CCCCC3)c2-c2ccnc(NCCCc3ccccc3)n2)cc1] |

TABLE 1-continued

Examples of compounds of the present invention.

| Number | Structure |
|---|---|
| 37 | 4-(4-fluorophenyl)-1-(trifluoromethyl)-1H-imidazol-5-yl pyrimidin-2-yl [(1S)-1-cyclohexylethyl]amine |
| 38 | 4-(4-fluorophenyl)-1-(2,2,2-trifluoroethyl)-1H-imidazol-5-yl pyrimidin-2-yl [(1S)-1-cyclohexylethyl]amine |
| 39 | 4-(4-fluorophenyl)-1-(3,3,3-trifluoropropyl)-1H-imidazol-5-yl pyrimidin-2-yl [(1S)-1-cyclohexylethyl]amine |
| 40 | 4-(4-fluorophenyl)-1-(1,1,1,3,3,3-hexafluoropropan-2-yl)-1H-imidazol-5-yl pyrimidin-2-yl [(1S)-1-cyclohexylethyl]amine |
| 41 | 4-(4-fluorophenyl)-1-(trifluoromethyl)-1H-imidazol-5-yl pyrimidin-2-yl [(1R)-1-cyclohexylethyl]amine |
| 42 | 4-(4-fluorophenyl)-1-(2,2,2-trifluoroethyl)-1H-imidazol-5-yl pyrimidin-2-yl [(1R)-1-cyclohexylethyl]amine |

TABLE 1-continued

Examples of compounds of the present invention.

| Number | Structure |
|---|---|
| 43 | 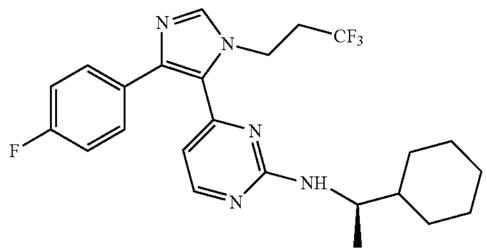 [SMILES: C[C@@H](Nc1nccc(-c2c(-c3ccc(F)cc3)ncn2CCC(F)(F)F)n1)C1CCCCC1] |
| 44 | 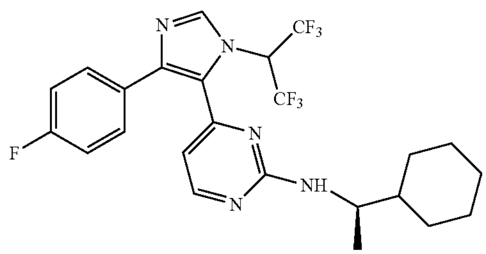 [SMILES: C[C@@H](Nc1nccc(-c2c(-c3ccc(F)cc3)ncn2C(C(F)(F)F)C(F)(F)F)n1)C1CCCCC1] |
| 45 | 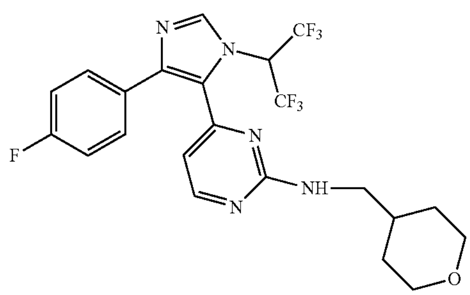 [SMILES: Fc1ccc(-c2ncn(C(C(F)(F)F)C(F)(F)F)c2-c2ccnc(NCC3CCOCC3)n2)cc1] |
| 46 | 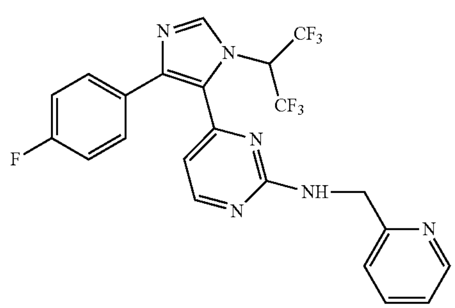 [SMILES: Fc1ccc(-c2ncn(C(C(F)(F)F)C(F)(F)F)c2-c2ccnc(NCc3ccccn3)n2)cc1] |
| 47 | 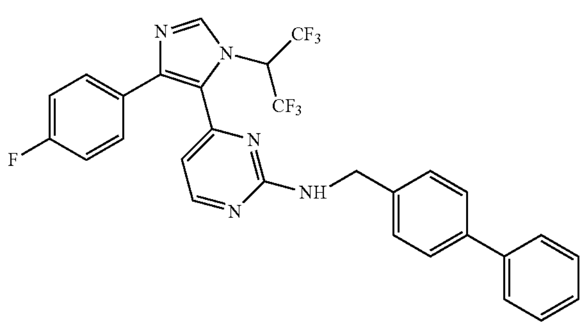 [SMILES: Fc1ccc(-c2ncn(C(C(F)(F)F)C(F)(F)F)c2-c2ccnc(NCc3ccc(-c4ccccc4)cc3)n2)cc1] |

TABLE 1-continued
Examples of compounds of the present invention.
| Number | Structure |
|---|---|
| 48 | 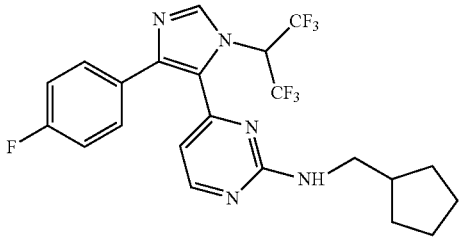 [SMILES: Fc1ccc(-c2ncn(C(C(F)(F)F)C(F)(F)F)c2-c2ccnc(NCC3CCCC3)n2)cc1] |
| 49 | 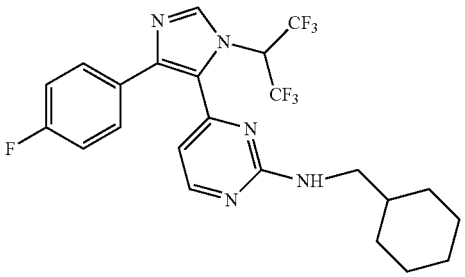 [SMILES: Fc1ccc(-c2ncn(C(C(F)(F)F)C(F)(F)F)c2-c2ccnc(NCC3CCCCC3)n2)cc1] |
| 50 | 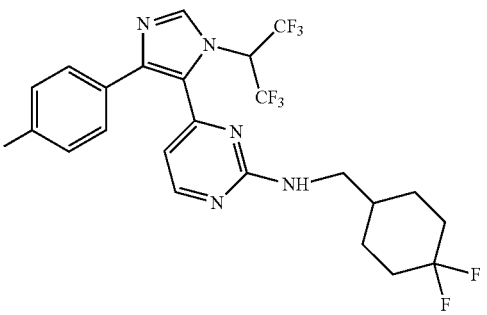 |
| 51 | 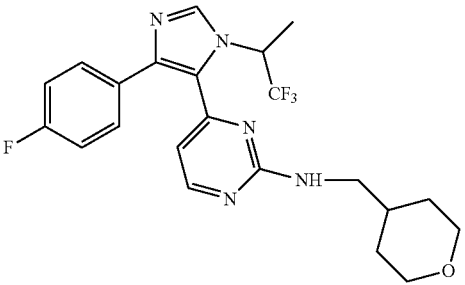 [SMILES: CC(n1cnc(-c2ccc(F)cc2)c1-c1ccnc(NCC2CCOCC2)n1)C(F)(F)F] |
| 52 | 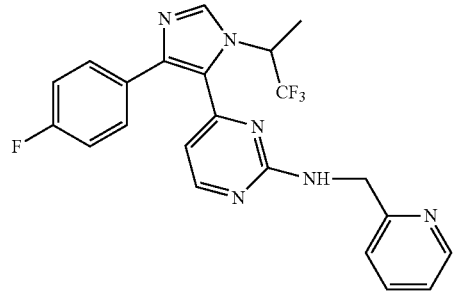 [SMILES: CC(n1cnc(-c2ccc(F)cc2)c1-c1ccnc(NCc2ccccn2)n1)C(F)(F)F] |

TABLE 1-continued

Examples of compounds of the present invention.

| Number | Structure |
|---|---|
| 53 | 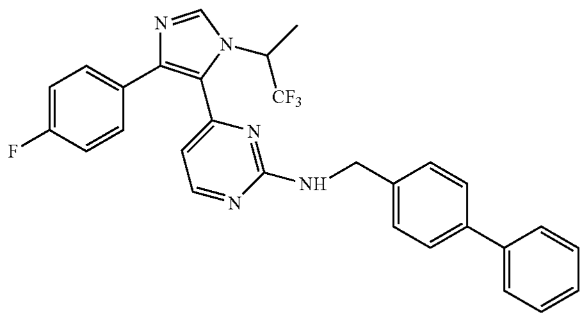 [SMILES: CC(n1cnc(-c2ccc(F)cc2)c1-c1ccnc(NCc2ccc(-c3ccccc3)cc2)n1)C(F)(F)F] |
| 54 | 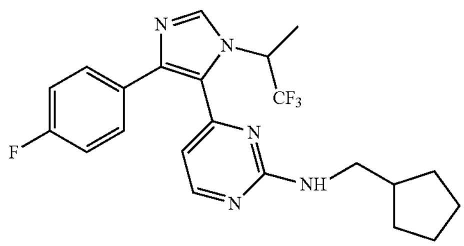 [SMILES: CC(n1cnc(-c2ccc(F)cc2)c1-c1ccnc(NCC2CCCC2)n1)C(F)(F)F] |
| 55 | 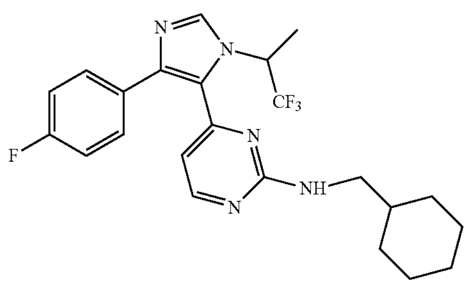 [SMILES: CC(n1cnc(-c2ccc(F)cc2)c1-c1ccnc(NCC2CCCCC2)n1)C(F)(F)F] |
| 56 | 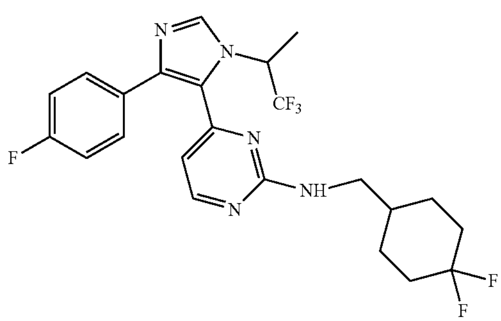 [SMILES: CC(n1cnc(-c2ccc(F)cc2)c1-c1ccnc(NCC2CCC(F)(F)CC2)n1)C(F)(F)F] |
| 57 | 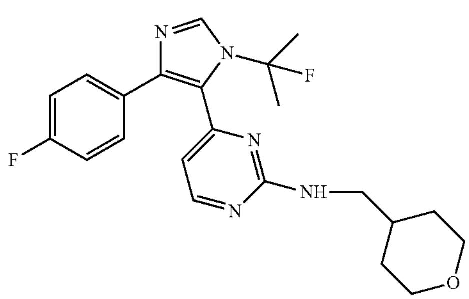 [SMILES: CC(C)(F)n1cnc(-c2ccc(F)cc2)c1-c1ccnc(NCC2CCOCC2)n1] |

TABLE 1-continued

Examples of compounds of the present invention.

| Number | Structure |
|---|---|
| 58 | 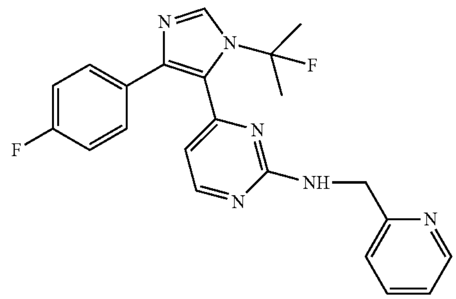 [SMILES: CC(C)(F)n1cnc(-c2ccc(F)cc2)c1-c1ccnc(NCc2ccccn2)n1] |
| 59 | 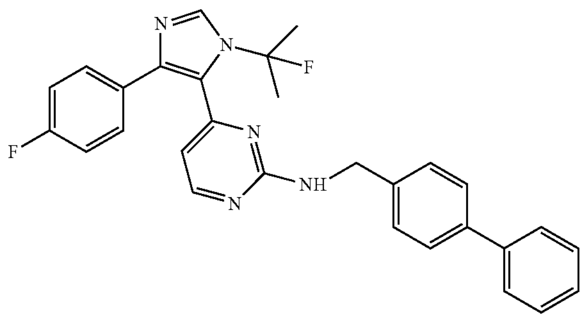 [SMILES: CC(C)(F)n1cnc(-c2ccc(F)cc2)c1-c1ccnc(NCc2ccc(-c3ccccc3)cc2)n1] |
| 60 | 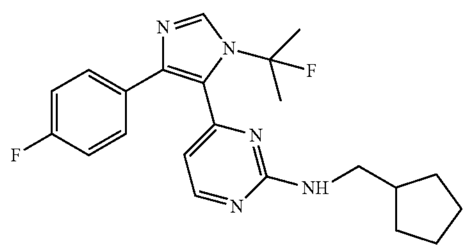 [SMILES: CC(C)(F)n1cnc(-c2ccc(F)cc2)c1-c1ccnc(NCC2CCCC2)n1] |
| 61 | 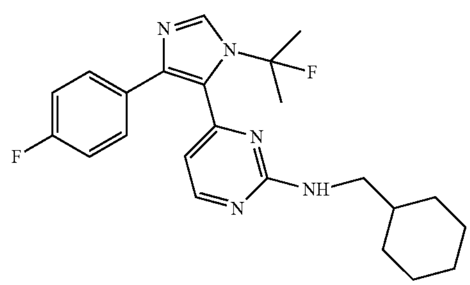 [SMILES: CC(C)(F)n1cnc(-c2ccc(F)cc2)c1-c1ccnc(NCC2CCCCC2)n1] |
| 62 | 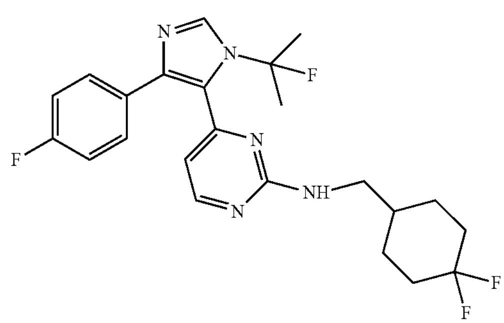 [SMILES: CC(C)(F)n1cnc(-c2ccc(F)cc2)c1-c1ccnc(NCC2CCC(F)(F)CC2)n1] |

TABLE 1-continued
Examples of compounds of the present invention.
| Number | Structure |
|---|---|
| 63 | 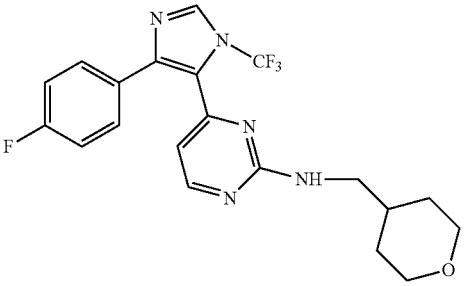 [SMILES: Fc1ccc(-c2ncn(C(F)(F)F)c2-c2ccnc(NCC3CCOCC3)n2)cc1] |
| 64 | 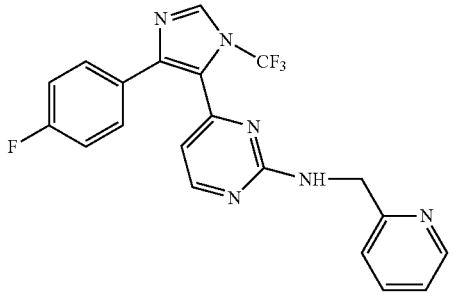 [SMILES: Fc1ccc(-c2ncn(C(F)(F)F)c2-c2ccnc(NCc3ccccn3)n2)cc1] |
| 65 | 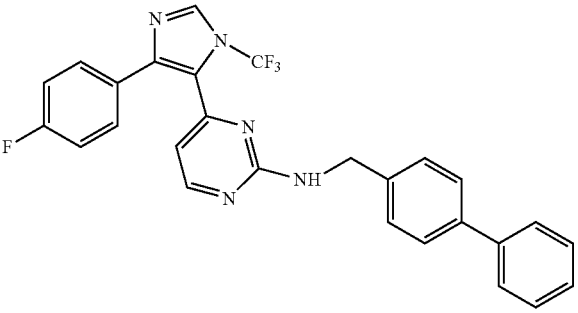 [SMILES: Fc1ccc(-c2ncn(C(F)(F)F)c2-c2ccnc(NCc3ccc(-c4ccccc4)cc3)n2)cc1] |
| 66 | 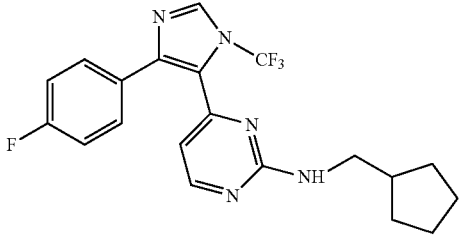 |
| 67 | 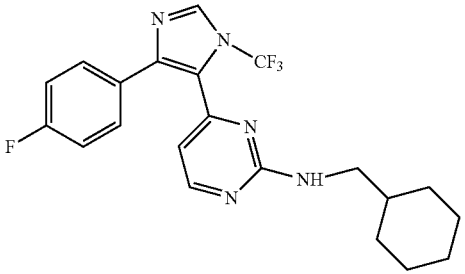 [SMILES: Fc1ccc(-c2ncn(C(F)(F)F)c2-c2ccnc(NCC3CCCCC3)n2)cc1] |

TABLE 1-continued

Examples of compounds of the present invention.

| Number | Structure |
|---|---|
| 68 | 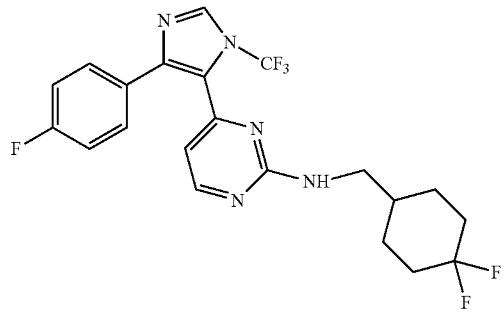 [SMILES: Fc1ccc(-c2ncn(C(F)(F)F)c2-c2ccnc(NCC3CCC(F)(F)CC3)n2)cc1] |
| 69 | 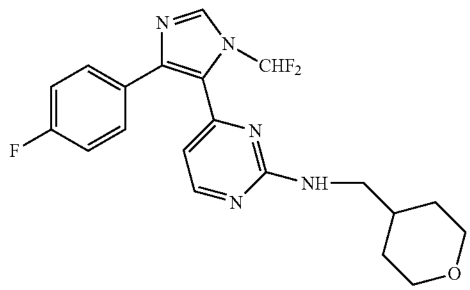 [SMILES: Fc1ccc(-c2ncn(C(F)F)c2-c2ccnc(NCC3CCOCC3)n2)cc1] |
| 70 | 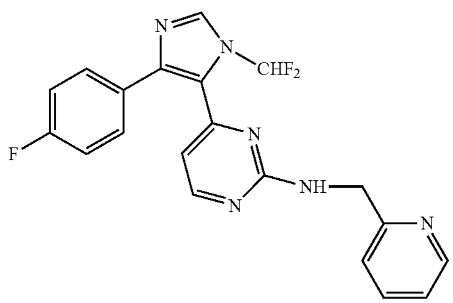 [SMILES: Fc1ccc(-c2ncn(C(F)F)c2-c2ccnc(NCc3ccccn3)n2)cc1] |
| 71 | 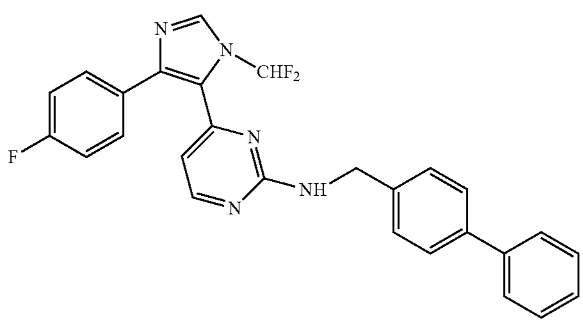 [SMILES: Fc1ccc(-c2ncn(C(F)F)c2-c2ccnc(NCc3ccc(-c4ccccc4)cc3)n2)cc1] |
| 72 | 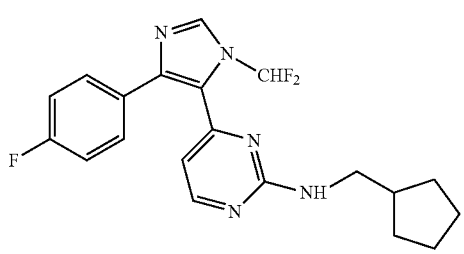 |

TABLE 1-continued
Examples of compounds of the present invention.
| Number | Structure |
|--------|-----------|
| 73 | 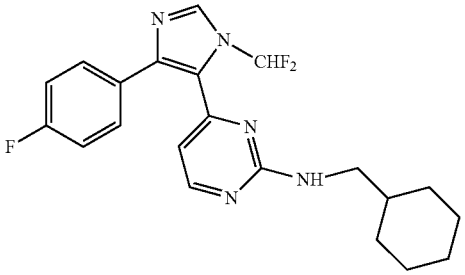 [SMILES: Fc1ccc(-c2ncn(C(F)F)c2-c2ccnc(NCC3CCCCC3)n2)cc1] |
| 74 | 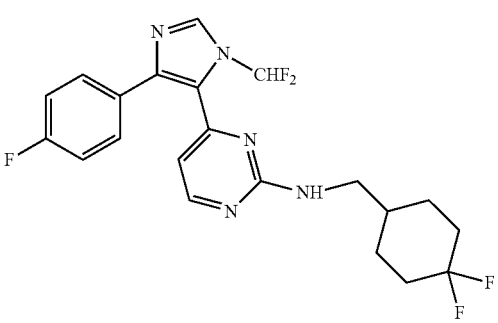 [SMILES: Fc1ccc(-c2ncn(C(F)F)c2-c2ccnc(NCC3CCC(F)(F)CC3)n2)cc1] |
| 75 | 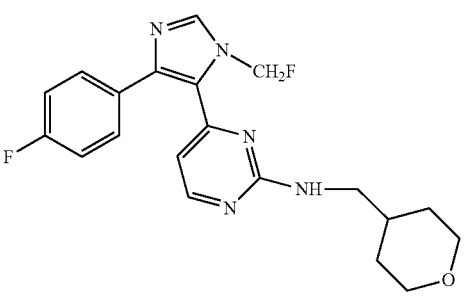 |
| 76 | 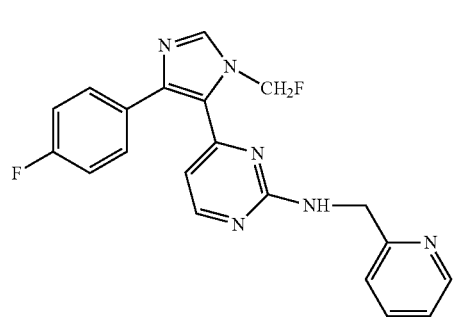 |
| 77 | 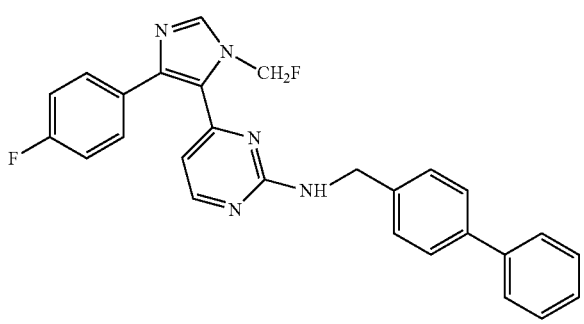 |

TABLE 1-continued

Examples of compounds of the present invention.

| Number | Structure |
|---|---|
| 78 | (structure) |
| 79 | (structure) |
| 80 | (structure) |
| 81 | (structure) |
| 82 | (structure) |

TABLE 1-continued
Examples of compounds of the present invention.
| Number | Structure |
|---|---|
| 83 | 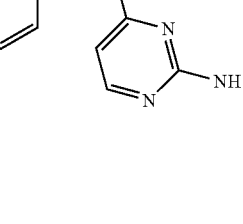 |
| 84 | 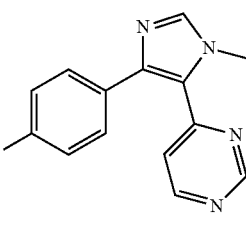 |
| 85 | 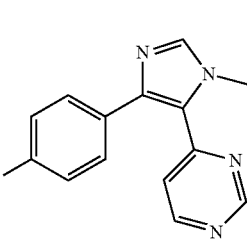 |
| 86 | 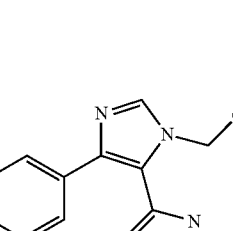 |
| 87 | 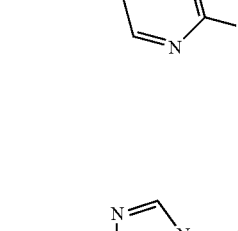 |

TABLE 1-continued

Examples of compounds of the present invention.

| Number | Structure |
|---|---|
| 88 | 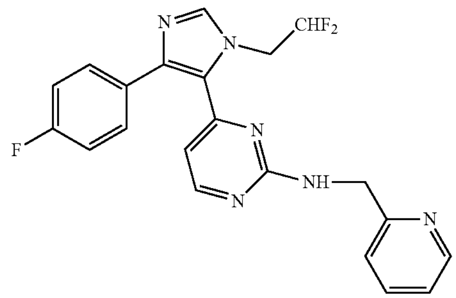 |
| 89 | 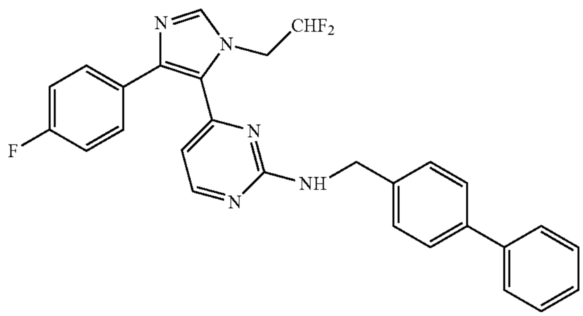 [SMILES: Fc1ccc(-c2ncn(CC(F)(F)F)c2-c2ccnc(NCc3ccc(-c4ccccc4)cc3)n2)cc1] |
| 90 | 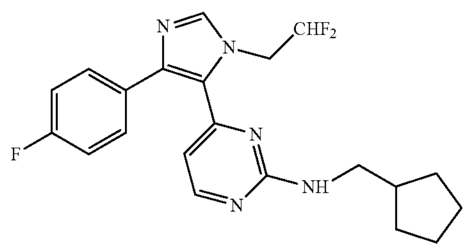 |
| 91 | 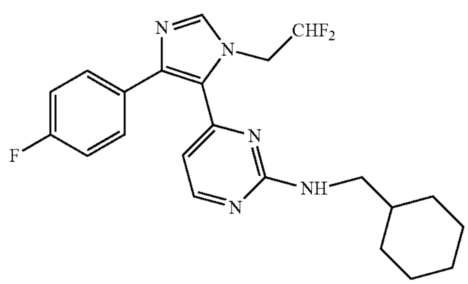 [SMILES: Fc1ccc(-c2ncn(CC(F)(F)F)c2-c2ccnc(NCC3CCCCC3)n2)cc1] |
| 92 | 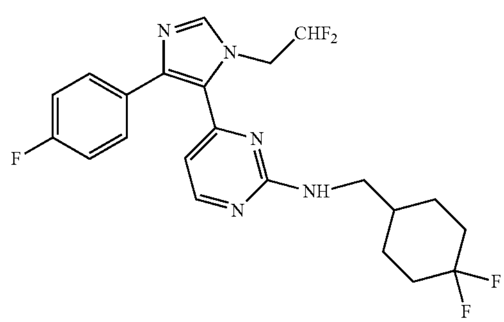 [SMILES: Fc1ccc(-c2ncn(CC(F)F)c2-c2ccnc(NCC3CCC(F)(F)CC3)n2)cc1] |

TABLE 1-continued
Examples of compounds of the present invention.
| Number | Structure |
|---|---|
| 93 | 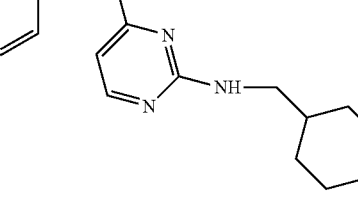 |
| 94 | 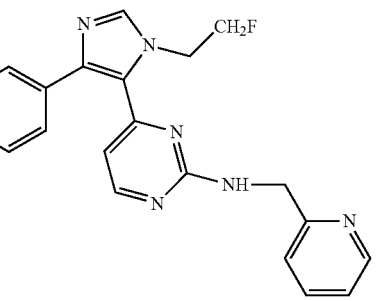 |
| 95 | 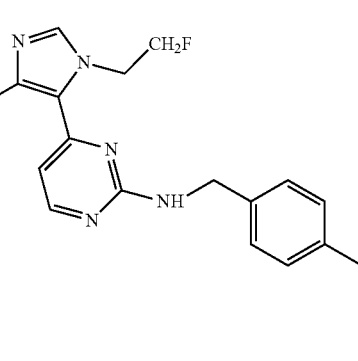 |
| 96 | 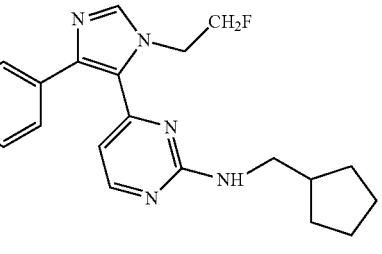 |
| 97 | 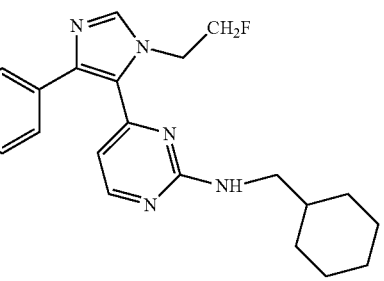 |

TABLE 1-continued

Examples of compounds of the present invention.

| Number | Structure |
|---|---|
| 98 | (structure) |
| 99 | (structure) |
| 100 | (structure) |
| 101 | (structure) |
| 102 | (structure) |

TABLE 1-continued

Examples of compounds of the present invention.

| Number | Structure |
|---|---|
| 103 | 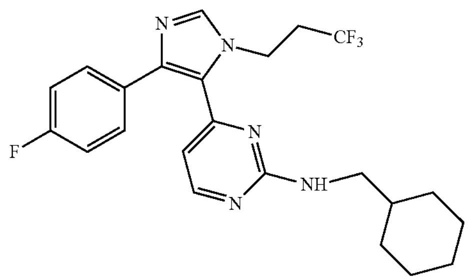 [SMILES: Fc1ccc(-c2ncn(CCC(F)(F)F)c2-c2ccnc(NCC3CCCCC3)n2)cc1] |
| 104 | 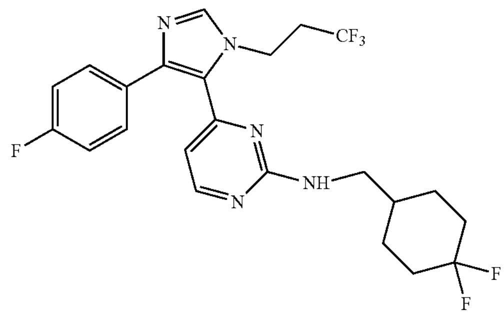 [SMILES: Fc1ccc(-c2ncn(CCC(F)(F)F)c2-c2ccnc(NCC3CCC(F)(F)CC3)n2)cc1] |
| 105 | 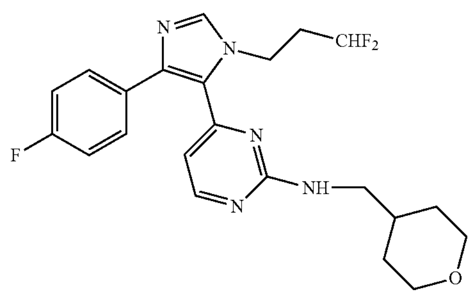 |
| 106 | 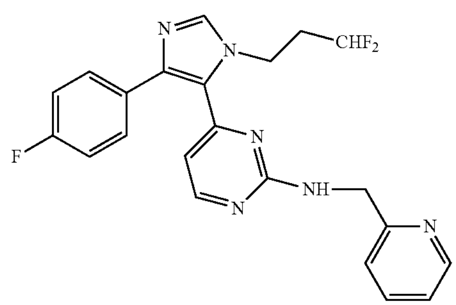 |
| 107 | 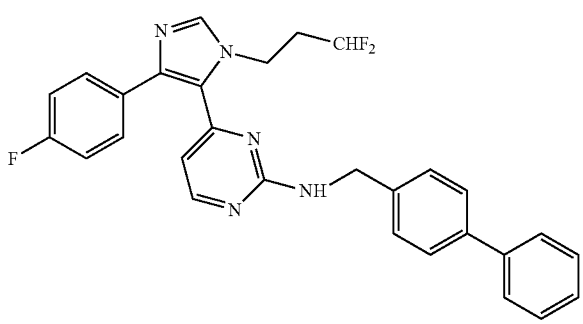 [SMILES: Fc1ccc(-c2ncn(CCC(F)F)c2-c2ccnc(NCc3ccc(-c4ccccc4)cc3)n2)cc1] |

TABLE 1-continued
Examples of compounds of the present invention.
| Number | Structure |
|---|---|
| 108 | 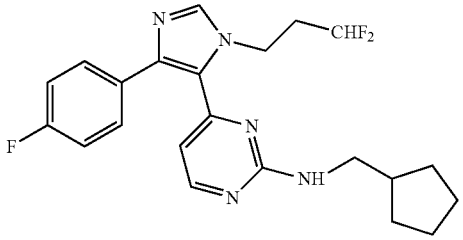 [SMILES: Fc1ccc(-c2ncn(CCC(F)F)c2-c2ccnc(NCC3CCCC3)n2)cc1] |
| 109 | 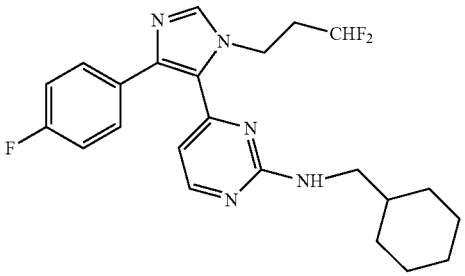 [SMILES: Fc1ccc(-c2ncn(CCC(F)F)c2-c2ccnc(NCC3CCCCC3)n2)cc1] |
| 110 | 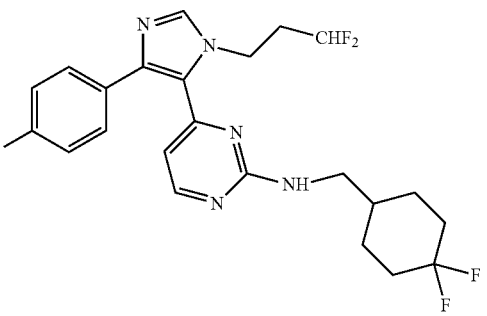 |
| 111 | 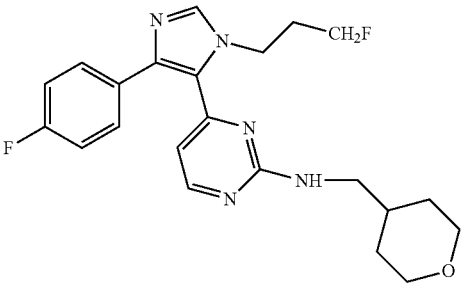 |
| 112 | 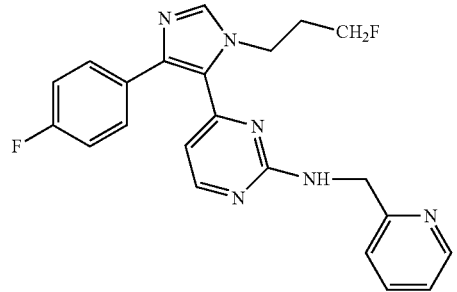 |

TABLE 1-continued

Examples of compounds of the present invention.

| Number | Structure |
|---|---|
| 113 | 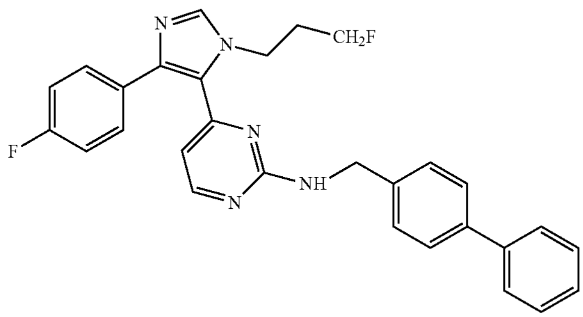 |
| 114 | 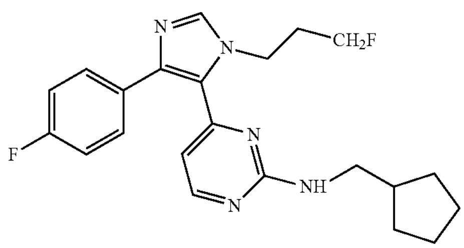 |
| 115 | 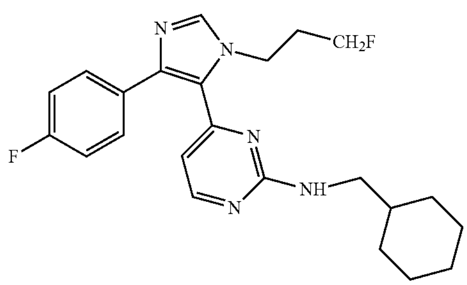 |
| 116 | 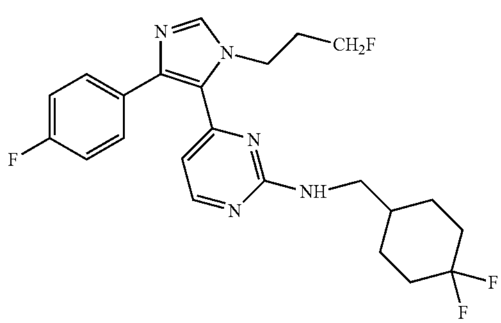 |
| 117 | 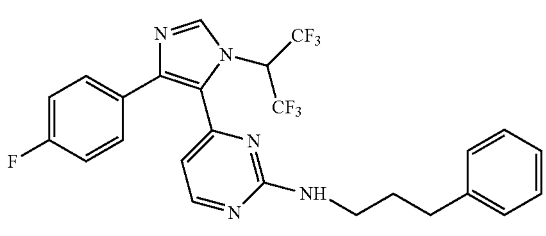 [SMILES: Fc1ccc(-c2ncn(C(C(F)(F)F)C(F)(F)F)c2-c2ccnc(NCCCc3ccccc3)n2)cc1] |

TABLE 1-continued
Examples of compounds of the present invention.
| Number | Structure |
|---|---|
| 118 | 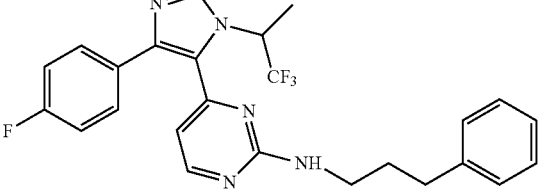 |
| 119 | 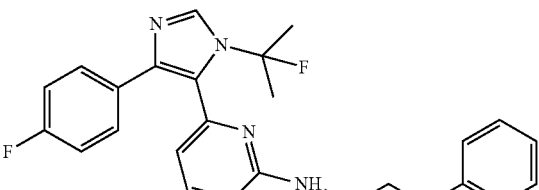 |
| 120 | 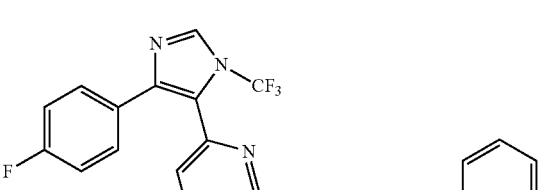 |
| 121 | 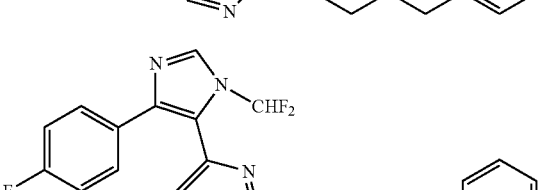 |
| 122 | 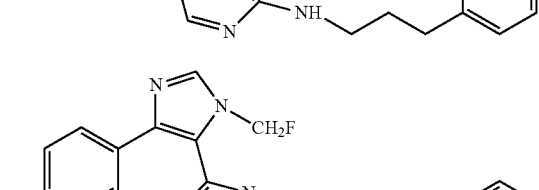 |
| 123 (ZH4-166) | 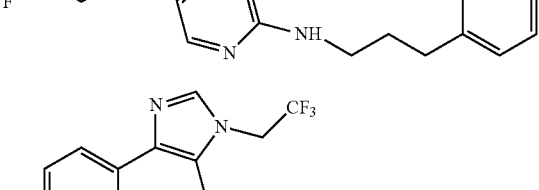 |
| 124 | 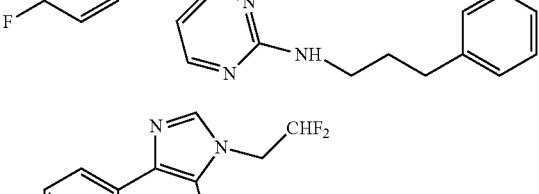 |

TABLE 1-continued

Examples of compounds of the present invention.

| Number | Structure |
|---|---|
| 125 | 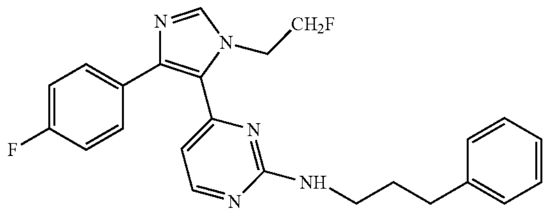 [SMILES: Fc1ccc(-c2ncn(CC(F)F)c2-c2ccnc(NCCCc3ccccc3)n2)cc1] |
| 126 | 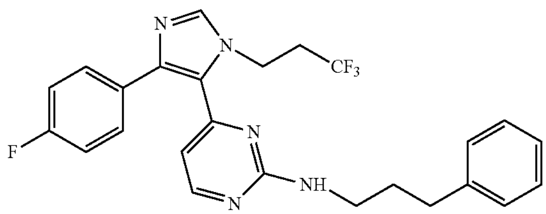 [SMILES: Fc1ccc(-c2ncn(CCC(F)(F)F)c2-c2ccnc(NCCCc3ccccc3)n2)cc1] |
| 127 | 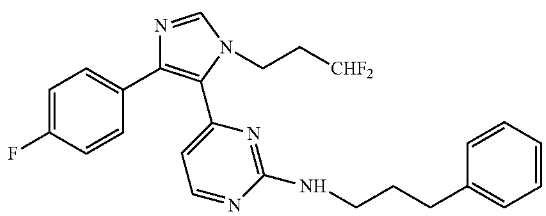 |
| 128 | 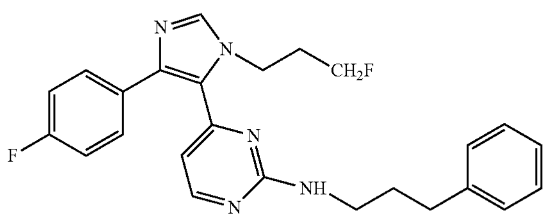 |
| 135 | 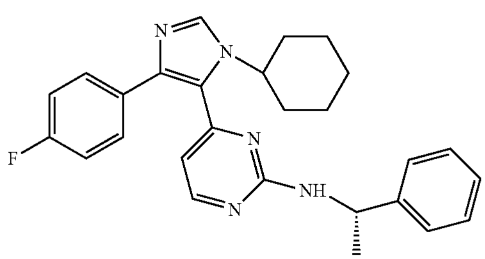 [SMILES: C[C@H](Nc1nccc(-c2c(-c3ccc(F)cc3)ncn2C2CCCCC2)n1)c1ccccc1] |
| 136 | 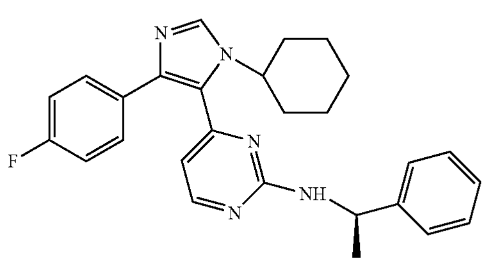 [SMILES: C[C@@H](Nc1nccc(-c2c(-c3ccc(F)cc3)ncn2C2CCCCC2)n1)c1ccccc1] |

TABLE 1-continued

Examples of compounds of the present invention.

| Number | Structure |
|---|---|
| 137 | 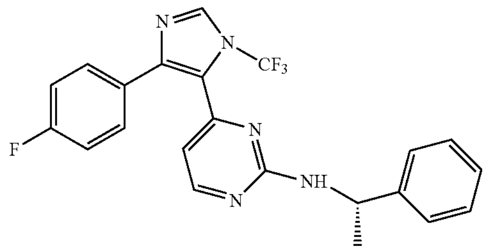 [SMILES: C[C@H](Nc1nccc(-c2c(-c3ccc(F)cc3)ncn2C(F)(F)F)n1)c1ccccc1] |
| 138 | 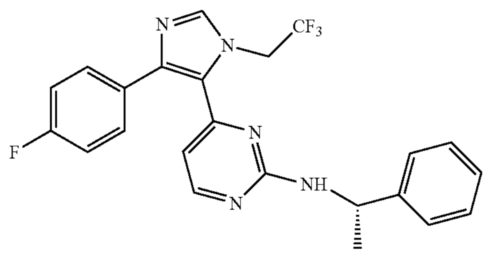 [SMILES: C[C@H](Nc1nccc(-c2c(-c3ccc(F)cc3)ncn2CC(F)(F)F)n1)c1ccccc1] |
| 139 | 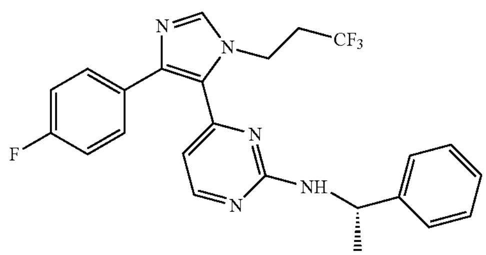 [SMILES: C[C@H](Nc1nccc(-c2c(-c3ccc(F)cc3)ncn2CCC(F)(F)F)n1)c1ccccc1] |
| 140 | 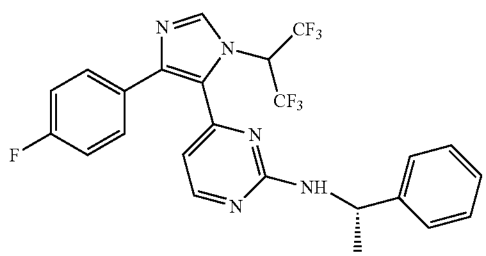 [SMILES: C[C@H](Nc1nccc(-c2c(-c3ccc(F)cc3)ncn2C(C(F)(F)F)C(F)(F)F)n1)c1ccccc1] |
| 141 | 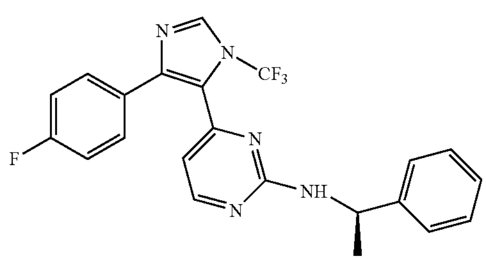 [SMILES: C[C@@H](Nc1nccc(-c2c(-c3ccc(F)cc3)ncn2C(F)(F)F)n1)c1ccccc1] |
| 142 | 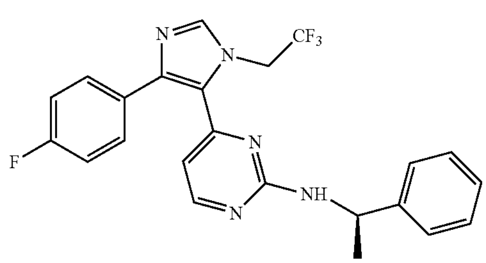 [SMILES: C[C@@H](Nc1nccc(-c2c(-c3ccc(F)cc3)ncn2CC(F)(F)F)n1)c1ccccc1] |

TABLE 1-continued

Examples of compounds of the present invention.

| Number | Structure |
|---|---|
| 143 | (structure) |
| 144 | (structure) |
| 145 | (structure) |
| 146 | (structure) |
| 147 | (structure) |
| 148 | (structure) |

TABLE 1-continued

Examples of compounds of the present invention.

| Number | Structure |
|---|---|
| 149 | 4-(4-fluorophenyl)-imidazole-CHF₂ / pyrimidine-NH-(S)-CH(CH₃)-phenyl |
| 150 | 4-(4-fluorophenyl)-imidazole-CHF₂ / pyrimidine-NH-(R)-CH(CH₃)-phenyl |
| 151 | 4-(4-fluorophenyl)-imidazole-CH₂F / pyrimidine-NH-(S)-CH(CH₃)-phenyl |
| 152 | 4-(4-fluorophenyl)-imidazole-CH₂F / pyrimidine-NH-(R)-CH(CH₃)-phenyl |
| 153 | 4-(4-fluorophenyl)-imidazole-CH₂CF₃ / pyrimidine-NH-(S)-CH(CH₃)-phenyl |
| 154 | 4-(4-fluorophenyl)-imidazole-CH₂CF₃ / pyrimidine-NH-(R)-CH(CH₃)-phenyl |

TABLE 1-continued
Examples of compounds of the present invention.
| Number | Structure |
|---|---|
| 155 | 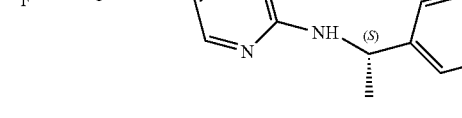 |
| 156 | 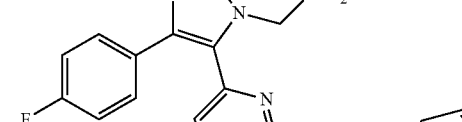 |
| 157 | 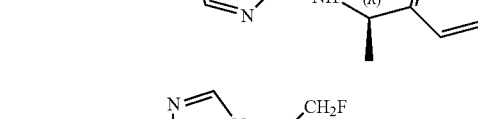 |
| 158 | 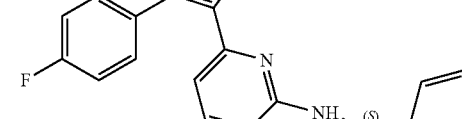 |
| 159 | 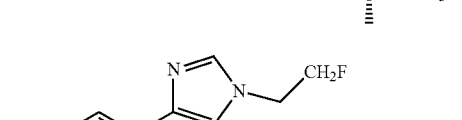 |
| 160 | 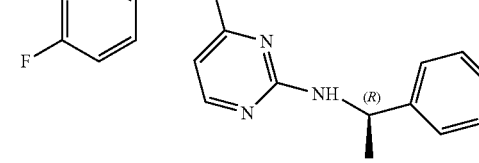 |

TABLE 1-continued

Examples of compounds of the present invention.

| Number | Structure |
|---|---|
| 161 | (imidazole-pyrimidine structure with 4-fluorophenyl, CHF₂, and (S)-NH-CH(CH₃)-phenyl substituents) |
| 162 | (imidazole-pyrimidine structure with 4-fluorophenyl, CHF₂, and (R)-NH-CH(CH₃)-phenyl substituents) |
| 163 | (imidazole-pyrimidine structure with 4-fluorophenyl, CH₂F, and (S)-NH-CH(CH₃)-phenyl substituents) |
| 164 | (imidazole-pyrimidine structure with 4-fluorophenyl, CH₂F, and (R)-NH-CH(CH₃)-phenyl substituents) |

The salts of the compounds of formula (I) are preferably pharmaceutically acceptable, but it will be appreciated that non-pharmaceutically acceptable salts also fall within the scope of the present disclosure, since these may be useful as intermediates in the preparation of pharmaceutically acceptable salts.

The term "pharmaceutically acceptable" may be used to describe any pharmaceutically acceptable salt, solvate, tautomer, N-oxide, stereoisomer polymorph and/or prodrug, or any other compound which upon administration to a subject, is capable of providing (directly or indirectly) a compound of formula (I), or an active metabolite or residue thereof and typically that is not deleterious to the subject.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic, valeric and xinafoic acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "*Handbook of Pharmaceutical salts*" P. H. Stahl, C. G. Wermuth, 1st edition, 2002, Wiley-VCH.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

A "prodrug" is a compound that may not fully satisfy the structural requirements of the compounds provided herein, but is modified in vivo, following administration to a subject or patient, to produce a compound of formula (I) provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

Prodrugs include compounds wherein an amino acid residue, or a polypeptide chain of two or more (e.g., two, three or four) amino acid residues which are covalently joined to free amino and/or amido groups of compounds of formula (I). The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-am inobutyric acid, citrulline, homocysteine, homoserine, ornithine and methionine sulfone. Prodrugs also include compounds wherein carbonates, carbamates, amides and alkyl esters which are covalently bonded to the above substituents of formula (I) through the carbonyl carbon prodrug sidechain. Prodrugs can include covalent irreversible and reversible inhibitors.

In the case of compounds that are solids, it will be understood by those skilled in the art that the inventive compounds, agents and salts may exist in different crystalline or polymorphic forms, all of which are intended to be within the scope of the present invention and specified formulae.

The invention includes all crystalline forms of a compound of Formula (I) including anhydrous crystalline forms, hydrates, solvates and mixed solvates. If any of these crystalline forms demonstrates polymorphism, all polymorphs are within the scope of this invention.

Formula (I) is intended to cover, where applicable, solvated as well as unsolvated forms of the compounds. Thus, Formula (I) includes compounds having the indicated structures, including the hydrated or solvated forms, as well as the non-hydrated and non-solvated forms.

The compounds of Formula (I) or salts, tautomers, N-oxides, polymorphs or prodrugs thereof may be provided in the form of solvates. Solvates contain either stoichiometric or non-stoichiometric amounts of a solvent, and may be formed during the process of crystallization with pharmaceutically acceptable solvents such as water, alcohols such as methanol, ethanol or isopropyl alcohol, DMSO, acetonitrile, dimethyl formamide (DMF), acetic acid, and the like with the solvate forming part of the crystal lattice by either non-covalent binding or by occupying a hole in the crystal lattice. Hydrates are formed when the solvent is water, alcoholates are formed when the solvent is alcohol. Solvates of the compounds of the present invention can be conveniently prepared or formed during the processes described herein. In general, the solvated forms are considered equivalent to the unsolvated forms for the purposes of the invention.

The compound of Formula (I) or salts, tautomers, N-oxides, solvates and/or prodrugs thereof that form crystalline solids may demonstrate polymorphism. All polymorphic forms of the compounds, salts, tautomers, N-oxides, solvates and/or prodrugs are within the scope of the invention.

The compound of Formula (I) may demonstrate tautomerism. Tautomers are two interchangeable forms of a molecule that typically exist within an equilibrium. Any tautomers of the compounds of Formula (I) are to be understood as being within the scope of the invention.

The compound of Formula (I) may contain one or more stereocentres. All stereoisomers of the compounds of formula (I) are within the scope of the invention. Stereoisomers include enantiomers, diastereomers, geometric isomers (E and Z olephinic forms and cis and trans substitution patterns) and atropisomers. In some embodiments, the compound is a stereoisomerically enriched form of the compound of formula (I) at any stereocentre. The compound may be enriched in one stereoisomer over another by at least about 60, 70, 80, 90, 95, 98 or 99%.

The compound of Formula (I) or its salts, tautomers, solvates, N-oxides, and/or stereoisomers, may be isotopically enriched with one or more of the isotopes of the atoms present in the compound. For example, the compound may be enriched with one or more of the following minor isotopes: $^2H$, $^3H$, $^{13}C$, $^{14}C$, $^{15}N$ and/or $^{17}O$. An isotope may be considered enriched when its abundance is greater than its natural abundance.

In some embodiments, the compounds of formula (I) or a salt, solvate, N-oxide, tautomer, stereoisomer, polymorph and/or prodrug thereof have a $pIC_{50}$ of at least 7. The inhibitory activity can be determined using a kinase assay. Such assays are well-known to a person skilled in the art, and an example of a suitable assay is that described in the Examples.

In yet another aspect, there is provided a composition comprising a compound according to formula (I) or a salt, solvate, N-oxide, tautomer, stereoisomer, polymorph and/or prodrug thereof, and a pharmaceutically acceptable excipient.

An appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5, or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. The amount of a compound of the present invention in the composition will also depend upon the particular compound in the composition.

In the case of inhaled products, the typical inhalation dose is less than with other forms of dosing starting at 1 microgram and rising to 1000 microgram for a single puff. In a preferred form, the dose ranges from 25 microgram to 250 microgram per puff. In another preferred form, the dosage ranges from 500 to 1000 micrograms per puff. In another form, the dosage is selected from the group consisting of 1, 2.5, 10.0, 25.0, 50.0, 75.0, 100.0, 150.0, 200.0, 250.0, 300.0, 400.0, 500.0, 600.0, 750.0, 800.0, 900.0, and 1000.0 micrograms per puff or any range in between and including two of these values. The medication may be one puff per day or increase up to two puffs four times a day.

The pharmaceutical composition may further comprise other therapeutically active compounds which are usually applied in the treatment of the disclosed disorders or conditions. Selection of the appropriate agents for use in combination therapy may be made by one of ordinary skill in the art, according to conventional pharmaceutical principles. The combination of therapeutic agents may act synergistically to effect the treatment or prevention of the various disorders or conditions disclosed herein. Using this approach, one may be able to achieve therapeutic efficacy with lower dosages of each agent, thus reducing the potential for adverse side effects.

Compounds and compositions of the invention may be formulated for any appropriate route of administration including, for example, topical (for example, transdermal or ocular), pulmonary, oral, buccal, nasal, vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. Within yet other embodiments, compositions provided herein may be formulated as a lyophilizate.

In a preferred form, the composition is suitable for administration to the respiratory tract. In another form, the composition is suitable for oral administration.

The various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets. The dosage units may further include conventional excipients well-known in pharmaceutical formulation practice, such as binding agents, gellants, fillers, tableting lubricants, disintegrants, surfactants, and colorants; and for suckable or chewable formulations.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Aqueous suspensions contain the active ingredient(s) in admixture with excipients suitable for the manufacture of aqueous suspensions. Such excipients include suspending agents such as sodium carboxymethylcellulose, methylcellulose, hydroxypropylmethylcellulose, sodium alginate, polyvinylpyrrolidone, gum tragacanth and gum acacia, and dispersing or wetting agents such as naturally-occurring phosphatides (for example, lecithin), condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol mono-oleate, or condensation products of ethylene oxide with partial esters derived from fatty acids and hexitol anhydrides such as polyethylene sorbitan monooleate. Aqueous suspensions may also comprise one or more preservatives, for example ethyl or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil such as arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or arachis oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan monoleate, and condensation products of partial esters derived from fatty acids and hexitol with ethylene oxide such as polyoxyethylene sorbitan monoleate. An emulsion may also comprise one or more sweetening and/or flavouring agents.

Syrups and elixirs may be formulated with sweetening agents, such as glycerol, propylene glycol, sorbitol or sucrose. Such formulations may also comprise one or more demulcents, preservatives, flavouring agents and/or colouring agents.

Compositions of the invention may be formulated for local or topical administration, such as for topical application to the skin. Formulations for topical administration typically comprise a topical vehicle combined with active agent(s), with or without additional optional components.

Suitable topical vehicles and additional components are well known in the art, and it will be apparent that the choice of a vehicle will depend on the particular physical form and mode of delivery. Topical vehicles include organic solvents such as alcohols (for example, ethanol, iso-propyl alcohol or glycerine), glycols such as butylene, isoprene or propylene glycol, aliphatic alcohols such as lanolin, mixtures of water and organic solvents and mixtures of organic solvents such as alcohol and glycerine, lipid-based materials such as fatty acids, acylglycerols including oils such as mineral oil, and fats of natural or synthetic origin, phosphoglycerides, sphingolipids and waxes, protein-based materials such as collagen and gelatine, silicone-based materials (both nonvolatile and volatile), and hydrocarbon-based materials such as microsponges and polymer matrices.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form. Solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity. Both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels, and often do not contain emulsifiers. Liquid topical products often contain solvents, emulsifiers, moisturizers, emollients, fragrances, dyes/colorants, preservatives and other active ingredients that increase or enhance the efficacy of the final product.

Emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or nonionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Typical modes of delivery for topical compositions include application using the fingers, application using a physical applicator such as a cloth, tissue, swab, stick or brush, spraying including mist, aerosol or foam spraying, dropper application, sprinkling, soaking, and rinsing. Controlled release vehicles can also be used, and compositions may be formulated for transdermal administration (for example, as a transdermal patch).

Pharmaceutical compositions may be formulated as sustained release formulations such as a capsule that creates a slow release of modulator following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of modulator release. The amount of modulator contained within a sustained release formulation depends upon, for example, the site of implantation, the rate and expected duration of release and the nature of the disorder to be treated or prevented.

A pharmaceutical composition may be formulated as inhaled formulations, including sprays, mists, or aerosols. For example, for administration to the respiratory tract. This may be particularly preferred for treatment of a respiratory disease, a condition of the airway or lung involving fibrosis as described herein. The inhaled formulation may be for application to the upper (including the nasal cavity, pharynx and larynx) and lower respiratory tract (including trachea, bronchi and lungs). For inhalation formulations, the composition or combination provided herein may be delivered via any inhalation methods known to a person skilled in the art. Such inhalation methods and devices include, but are not limited to, metered dose inhalers with propellants such as HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve. Different devices and excipients can be used depending on whether the application is to the upper (including the nasal cavity, pharynx and larynx) or lower respiratory tract (including trachea, bronchi and lungs) and can be determined by those skilled in the art. Further, processes for micronisation and nanoparticle formation for the preparation of compounds described herein for use in an inhaler, such as a dry powder inhaler, are also known by those skilled in the art.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient. Examples of inhalation drug delivery devices are described in Ibrahim et al. Medical Devices: Evidence and Research 2015:8 131-139, are contemplated for use in the present invention.

In another aspect, there is provided a method of treating or preventing a respiratory disease in a subject in need thereof, the method comprising administering to the subject a therapeutically effective amount of a compound of formula (I) or a salt, solvate, N-oxide, tautomer, stereoisomer, polymorph and/or prodrug thereof, thereby treating or preventing a respiratory disease in a subject.

There is further provided a compound of formula (I) or a salt, solvate, N-oxide, tautomer, stereoisomer, polymorph and/or prodrug thereof for use in the treatment or prevention of a respiratory disease in a subject in need thereof.

Use of a compound of formula (I) or a salt, solvate, N-oxide, tautomer, stereoisomer, polymorph and/or prodrug thereof in the preparation of a medicament for the treatment or prevention of a respiratory disease in a subject in need thereof is also described.

As used herein, 'preventing' or 'prevention' is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The terms 'treatment' or 'treating' of a subject includes the application or administration of a compound of the invention to a subject (or application or administration of a compound of the invention to a cell or tissue from a subject) with the purpose of delaying, slowing, stabilizing, curing, healing, alleviating, relieving, altering, remedying, lessening, worsening, ameliorating, improving, or affecting the disease or condition, the symptom of the disease or condition, or the risk of (or susceptibility to) the disease or condition. The term 'treating' refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

The term 'antagonizing' used herein is intended to mean 'decreasing' or 'reducing'. A sufficient period of time can be during one week, or between 1 week to 1 month, or between 1 to 2 months, or 2 months or more. For chronic conditions, the compound of the present invention can be advantageously administered for life time period.

The term 'respiratory' refers to the process by which oxygen is taken into the body and carbon dioxide is discharged, through the bodily system including the nose, throat, larynx, trachea, bronchi and lungs.

The term 'respiratory disease' or 'respiratory condition' refers to any one of several ailments that may involve inflammation and/or tissue remodelling affecting a component of the respiratory system including the upper (including the nasal cavity, pharynx and larynx) and lower respiratory tract (including trachea, bronchi and lungs). Such ailments include pulmonary fibrosis (interstitial lung diseases), rhino sinusitis, influenza, sarcoidosis, bronchial carcinoma (including but not limited to non-small cell and small cell carcinoma of the lung, and lung metastases from tumours of other organs), silicosis, pneumoconiosis, acute lung injury, ventilation-induced lung injury, congenital emphysema, bronchopulmonary dysplasia, bronchiectasis, atelectasis, nasal polyps, asbestosis, mesothelioma, pulmonary eosinophilia, diffuse pulmonary haemorrhage syndromes, bronchiolitis obliterans, alveolar proteinosis, collagen and vascular disorders affecting the lung, and cough. Preferably, the respiratory disease is an obstructive airway disease, such ailments include asthmatic conditions including hay fever, allergen-induced asthma, exercise-induced asthma, pollution-induced asthma, cold-induced asthma, stress-induced asthma and viral-induced-asthma, obesity-related asthma, occupational asthma, thunderstorm-induced asthma, asthma COPD overlap syndrome (ACOS) chronic obstructive pulmonary diseases including chronic bronchitis with normal airflow, chronic bronchitis with airway obstruction (chronic obstructive bronchitis), emphysema, asthmatic bronchitis, and bullous disease, and other pulmonary diseases involving inflammation including cystic fibrosis, pigeon fancier's disease, farmer's lung, acute respiratory distress syndrome, pneumonia of fungal, viral, bacterial, mixed or unknown aetiology, aspiration or inhalation injury, fat embolism in the lung, acidosis inflammation of the lung, acute pulmonary edema, acute mountain sickness, post-cardiac surgery, acute pulmonary hypertension, persistent pulmonary hypertension of the newborn, perinatal aspiration syndrome, hyaline membrane disease, acute pulmonary thromboembolism, heparin-protamine reactions, sepsis, status asthmaticus and hypoxia. The inflammation in the upper and lower respiratory tract may be associated with or caused by viral infection or an allergen. It is expected that the anti-inflammatory activity of the compounds either alone or when co-administered with a glucocorticoid would make them particularly suitable for treatment of these disease or conditions.

The respiratory disease or condition may be associated with or caused by an allergen, such as house dust mite. The respiratory disease or condition may be the result of an allergen-induced inflammation. The present invention finds particular application to allergic disease of the airway or lung and exacerbations of that disease, such as exacerbations resulting from viral infection (e.g. RSV infection).

A symptom of respiratory disease may include cough, excess sputum production, a sense of breathlessness or chest tightness with audible wheeze. Exercise capacity may be quite limited. In asthma the FEV1.0 (forced expiratory volume in one second) as a percentage of that predicted nomographically based on weight, height and age, may be decreased as may the peak expiratory flow rate in a forced expiration. In COPD the FEV1.0 as a ratio of the forced vital capacity (FVC) is typically reduced to less than 0.7. In IPF there is a progressive fall in FVC. The impact of each of these conditions may also be measured by days of lost work/school, disturbed sleep, requirement for bronchodilator drugs, requirement for glucocorticoids including oral glucocorticoids. Further measures of the impact of these conditions include validated health-related quality of life measurements. Medical imaging procedures including but not limited to X-ray, high resolution computed tomography, magnetic resonance imaging, positron emission tomography, ultra sound, optical coherence tomography and fluoroscopy may also be used to assess disease and therapeutic response.

The existence of, improvement in, treatment of or prevention of a respiratory disease may be by any clinically or biochemically relevant method of the subject or a biopsy therefrom. For example, a parameter measured may be the presence or degree of lung function, signs and symptoms of obstruction; exercise tolerance; night time awakenings; days lost to school or work; bronchodilator usage; ICS dose; oral GC usage; need for other medications; need for medical treatment; hospital admission.

As used herein, the term 'asthma' refers to a respiratory disorder characterized by episodic difficulty in breathing brought on by any one or a combination of three primary factors including: 1) bronchospasm (i.e., variable and reversible airway obstruction due to airway muscle contraction), 2) inflammation of the airway lining, and 3) bronchial hyper-responsiveness resulting in excessive mucous in the airways, which may be triggered by exposure to an allergen or combination of allergens (i.e., dust mites and mold), viral or bacterial infection (i.e., common cold virus), environmental pollutants (i.e., chemical fumes or smoke), physical exertion (i.e., during exercise), stress, or inhalation of cold air. The term 'asthmatic condition,' as used herein, refers to the characteristic of an individual to suffer from an attack of asthma upon exposure to any one or a number of asthma triggers for that individual. An individual may be characterized as suffering from, for example, allergen-induced asthma, exercise-induced asthma, pollution-induced asthma, viral-induced asthma, or cold-induced asthma.

The efficacy of a treatment for asthma may be measured by methods well-known in the art, for example, increase in pulmonary function (spirometry), decrease in asthma exacerbations, increase in morning peak expiratory flow rate, decrease in rescue medication use, decrease in daytime and night-time asthma symptoms, increase in asthma-free days, increase in time to asthma exacerbation, and increase in forced expiratory volume in one second (FEV1.0).

The terms 'chronic obstructive pulmonary disease' and 'COPD' as used interchangeably herein refers to a chronic disorder or combination of disorders characterized by reduced maximal expiratory flow and slow forced emptying of the lungs that does not change markedly over several months and is not, or is only minimally, reversible with traditional bronchodilators. Most commonly, COPD is a combination of chronic bronchitis, i.e. the presence of cough and sputum for more than three months for about two consecutive years, and emphysema, i.e. alveolar damage. However, COPD can involve chronic bronchitis with normal airflow, chronic bronchitis with airway obstruction (chronic obstructive bronchitis), emphysema, asthmatic bronchitis, and bullous disease, and combinations thereof. Chronic obstructive pulmonary disease is a condition usually but not exclusively resulting from chronic lung damage induced by exposure to tobacco smoke. Other noxious airborne pollutants, such as indoor cooking exhaust and car exhaust may over the long-term cause or increase the risk of COPD, as does ageing.

The phrase 'a condition of the airway or lung involving fibrosis' or 'a condition of the airway or lung having a fibrotic component' includes any disease or condition where there is the formation or development of excess fibrous connective tissue (fibrosis) in the airway or lung thereby resulting in the development of scarred (fibrotic) tissue. This includes interstitial lung diseases such as pulmonary fibrosis, lung fibrosis or Idiopathic pulmonary fibrosis (IPF). More precisely, pulmonary fibrosis is a chronic disease that causes swelling and scarring of the alveoli and interstitial tissues of the lungs. The scar tissue replaces healthy tissue and causes inflammation. This damage to the lung tissue causes stiffness of the lungs which subsequently makes breathing more and more difficult. Lung fibrosis may result from radiation injury or from exposure to therapeutic agents such as bleomycin.

'Idiopathic pulmonary fibrosis (IPF)' is a specific manifestation of idiopathic interstitial pneumonia (IIP), a type of interstitial lung disease. Interstitial lung disease, also known as diffuse parenchymal lung disease (DPLD), refers to a group of lung diseases affecting the interstitium. Microscopically, lung tissue from IPF patients shows a characteristic set of histological features known as usual interstitial pneumonia (UIP). UIP is therefore the pathologic presentation of IPF.

The existence of, improvement in, treatment of or prevention of a condition of the airway or lung involving fibrosis, particularly pulmonary fibrosis/lung fibrosis or Idiopathic pulmonary fibrosis may be by any clinically or biochemically relevant method of the subject or a biopsy therefrom. For example, the rate of decline in FVC or the appearance of high resolution computed tomographic images of the lung may be useful in diagnosing IPF. Further, a parameter measured may be the presence or degree of fibrosis, the content of collagen, fibronectin, or another extracellular matrix protein, the proliferation rate of the cells or any extracellular matrix components in the cells or transdifferentiation of the cells to myofibroblasts.

In one embodiment, the respiratory disease is selected from asthma, chronic obstructive pulmonary disease, interstitial lung diseases (such as idiopathic pulmonary fibrosis) and other conditions relating to tissue remodelling, primary or secondary lung tumour, hayfever, chronic and acute sinusitis, and chronic and acute viral, fungal and bacterial infections of the respiratory tract.

In one embodiment, the improvement in respiratory function may be selected from a decrease in the level of constriction of the lungs, a decrease in the elastic stiffness of the respiratory system, and/or an increase in the ease with which the respiratory system can be extended. Preferably, the improvement is selected from a decrease in the level of constriction of the lungs, and a decrease in the elastic stiffness of the respiratory system. In yet another aspect, there is provided a composition comprising a compound according to formula (I) or a salt, solvate, N-oxide, tautomer, stereoisomer, polymorph and/or prodrug thereof, and a pharmaceutically acceptable excipient.

The therapeutically effective amount of the formulation depends on the severity of the specific respiratory disease indication (e.g. severe chronic asthma), the patient's clinical history and response, and the discretion of the attending physician. The formulation may be administered to the patient at one time or over a series of treatments. An initial candidate dosage may be administered to a patient and the proper dosage and treatment regimen established by monitoring the progress of this patient using conventional techniques well known to those of ordinary skill in the art. Preferably, the therapeutically effective concentration of the active compound will be in the range 0.1 nM to 100 µM. More preferably the range will be 0.1-10 µM. However, it will be appreciated that delivery by inhalation can result in cells within the airway being exposed for short periods of time to concentrations exceeding those quoted above, for a period of time whilst the drug is being diluted in the airway surface fluid and also being absorbed from the airway and lung surfaces.

In one aspect, the method of treatment of the present invention further comprises administering a concomitant medication for the target disease indication. For example, concomitant asthma medications (for both chronic and acute) that may be used with the method of the present invention include but are not limited to: inhaled and oral steroids (e.g. beclomethasone, budesonide, flunisolide, fluticasone, triamcinolone, mometasone); systemic corticosteroids (e.g. methylprednisolone, prednisolone, prednisone, dexamethasone, and deflazacort); inhaled or oral $\beta_2$-adrenoceptor agonists (e.g. salmeterol, formoterol, bitolterol, pirbuterol, vilanterol, terbutaline, bambuterol and albuterol); cromolyn and nedocromil; anti-allergic opthalmic medications (e.g. dexamethasone); agents that modulate the production and action of transforming growth factor-beta, including pirfenidone and nintedanib; methylxanthines and other phosphodiesterase inhibitors (e.g. theophylline and mepyramine-theophylline acetate, roflumilast); leukotriene modifying agents (e.g. zafirlukast, zileuton, montekulast and pranlukast); anticholinergics (e.g. ipatropium bromide); other therapeutic antibodies of any format (e.g. antibodies directed against interleukin 5, such as mepolizumab, or against IgE, such as omalizumab, those antibodies in monoclonal form, Fab, scFV, multivalent compositions, xenoantibodies etc), natural or engineered antibody mimetics (e.g. anticalin) or natural, engineered or synthetic peptides; thromboxane $A_2$ synthetase inhibitors; thromboxane prostanoid receptor antagonists; other eicosanoid modifiers (e.g. alprostadil vs. $PGE_1$, dinoprostone vs. $PGE_2$, epoprostenol vs. prostacyclin and $PGI_2$ analogues (e.g. $PG_{12}$ beraprost), seratrodast, phosphodiesterase 4 isoenzyme inhibitors, thromboxane $A_2$ synthetase inhibitors (e.g. ozmagrel, dazmegrel or ozagrel); ditec (low dose disodium cromoglycate and fenoterol); platelet activating factor receptor antagonists; antihistamines or histamine antagonists: promethazine, chlorpheniramine, loratadine, cetirazine, azelastine; thromboxane $A_2$ receptor antagonists; bradykinin receptor antagonists (e.g. icatibant); agents that inhibit activated eosinophils and T-cell recruitment (e.g. ketotifen), IL-13 blockers (e.g. soluble IL-13 receptor fragments), IL-4 blockers (e.g. soluble IL-4 receptor fragments); ligands that bind and block the activity of IL-13 or IL-4, and xanthine derivatives (e.g. pentoxifylline); chemokine receptor antagonists and antagonists of the CRTH2 receptor.

In certain embodiments, the method of treatment of the present invention includes the concomitant provision to the subject of inhibitory RNA molecules (RNA interference molecules), for the purpose of reducing, inhibiting or preventing the expression of genes which encode target proteins. For example, the inhibitory RNA molecules may be used for reducing or inhibiting the expression of one or more of: proteins associated with pathogens (viral, bacterial, fungal) or mammalian cells, including but not limited to casein kinase 1 isoforms and other components of the CLOCK regulatory network (eg ARNT1, period 1-3) and other proteins that contribute to the inflammatory response in the respiratory system such as interleukin-5 and the NALP inflammasome.

The skilled person will be familiar with various means for utilising inhibitory RNA molecules for the purpose of interfering with gene expression in the subject. For example, the inhibitory RNA molecules may be any one of: short interfering RNA (siRNA), microRNA mimetic (miRNA), short hairpin RNA (shRNA) or long double stranded RNA (long dsRNA) molecules. The inhibitory RNA molecule may be administered directly to the subject requiring treatment (for example by inhalation, intratracheal, oral or nasal administration or by parenteral administration), or alternatively, be formed in the subject receiving treatment, following the administration of a polynucleotide (vector) construct which encodes a double stranded RNA (dsRNA) molecule which is capable of forming an inhibitory RNA molecule. The skilled person will also be familiar with various methods known in the art for formulating inhibitory RNA molecules for administration (for example, in liposomes, nanoparticles and the like). The invention also includes the administration of an inhibitor of casein kinase 1 and a medication for the target disease indication as described above where either or both are administered by inhalation or formulated for oral administration.

Although the invention finds application in humans, the invention is also useful for therapeutic veterinary purposes. The invention is useful for domestic or farm animals such as cattle, sheep, horses and poultry; for companion animals such as cats and dogs; and for zoo animals.

As used herein, a 'subject' refers to an animal, such as a mammalian or an avian species, including a human, an ape, a horse, a cow, a sheep, a goat, a dog, a cat, a guinea pig, a rat, a mouse, a chicken, etc.

CK1δ homologues are ubiquitous in nature, including in protozoa such as malaria, and in funghi and bacteria. Therefore, it is envisioned that the compounds of this invention may be used in any application requiring inhibition of CK1δ homologues. Such uses may include administration of a compound of the invention to a subject suffering from a disease, condition and/or disorder associated with infection and/or infestation with protozoa, funghi and/or bacteria.

In another aspect, the present invention provides a method of inhibiting casein kinase 1δ (CK1δ), comprising contacting a cell with an effective amount of a compound of formula (I) as defined herein, or a salt, solvate, N-oxide, tautomer, stereoisomer, polymorph and/or prodrug thereof.

Surprisingly, the compounds of the present invention or a salt, solvate, N-oxide, tautomer, stereoisomer, polymorph and/or prodrug thereof may serve as a selective inhibitor of CK1δ. The compounds of the invention in any of their disclosed forms, may selectively inhibit CK1δ compared to one or more other kinases, such as ALK5/TGFBR1, ARK5/NUAK1, casein kinase 1ε (CK1ε), p38a/MAPK14 and the like. In some embodiments, the compounds of the invention may be selective for CK1δ over at least one kinase by at least about 1, 5, 10 or 100-fold.

In another aspect the present invention provides a kit or article of manufacture including a compound of formula (I) or pharmaceutical compositions including a compound of formula (I) as described herein.

In other embodiments there is provided a kit for use in a therapeutic or prophylactic application mentioned herein, the kit including: a container holding a compound of formula (I) or pharmaceutical composition including a compound of formula (I); and a label or package insert with instructions for use.

The kit or 'article of manufacture' may comprise a container and a label or package insert on or associated with the container. Suitable containers include, for example, bottles, vials, syringes, blister pack(s), etc. The containers may be formed from a variety of materials such as glass or plastic. The container holds a compound of formula (I), or composition which is effective for treating the condition and may have a sterile access port (for example the container may be an intravenous solution bag or a vial having a stopper pierceable by a hypodermic injection needle). The label or package insert indicates that the composition is used for treating a disorder. In one embodiment, the label or package insert includes instructions for use and indicates that the therapeutic or prophylactic composition can be used to treat a disorder described herein.

The kit may comprise (a) a therapeutic or prophylactic composition; and (b) a second container with a second active principle or ingredient contained therein. The kit in this embodiment of the invention may further comprise a package insert indicating the composition and other active principle can be used to treat a disorder or prevent a complication stemming from a disorder described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the compound of formula (I) or therapeutic or prophylactic pharmaceutical composition including a compound of formula (I). In one embodiment, the device is a syringe. The therapeutic or prophylactic composition may be provided in the device in a state that is ready for use or in a state requiring mixing or addition of further components.

EXAMPLES

In Vitro Assays
Kinase Inhibition Assay
The assay used was the HotSpot assay (Reaction Biology Corp).
Compounds were tested in 10-dose $IC_{50}$ mode with a 3-fold serial dilution starting at 10 μM. Control Compound, Staurosporine, was tested in 10-dose $IC_{50}$ mode with 4-fold serial dilution starting at 20 μM. Reactions were carried out at 10 μM ATP.

Reagents
Base Reaction buffer; 20 mM Hepes (pH 7.5), 10 mM $MgCl_2$, 1 mM EGTA, 0.02% Brij35, 0.02 mg/mL BSA, 0.1 mM $Na_3VO_4$, 2 mM DTT, 1% DMSO.
*Required cofactors are added individually to each kinase reaction Reaction Procedure
1. The peptide substrate was freshly prepared in Base Reaction Buffer
2. Any required cofactors were delivered to the substrate solution above
3. The human recombinant Casein kinase 1δ was delivered into the substrate solution and gently mixed
4. The compounds in DMSO were delivered into the kinase reaction mixture by Acoustic technology (Echo550; nanoliter range), and incubated for 20 minutes at room temperature
5. $^{33}$P-ATP (specific activity 10 mCi/mL) together with ATP (10 μM) was delivered into the reaction mixture
6. The kinase reaction was incubated for 2 hours at room temperature
7. The reaction mixtures were spotted onto P81 ion exchange paper
8. The kinase activity was detected by measuring $^{33}$P-ATP-labelled product peptide using a filter-binding method.

The results of the assay (conducted on casein kinase 1δ) are given below in Table 2 ($pIC_{50}$) and Table 3 ($IC_{50}$).

TABLE 2

Inhibitory activity of a number of compounds of the present invention

| Compound | $pIC_{50}$ |
| --- | --- |
| ZH2-102 | 8.77 |
| ZH2-130 | 8.71 |
| ZH2-62 | 7.42 |
| ZH2-66 | 5.86 |
| ZH2-86 | 8.15 |
| ZH2-98 | 7.91 |
| ZH3-74 | 8.53 |
| ZH3-90 | 6.57 |
| ZH3-94 | 7.46 |
| ZH3-98 | 8.59 |
| D4476 | 6.67 |

TABLE 3

Casein kinase 1δ inhibition activity of a number of compounds of the present invention

| Compound ID | CK1δ $IC_{50}$ (M) |
| --- | --- |
| ZH2-102 | $1.70 \times 10^{-9}$ |
| ZH2-122 | $5.07 \times 10^{-9}$ |
| ZH2-130 | $1.93 \times 10^{-9}$ |
| ZH2-86 | $7.16 \times 10^{-9}$ |
| ZH2-98 | $1.26 \times 10^{-8}$ |
| ZH3-74 | $2.97 \times 10^{-9}$ |
| ZH3-94 | $3.44 \times 10^{-8}$ |
| ZH3-98 | $2.54 \times 10^{-9}$ |

Human Parenchymal Fibroblast Cell Assay
Primary human parenchymal fibroblast cells (pFbs) were cultured from parenchyma of lung resection specimens and from non-transplanted lungs of donors without chronic respiratory disease. pFbs were passaged in Dulbecco's Modified Eagle's Media (DMEM) containing 10% (v/v) heat-inactivated fetal calf serum (FCS), 15 mM HEPES, 0.2% (v/v) sodium bicarbonate, 2 mM L-glutamine, 1% (v/v) non-essential amino acids, 1% (v/v) sodium pyruvate, 2.5 µg/mL amphotericin, 5 IU/mL penicillin and 50 µg/mL streptomycin.

Prior to experimentation, pFb were incubated in serum-free DMEM containing 0.25% bovine serum albumin (BSA) and insulin-transferrin-selenium-containing supplement (Monomed A; CSL, Parkville, Melbourne, Australia). The cells were incubated with small molecular CK1δelta inhibitors (0.1-10 µM) for 30 min prior to 100 pM TGF-$β_1$ (R&D Systems, Minneapolis, MN) and the incubation continued for 16-24 hours prior to harvest of supernatant for detection of immunoreactive IL-11. Stock solutions were made as 10 mM in 100% DMSO and diluted to the required concentration in medium containing 0.1% DMSO (final concentration).

Supernatants were collected for measurement of IL-11 (R&D DuoSet, DY218) by ELISA following the manufacturers' instructions. Generally, capture antibodies were initially diluted to the recommended concentrations using PBS buffer, and then used to coat the wells of 96-well microplates (Greiner, #655061) by adding 50 µL/well and incubated overnight at room temperature. Next day, solutions were discarded and wells were washed 3 times with wash buffer (PBS containing 0.1% (v/v) Tween-20) prior to the addition of 200 µL of blocking solution (PBS containing 1% (v/v) BSA) for 1 hour to block non-specific sites. Plates were then washed 3 times with wash buffer and 50 µL of samples or standards were then added to wells and incubated for 2 hours at room temperature. After the incubation, plates were washed 3 times with wash buffer and 50 µL of detection antibodies were added to wells and incubated for 2 hours at room temperature. Plates were then washed 3 times before adding streptavidin-conjugated horseradish peroxidase (at the recommended concentrations) for 45 min. Plates were then washed 5 times with wash buffer and 100 µL TMB substrate solution (equal parts A and B, BD Biosciences) was added to each well until sufficient signals emerged. The reactions were inactivated by adding 100 µL sulphuric acid (2M $H_2SO_4$). The absorbance was measured at 450 nm using the Multiskan Ascent® plate reader. The absorbance of the cytokine standards was fitted to a logistic equation, allowing the concentrations of cytokine in samples to be determined.

Figure 2:
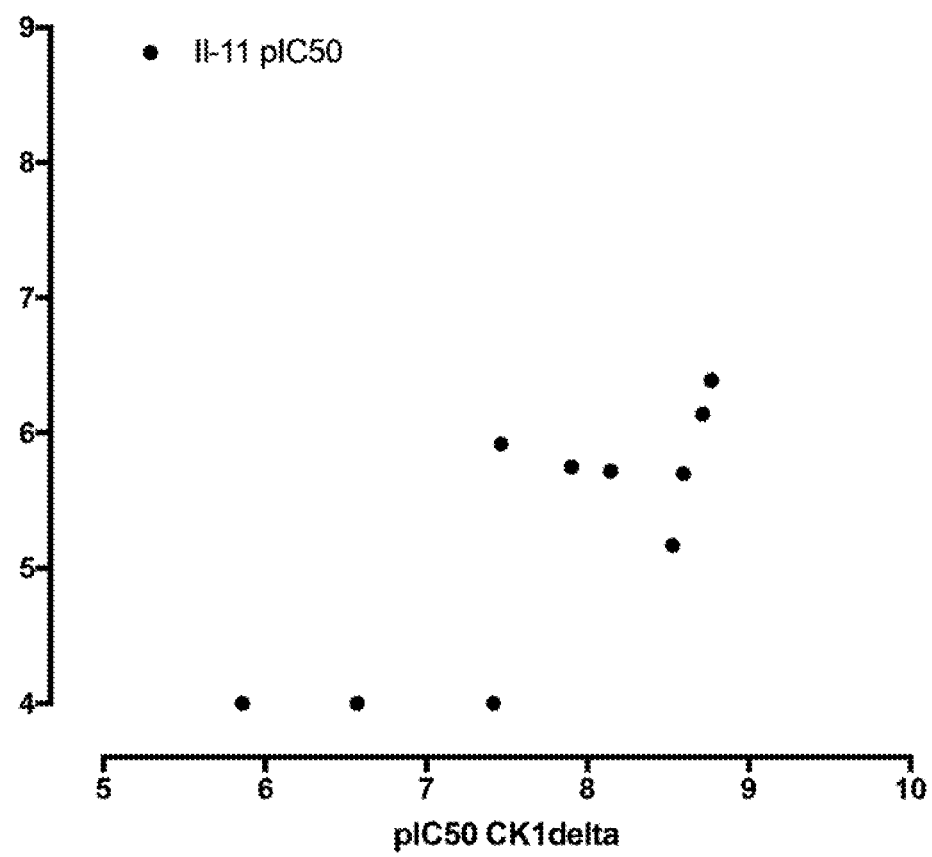
FIG. 2. $pIC_{50}$ values (the negative log of the concentration suppressing IL-11 level by 50%) for inhibition of TGF-β-induced IL-11 (interpolated from the linear regression of log concentration small molecule versus IL-11 level).

$pIC_{50}$ values (the negative log of the concentration suppressing IL-11 level by 50%) for inhibition of TGF-β-induced IL-11 were interpolated from the linear regression of log concentration small molecule versus IL-11 level (Table 4 and FIG. 2).

TABLE 4

IL-11 suppression activity of a number of compounds of the present invention

| Compound | $pIC_{50}$ IL-11 suppression* |
|---|---|
| ZH2-102 | 6.39 |
| ZH2-130 | 6.14 |
| ZH2-62 | 4.00* |
| ZH2-66 | 4.00* |
| ZH2-86 | 5.72 |
| ZH2-98 | 5.75 |
| ZH3-74 | 5.17 |
| ZH3-90 | 4.00* |
| ZH3-94 | 6.04 |
| ZH3-98 | 5.70 |

*a value of 4.00 is assigned to the pIC50 of compounds that failed to cause 50% or more inhibition at 100 mM.

Synthesis

General

Proton nuclear magnetic resonance spectra ($^1$H NMR, 400, 600 MHz) and proton decoupled carbon-13 nuclear magnetic resonance spectra ($^{13}$C NMR, 100, 150 MHz) were obtained in deuterated solvents, with residual protiated solvent as internal standard. Chemical shifts are followed by multiplicity, coupling constant(s) (J, Hz), integration and assignments where possible. Flash chromatography was carried out according to the procedure of Still et al. using an automated system.[1] Analytical thin layer chromatography (t.l.c.) was conducted on aluminium-backed 2 mm thick silica gel 60 $GF_{254}$ and chromatograms were visualized under an ultraviolet lamp. High resolution mass spectra (HRMS) were obtained by ionizing samples using electrospray ionization (ESI) and a time of flight mass analyzer. Dry THF and $CH_2Cl_2$ were obtained by the method of Pangborn et al.[2] Pet. spirits refers to petroleum ether, boiling range 40-60° C. All other commercially available reagents were used as received.

1 W. C. Still, M. Kahn and A. M. Mitra, *J. Org. Chem.*, 1978, 43, 2923.

2 A. B. Pangborn, M. A. Giardello, R. H. Grubbs, R. K. Rosen and F. J. Timmers, *Organometallics*, 1996, 15, 1518.

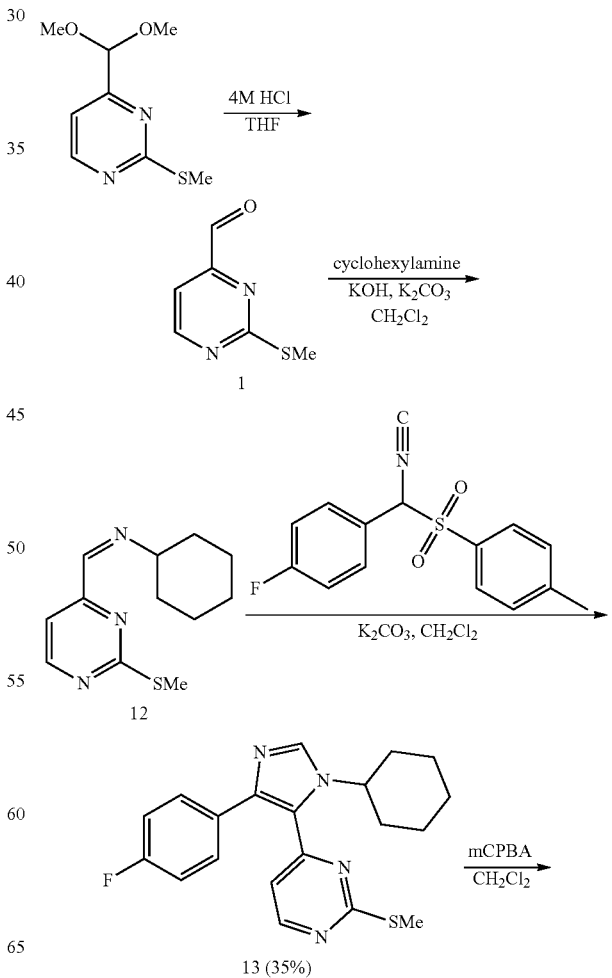

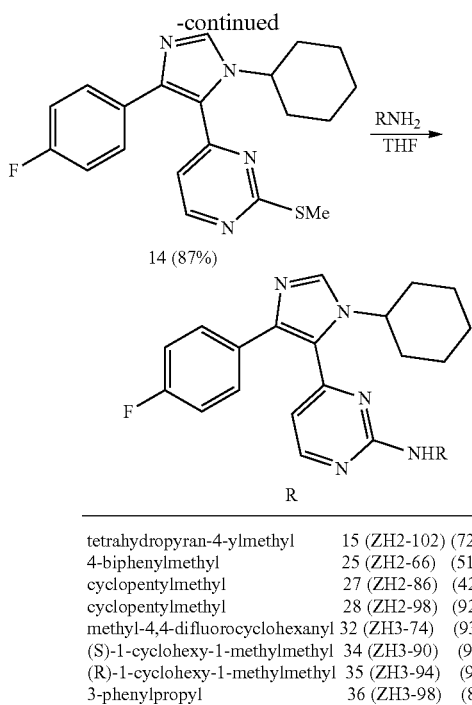

| | | |
|---|---|---|
| tetrahydropyran-4-ylmethyl | 15 (ZH2-102) | (72%) |
| 4-biphenylmethyl | 25 (ZH2-66) | (51%) |
| cyclopentylmethyl | 27 (ZH2-86) | (42%) |
| cyclopentylmethyl | 28 (ZH2-98) | (92%) |
| methyl-4,4-difluorocyclohexanyl | 32 (ZH3-74) | (93%) |
| (S)-1-cyclohexy-1-methylmethyl | 34 (ZH3-90) | (91%) |
| (R)-1-cyclohexy-1-methylmethyl | 35 (ZH3-94) | (99%) |
| 3-phenylpropyl | 36 (ZH3-98) | (88%) |

2-(Methylthio)pyrimidine-4-carbaldehyde (1)

Aqueous 4 M HCl (13 mL) was added to a solution of 4-dimethoxymethyl-2-methylsulfanyl-pyrimidine (2.42 g, 12.1 mmol). The resulting mixture was heated at 50° C. for 18 h. $^1$H NMR analysis indicated conversion to the carbaldehyde so the mixture was cooled to r.t. The reaction mixture was diluted with EtOAc and neutralized with 45% KOH solution. The aqueous phase was extracted with EtOAc, dried with MgSO$_4$ and concentrated. The crude material was used in the next step without purification (2.74 g, 87%). $^1$H NMR (CDCl$_3$, 400 MHz) δ 2.64 (3H, s), 7.44 (1H, d, J=4.8 Hz), 8.77 (1H, d, J=4.8 Hz), 9.96 (1H, s).

4-(((Cyclohexylimino)-methyl)-N-methylsulfanylpyrimidin-2-amine (12)

Aqueous K$_2$CO$_3$ 20% w/v (0.55 g, 0.39 mmol) and cyclohexylamine (2.45 mL, 21.4 mmol) were added to a solution of the crude aldehyde (2.74 g, 17.8 mmol) in CH$_2$Cl$_2$ (15 mL). The reaction mixture was stirred at r.t. overnight. $^1$H NMR analysis indicated complete consumption of the aldehyde. The reaction mixture containing the imine was used directly in the next step without isolation.

4-(1-Cyclohexyl-4-(4-fluorophenyl)-1H-imidazol-5-yl)-2-(methylsulfanyl)pyrimidine (13)

A mixture of α-(p-toluenesulfonyl)-4-fluorobenzylisonitrile (5.67 g, 19.6 mmol), 12 (2.74 g, 17.8 mmol) and K$_2$CO$_3$ (2.71 g, 19.6 mmol) in CH$_2$Cl$_2$ (15 ml) was stirred at r.t. overnight. The reaction mixture was diluted with CH$_2$Cl$_2$, and washed with water, dried (MgSO$_4$), filtered and concentrated. Flash chromatography of the residue (EtOAc/pet. spirits 1:1) afforded a solid that was recrystallized from EtOAc/pet. spirits) to give the sulfide as pale yellow crystals, (2.32 g, 35%), m.p. 192-195° C. $^1$H-NMR (400 MHz; CDCl$_3$): δ 1.41-1.19 (3H, m), 1.75-1.59 (3H, m), 1.88 (2H, d, J=13.3 Hz), 2.16 (2H, d, J=11.3 Hz), 2.58 (3H, s), 4.62 (1H, tt, J=11.9, 3.4 Hz), 6.76 (1H, d, J=5.2 Hz), 6.99 (2H, t, J=8.6 Hz), 7.40 (2H, dd, J=8.5, 5.5 Hz), 7.76 (1H, s), 8.31 (1H, d, J=5.2 Hz); $^{13}$C-NMR (101 MHz; CDCl$_3$): δ 14.2, 25.4, 26.0, 34.7, 55.9, 115.5, 115.71 (s, 1C), 117.2, 124.2, 130.3 (d, =8.0 Hz), 130.6 (d, =3.2 Hz), 136.6, 143.1, 157.1, 158.2, 162.6 (d, $J_{C-F}$=247 Hz), 173.0; HRMS (ESI$^+$) calcd for C$_{20}$H$_{22}$FN$_4$S (M+H) 369.1549. Found 369.1545.

4-(1-Cyclohexyl-4-(4-fluorophenyl)-1H-imidazol-5-yl)-2-methylsulfonylpyrimidin-2-amine (14)

mCPBA (55-86%) (0.569 g, 3.30 mmol) was added portionwise to a mixture of 13 (0.404 g, 1.10 mmol) in CH$_2$Cl$_2$ (20 mL) and the mixture was stirred at r.t. overnight. The mixture was quenched with aq. Na$_2$CO$_3$, water, brine, dried with Na$_2$SO$_4$, and concentrated in vacuum to give the sulfone as a colourless solid (0.440 g, 87%), m.p. 196-202° C. $^1$H-NMR (400 MHz; CDCl$_3$): δ 1.93-1.21 (8H, m), 2.23 (2H, d, J=11.3 Hz), 3.39 (3H, s), 4.85 (1H, tt, J=11.8, 3.4 Hz), 7.08 (2H, t, J=8.6 Hz), 7.27 (1H, m), 7.43 (2H, dd, J=8.5, 5.5 Hz), 7.86 (1H, s), 8.59 (1H, d, J=5.4 Hz); $^{13}$C-NMR (101 MHz; CDCl$_3$): δ 25.5, 25.8, 34.9, 39.2, 56.9, 116.0, 116.3, 123.1, 130.3 (d, $J_{C-F}$=3.6 Hz, 1C), 130.7 (d, $J_{C-F}$=8.2 Hz), 138.2, 146.0, 157.5, 159.8, 163.1 (d, $J_{C-F}$=249 Hz), 166.3; HRMS (ESI$^+$) calcd for C$_{20}$H$_{22}$FN$_4$O$_2$S (M+H) 401.1447. Found 401.1444.

4-(1-Cyclohexyl-4-(4-fluorophenyl)-1H-imidazol-5-yl)-N-((tetrahydro-2H-pyran-4-yl)methyl)pyrimidin-2-amine (15; ZH2-102)

4-Aminomethyltetrahydropyran (95.0 μL, 0.776 mmol) was added to a solution of 14 (31.1 mg, 0.078 mmol) in THF (5 mL) and the mixture was stirred at 40° C. for 2 d. The mixture was concentrated under vacuum and the residue purified by flash chromatography (EtOAc/pet. spirits 35% to 100%) to give a pale yellow solid (24.4 mg, 72%). $^1$H-NMR (400 MHz; CDCl$_3$): δ 1.23-1.42 (6H, m), 1.60-1.75 (5H, m), 1.89 (2H, m), 2.17 (2H, m), 3.38 (4H, m), 3.99 (2H, dd, J=3.7, 11.3 Hz), 4.54 (1H, s), 5.41 (1H, s), 6.40 (1H, d, J=5.1 Hz), 6.98 (2H, t, J=8.7 Hz), 7.44 (2H, dd, J=5.6, 8.5 Hz), 7.74 (1H, s), 8.13 (1H, d, J=3.9 Hz); $^{13}$C-NMR (101 MHz; CDCl$_3$): δ 25.4, 26.1, 31.0, 34.6, 35.3, 47.5, 55.6, 67.8, 112.0, 115.2, 115.4, 125.2, 130.0 (d, $J_{C-F}$=8.0 Hz), 130.72 (d, $J_{C-F}$=3.1 Hz), 135.8, 141.5, 158.2, 159.0, 162.4 (d, $J_{C-F}$=248 Hz), 162.7.

4-(1-Cyclohexyl-4-(4-fluorophenyl)-1H-imidazol-5-yl)-N-(pyridin-2-ylmethyl)pyrimidin-2-amine(2-picolyl) (19; ZH2-130)

2-Picolylamine (74.0 μL, 0.724 mmol) was added to a solution of 14 (29.0 mg, 0.072 mmol) in THF (5 mL) and the mixture was stirred at 40° C. for 2 d. The mixture was concentrated under vacuum and the residue purified by flash chromatography (EtOAc/pet. spirits 70% to 100%) to give a pale yellow solid (30.9 mg, 99%). $^1$H-NMR (500 MHz; CDCl$_3$): δ 1.20-1.27 (3H, m), 1.58-1.68 (3H, m), 1.83-1.85 (2H, m), 2.14-2.16 (2H, m), 4.56 (1H, tt, J=12.0, 3.6 Hz), 4.80 (2H, d, J=5.5 Hz), 6.35 (1H, m), 6.44 (1H, d, J=5.1 Hz), 6.95-7.00 (2H, m), 7.19-7.21 (1H, m), 7.32 (1H, d, J=7.8 Hz), 7.43-7.47 (2H, m), 7.66 (1H, td, J=1.8, 7.7 Hz), 7.73 (1H, s), 8.18 (1H, d, J=5.1 Hz), 8.58 (1H, dt, J=0.7, 4.9 Hz). $^{13}$C-NMR (126 MHz; CDCl$_3$): δ 25.4, 25.9, 34.7, 46.7, 55.7, 112.3, 115.3, 115.4, 121.6, 122.4, 125.2, 130.1 (d, $J_{C-F}$=8.0

Hz), 130.7 (d, $J_{C-F}$=3.2 Hz), 135.8, 136.8, 141.5, 149.4, 157.7, 158.4, 159.0, 162.4 (d, $J_{C-F}$=247 Hz), 162.5.

N-([1,1'-Biphenyl]-4-ylmethyl)-4-(1-cyclohexyl-4-(4-fluorophenyl)-1H-imidazol-5-yl)pyrimidin-2-amine (25; ZH2-66)

4-Phenylbenzylamine (30.0 mg, 0.162 mmol) was added to a solution of 14 (32.6 mg, 0.081 mmol) in THF (5 mL) and the mixture was stirred at r.t. for 6 d. The mixture was concentrated under vacuum and the residue purified by flash chromatography (EtOAc/pet. spirits 50% to 100%), followed by recrystallization from PhMe/EtOAc to give pale yellow crystals (20.9 mg, 51%). $^1$H-NMR (400 MHz; CDCl$_3$): $^1$H-NMR (400 MHz; CDCl$_3$): δ 1.12-1.26 (2H, m), 1.56-1.62 (2H, m), 1.81 (2H, m), 1.89-1.96 (2H, m), 2.13 (2H, d, J=12.0 Hz), 4.52-4.59 (1H, m), 4.77 (2H, d, J=6.0 Hz), 5.66 (1H, t, J=0.8 Hz), 6.46 (1H, d, J=5.1 Hz), 7.00 (2H, t, J=8.6 Hz), 7.35 (1H, t, J=7.2 Hz), 7.42-7.48 (6H, m), 7.59 (4H, m), 7.75 (1H, s), 8.18 (1H, d, J=4.7 Hz); $^{13}$C-NMR (101 MHz; CDCl$_3$): δ 25.4, 25.8, 34.7, 45.2, 55.6, 112.5, 115.3, 115.5, 127.2, 127.5, 127.6, 127.7, 129.0, 130.2 (d, $J_{C-F}$=7.8 Hz), 130.6 (d, $J_{C-F}$=3.3 Hz), 135.9, 138.2, 140.6, 158.4, 159.1, 162.5, 162.5 (d, $J_{C-F}$=247 Hz).

4-(1-Cyclohexyl-4-(4-fluorophenyl)-1H-imidazol-5-yl)-N-(cyclopentylmethyl)pyrimidin-2-amine (27; ZH2-86)

Cyclopentylmethyl amine (96.0 µL, 0.973 mmol) was added to a solution of 14 (39.0 mg, 0.097 mmol) in THF (5 mL) and the mixture was stirred at 40° C. for 18 h. The mixture was concentrated under vacuum and the residue purified by flash chromatography (EtOAc/pet. spirits 50% to 100%) to give a pale yellow solid (17.2 mg, 42%). $^1$H-NMR (400 MHz; CDCl$_3$): δ 1.19-1.41 (5H, m), 1.53-1.90 (11H, m), 2.16-2.25 (3H, m), 3.38 (2H, t, J=6.5 Hz), 4.57-4.59 (1H, m), 5.28-5.33 (1H, bs), 6.38 (1H, d, J=5.1 Hz), 6.98 (2H, t, J=8.7 Hz), 7.45 (2H, dd, J=5.6, 8.5 Hz), 7.74 (1H, s), 8.12 (1H, bs, J=0.6 Hz); $^{13}$C-NMR (101 MHz; CDCl$_3$): δ 25.5, 26.0, 30.6, 34.7, 39.7, 46.9, 55.6, 111.8, 115.2, 115.5, 125.3, 130.1 (d, $J_{C-F}$=8.0 Hz), 130.7 (d, $J_{C-F}$=3.0 Hz), 135.8 (d, $J_{C-F}$=8.0 Hz), 141.5, 158.1, 159.0, 162.3, 162.4 (d, $J_{C-F}$=248 Hz).

4-(1-Cyclohexyl-4-(4-fluorophenyl)-1H-imidazol-5-yl)-N-(cyclohexylmethyl)pyrimidin-2-amine (28; ZH2-98)

Cyclohexylmethylamine (92.0 µL, 0.706 mmol) was added to a solution of 14 (28.3 mg, 0.071 mmol) in THF (5 mL) and the mixture was stirred at r.t. for 2 d. The mixture was concentrated under vacuum and the residue purified by flash chromatography (EtOAc/pet. spirits 40% to 70%) to give a pale yellow solid (28.4 mg, 92%). $^1$H-NMR (400 MHz; CDCl$_3$): δ 0.93-1.03 (2H, m), 1.11-1.37 (7H, m), 1.54-1.89 (10H, m), 2.16 (2H, d, J=11.2 Hz), 3.29 (2H, t, J=6.4 Hz), 4.57 (1H, bs), 5.37 (1H, bs), 6.36 (1H, d, J=5.1 Hz), 6.97 (2H, t, J=8.7 Hz), 7.44 (2H, dd, J=5.6, 8.6 Hz), 7.72 (1H, s), 8.10 (1H, s); $^{13}$C-NMR (101 MHz; CDCl$_3$): δ 25.5, 26.0, 26.6, 31.2, 34.7, 38.0, 48.0, 55.6, 111.7, 115.2, 115.4, 125.3, 130.1 (d, $J_{C-F}$=8.0 Hz), 130.8 (d, $J_{C-F}$=3.1 Hz), 135.8, 141.5, 158.2, 159.0, 162.4 (d, $J_{C-F}$=247 Hz), 162.8.

4-(1-Cyclohexyl-4-(4-fluorophenyl)-1H-imidazol-5-yl)-N-((4,4-difluorocyclohexyl)methyl)pyrimidin-2-amine (32; ZH3-74)

4,4-Difluorocyclohexylmethanamine hydrochloride (96.0 mg, 0.519 mmol) and K$_2$CO$_3$ (72.0 mg, 0.519 mmol) was added to a solution of 14 (52.0 mg, 0.130 mmol) in THF/H$_2$O (5:1, 6 mL) and the mixture was stirred at 40° C. for 5 d. The mixture was concentrated under vacuum and the residue purified by flash chromatography (EtOAc/pet. spirits 20% to 70%) to give a pale yellow solid (56.8 mg, 93%). $^1$H-NMR (400 MHz; CDCl$_3$): δ 1.61-1.9 (10H, m), 2.12 (4H, dt, J=12.1, 20.9 Hz), 3.38 (2H, t, J=6.5 Hz), 4.51-4.56 (1H, m), 5.59 (1H, s), 6.41 (1H, d, J=5.1 Hz), 6.98 (2H, t, J=8.6 Hz), 7.44 (2H, dd, J=5.6, 8.3 Hz), 7.76 (1H, s), 8.12-8.13 (1H, m); $^{13}$C-NMR (101 MHz; CDCl$_3$): δ 25.4, 26.1, 26.9, 27.0, 33.0, 33.3 (2C), 33.5, 34.7, 36.2, 46.5, 55.7, 112.0, 115.3, 115.5, 121.2, 123.6, 125.2, 126.0, 130.1 (d, $J_{C-F}$=7.9 Hz), 130.6 (d, $J_{C-F}$=3.1 Hz), 135.9, 141.6, 158.0, 159.1, 161.4 (d, $J_{C-F}$=247 Hz), 162.6; HRMS (ESI$^+$) calcd for C$_{26}$H$_{26}$F$_2$N$_5$ [M+H]$^+$ 470.2532. Found 470.2524.

(S)-4-(1-Cyclohexyl-4-(4-fluorophenyl)-1H-imidazol-5-yl)-N-(1-cyclohexylethyl)pyrimidin-2-amine (34; ZH3-90)

(S)-Cyclohexylethylamine (61.0 µL, 0.479 mmol) was added to a solution of 14 (24.0 mg, 0.060 mmol) in THF (4 mL) and the mixture was stirred at 40° C. for 6 d. The mixture was concentrated under vacuum and the residue purified by flash chromatography (EtOAc/pet. spirits 50% to 100%) to give a pale yellow oil (24.6 mg, 91%), $[α]_D^{24}$ −9.3° (c 0.24, CH$_2$Cl$_2$). $^1$H-NMR (400 MHz; CDCl$_3$): δ 0.85-2.36 (24H, m), 3.98-4.05 (1H, m), 4.62-4.65 (1H, m), 5.99-6.00 (1H, m), 6.36 (1H, d, J=5.0 Hz), 7.02 (2H, t, J=8.5 Hz), 7.47 (2H, dd, J=5.7, 8.1 Hz), 7.84 (1H, d, J=14.5 Hz), 8.02-8.12 (1H, m); $^{13}$C-NMR (101 MHz; CDCl$_3$): δ 18.2, 25.4-26.6 (m), 29.1-29.8 (m), 34.5, 34.7, 43.4, 51.2, 55.6, 111.3, 115.3, 115.6, 125.3, 130.2 (d, $J_{C-F}$=7.9 Hz), 130.3, 135.9, 159.3, 161.9, 162.5 (d, $J_{C-F}$=248 Hz); HRMS (ESI$^+$) calcd for C$_{27}$H$_{35}$FN$_5$ [M+H]$^+$ 448.2876. Found 448.2856.

(R)-4-(1-Cyclohexyl-4-(4-fluorophenyl)-1H-imidazol-5-yl)-N-(1-cyclohexylethyl)pyrimidin-2-amine (35; ZH3-94)

(R)-Cyclohexylethyl amine (56.0 µL, 0.437 mmol) was added to a solution of 14 (21.9 mg, 0.055 mmol) in THF (4 mL) and the mixture was stirred at 40° C. for 6 d. The mixture was concentrated under vacuum and the residue purified by flash chromatography (EtOAc/pet. spirits 50% to 100%) to give a pale yellow oil (24.1 mg, 99%), $[α]_D^{24}$ +8.7 (c 0.22, CH$_2$Cl$_2$). $^1$H-NMR (400 MHz; CDCl$_3$): δ 1.01-2.17 (24H, m), 3.98 (1H, td, J=6.6, 7.7 Hz), 4.59 (1H, bs), 6.31 (1H, d, J=5.0 Hz), 6.98 (2H, t, J=8.6 Hz), 7.43 (2H, s, J=5.6, 8.1 Hz), 7.78 (1H, s), 8.04 (1H, s); $^{13}$C-NMR (101 MHz; CDCl$_3$): δ 18.2, 21.5, 25.5-26.6 (m), 29.1, 29.6, 34.5, 34.7, 43.4, 51.2, 55.6, 111.3, 115.3, 115.5, 125.3, 130.1 (d, $J_{C-F}$=8.0 Hz), 130.4 (d, $J_{C-F}$=2.8 Hz), 135.9, 159.3, 162.0, 162.4 (d, $J_{C-F}$=248 Hz); HRMS (ESI$^+$) calcd for C$_{27}$H$_{35}$FN$_5$ [M+H]$^+$ 448.2876. Found 448.2864.

4-(1-Cyclohexyl-4-(4-fluorophenyl)-1H-imidazol-5-yl)-N-(3-phenylpropyl)pyrimidin-2-amine (36; ZH3-98)

3-Phenylpropyl amine (60.0 µL, 0.439 mmol) was added to a solution of 14 (22.0 mg, 0.055 mmol) in THF (5 mL) and the mixture was stirred at 40° C. for 3 d. The mixture was concentrated under vacuum and the residue purified by flash chromatography (EtOAc/pet. spirits 50% to 70%) to give a pale yellow oil (22.1 mg, 88%). $^1$H-NMR (500 MHz; CDCl$_3$): δ 1.22-1.34 (3H, m), 1.60-1.73 (3H, m), 1.86-1.89

(2H, m), 2.01 (2H, dt, J=7.4, 15 Hz), 2.16 (2H, d, J=11 Hz), 2.76 (2H, t, J=7.7 Hz), 3.50 (2H, q, J=6.6 Hz), 4.57 (1H, s), 5.49 (1H, s), 6.41 (1H, d, J=5.0 Hz), 7.00 (2H, t, J=8.6 Hz), 7.21 (3H, t, J=7.9 Hz), 7.27-7.31 (2H, m), 7.47 (2H, dd, J=5.6, 8.2 Hz), 7.77 (1H, s), 8.14 (1H, s); $^{13}$C-NMR (126 MHz; CDCl$_3$): δ 25.7, 26.2, 31.6, 33.6, 34.9, 41.5, 55.9, 112.1, 115.6, 115.7, 125.5, 126.4, 126.4, 128.7, 128.8, 130.4 (d, $J_{C-F}$=8.0 Hz), 130.9 (d, $J_{C-F}$=2.5 Hz), 136.1, 141.8, 158.2, 159.4, 162.7, 162.7 (d, $J_{C-F}$=247 Hz).

Similar to the R$^4$=cyclohexyl compounds described above, compounds wherein R$^4$=2,2,2-trifluoroethyl may be prepared as described in the exemplary synthesis below.

1-(2-(Methylthio)pyrimidin-4-yl)-N-(2,2,2-trifluoroethyl)methanimine 2,2,2-Trifluoroethylamine hydrochloride (1.96 g, 14.5 mmol) and K$_2$CO$_3$ (3.68 g, 26.6 mmol) were added to a solution of the crude aldehyde (1.87 g, 12.1 mmol) in CH$_2$Cl$_2$ (20 mL). The reaction mixture was stirred at r.t. overnight. $^1$H NMR analysis indicated complete consumption of the aldehyde. The reaction mixture containing the imine was used directly in the next step without isolation.

4-(4-(4-Fluorophenyl)-1-(2,2,2-trifluoroethyl)-1H-imidazol-5-yl)-2-(methylthio)pyrimidine A mixture of a-(p-toluenesulfonyl)-4-fluorobenzylisonitrile (3.33 g, 11.5 mmol), 1-(2-(Methylthio)pyrimidin-4-yl)-N-(2,2,2-trifluoroethyl)methanimine (2.26 g, 9.60 mmol) and 20% aq. K$_2$CO$_3$ (8.00 mL, 11.5 mmol) in CH$_2$Cl$_2$ (50 mL) was stirred at r.t. for 5 days. The reaction mixture was diluted with CH$_2$Cl$_2$, and washed with water, dried (MgSO$_4$), filtered and concentrated. Flash chromatography of the residue (EtOAc/pet. spirits 10% to 50%) afforded a mixture of inseparable products (3.04 g crude).

4-(4-(4-Fluorophenyl)-1-(2,2,2-trifluoroethyl)-1H-imidazol-5-yl)-2-(methylsulfonyl)pyrimidine mCPBA (57-86%) (4.27 g, 24.7 mmol) was added portionwise to a mixture of the crude sulfide (3.04 g, 8.24 mmol) in CH$_2$Cl$_2$ (20 mL) and the mixture was stirred at r.t. overnight. The mixture was quenched with aq. Na$_2$CO$_3$, water, brine, dried with MgSO$_4$, and concentrated under vacuum. The residue was purified by flash chromatography (EtOAc/pet. spirits 50%) and concentrated to afford the sulfone as a yellow solid (0.438 g, 9% over 4 steps). $^1$H-NMR (400 MHz; CDCl$_3$): δ 3.37 (3H, s), 5.41 (2H, q, J=8.4 Hz), 7.13 (2H, t, J=8.5 Hz), 7.32 (1H, d, J=5.4 Hz), 7.49 (2H, dd, J=8.4, 5.4 Hz), 7.87 (1H, s), 8.65 (1H, d, J=5.4 Hz).

4-(4-(4-Fluorophenyl)-1-(2,2,2-trifluoroethyl)-1H-imidazol-5-yl)-N-(3-phenylpropyl)pyrimidin-2-amine (123; ZH4-166)

3-Phenylpropylamine (30.0 μL, 0.211 mmol) was added to a mixture of 4-(4-(4-Fluorophenyl)-1-(2,2,2-trifluoroethyl)-1H-imidazol-5-yl)-2-(methylsulfonyl)pyrimidine (21.1 mg, 0.053 mmol) in THF (5 mL) and the mixture was stirred at 40° C. for 72 h. The mixture was concentrated under vacuum and the compound purified by flash chromatography (EtOAc/pet. spirits 20% to afford a pale yellow oil (11.0 mg, 46%). $^1$H-NMR (400 MHz; CDCl$_3$): δ 2.00 (2H, m), 2.75 (2H, t, J=7.5 Hz), 3.48 (2H, q, J=6.7 Hz), 5.12 (2H, q, J=8.6 Hz), 5.24 (1H, bs), 6.41 (1H, d, J=5.1 Hz), 7.04 (2H, t, J=8.6 Hz), 7.22 (3H, d, J=6.0 Hz), 7.29 (2H, dd, J=7.4, 14.4 Hz), 7.50 (2H, dd, J=5.5, 8.5 Hz), 7.68 (1H, s), 8.13 (1H, d, J=4.6 Hz); $^{13}$C-NMR (101 MHz; CDCl$_3$): δ 31.3, 33.4, 41.2, 46.7 (q, $J_{C-F}$=35.6 Hz), 111.1, 115.5, 115.8, 124.5, 125.1, 126.2, 128.6, 130.1 (d, $J_{C-F}$=2.7 Hz), 130.5 (d, $J_{C-F}$=8.3 Hz), 140.1, 141.5, 143.3, 157.6, 158.7, 162.3, 162.8 (d, $J_{C-F}$=248 Hz). HRMS (ESI$^+$) calcd for C$_{24}$H$_{22}$F$_4$N$_5$ (M+H) 456.1811. Found 456.1808.

Other compounds described herein may be prepared by methods similar to those described above.

Also described herein are the following embodiments:
1. A compound of formula (II) or a salt, solvate, N-oxide, tautomer, stereoisomer, polymorph and/or prodrug thereof:

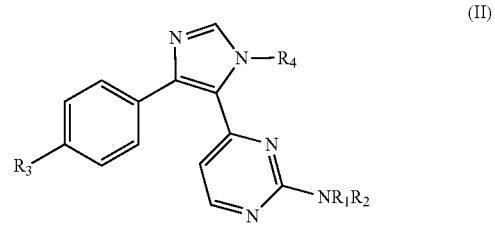

(II)

wherein:
R$^1$ and R$^2$ are each independently selected from the group consisting of H, C$_{1-3}$alkylC$_{6-12}$aryl, C$_{1-3}$alkylC$_{5-11}$heteroaryl, C$_{1-3}$alkylC$_{3-6}$cycloalkyl and C$_{1-3}$alkylC$_{3-6}$heterocyclyl;
R$^3$ is selected from the group consisting of H, F, Cl and CH$_3$;
R$^4$ is selected from the group consisting of C$_{0-3}$ alkylC$_{3-12}$ cycloalkyl and C$_{1-12}$alkyl;
wherein each of R$^1$, R$^2$, R$^3$ and R$^4$ is optionally substituted.
2. A compound according to embodiment 1, wherein the compound is not selected from the list of compounds in FIG. 8.
3. A compound according to embodiment 1, wherein R$^1$ is C$_{1-3}$ alkylC$_{6-12}$aryl.
4. A compound according to embodiment 3, wherein R$^1$ is C$_{1-2}$ alkylC$_{6-12}$aryl.
5. A compound according to embodiment 3 or embodiment 4, wherein the C$_{6-12}$aryl group is composed of two ring systems.
6. A compound according to embodiment 1, wherein R$^1$ is C$_{1-3}$alkylC$_{5-11}$heteroaryl.
7. A compound according to embodiment 6, wherein R$^1$ is C$_{1-2}$ alkylC$_{5-11}$heteroaryl.
8. A compound according to embodiment 6 or embodiment 7, wherein the C$_{5-11}$heteroaryl group is composed of two ring systems.
9. A compound according to embodiment 6 or embodiment 7, wherein a heteroatom of the C$_{5-11}$heteroaryl group is in the ortho or para position relative to the C$_{1-3}$ alkyl group.
10. A compound according to any one of embodiments 6 to 9, wherein the C$_{5-11}$heteroaryl group is a nitrogen-containing heteroaryl group.
11. A compound according to embodiment 1, wherein R$^1$ is C$_{1-3}$ alkylC$_{3-6}$cycloalkyl.
12. A compound according to embodiment 11, wherein R$^1$ is C$_{2-3}$ alkylC$_{3-6}$cycloalkyl.
13. A compound according to embodiment 11 or embodiment 12, wherein R$^1$ is substituted.

14. A compound according to embodiment 13, wherein the $C_{1-3}$alkyl group of $R^1$ is substituted.
15. A compound according to embodiment 13 or embodiment 14, wherein the substituent is a $C_{1-3}$alkyl group.
16. A compound according to embodiment 1, wherein $R^1$ is $C_{1-3}$alkyl$C_{3-6}$heterocyclyl.
17. A compound according to embodiment 16, wherein $R^1$ is $C_{1-2}$alkyl$C_{3-6}$heterocyclyl.
18. A compound according to embodiment 16 or embodiment 17, wherein the $C_{3-6}$heterocyclyl group is an oxygen-containing heterocyclyl group.
19. A compound according to any one of the preceding embodiments, wherein $R^2$ is H.
20. A compound according to any one of the preceding embodiments, wherein $R^3$ is $CH_3$.
21. A compound according to any one of embodiments 1 to 19, wherein $R^3$ is F or Cl.
22. A compound according to any one of the preceding embodiments, wherein $R^4$ is $C_{0-3}$ alkyl$C_{3-12}$cycloalkyl.
23. A compound according to embodiment 22, wherein $R^4$ is $C_1$alkyl$C_{3-12}$cycloalkyl.
24. A compound according to embodiment 22, wherein $R^4$ is $C_{3-12}$ cycloalkyl.
25. A compound according to any one of embodiments 22 to 24, wherein the $C_{3-12}$cycloalkyl group is selected from cyclopropyl, cyclobutyl, cyclopentyl, cyclohexyl and cycloheptyl.
26. A compound according to any one of embodiments 22 to 25, wherein $R^4$ is substituted.
27. A compound according to embodiment 26, wherein the $C_{3-12}$ cycloalkyl group is substituted.
28. A compound according to embodiment 26 or embodiment 27, wherein the substituent is selected from one or more $C_{1-6}$ alkyl groups, one or more halo groups, and one or more OH groups.
29. A compound according to any one of embodiments 1 to 21, wherein $R^4$ is $C_{1-12}$alkyl.
30. A compound according to embodiment 29, wherein $R^4$ is a methyl, ethyl, propyl or butyl group.
31. A compound according to embodiment 29 or embodiment 30, wherein $R^4$ is a branched alkyl group.
32. A compound according to any one of embodiments 29 to 31, wherein $R^4$ is substituted.
33. A compound according to embodiment 32, wherein the substituent is selected from one or more OH groups and/or one or more halo groups.
34. A method of treating or preventing a respiratory disease in a subject in need thereof, the method comprising administering to the subject a therapeutically effective amount of a compound of formula (II) according to any one of embodiments 1 to 33, thereby treating or preventing a respiratory disease in a subject.
35. A compound of formula (II) according to any one of embodiments 1 to 33 for use in the treatment or prevention of a respiratory disease in a subject.
36. A composition comprising a compound of formula (II) according to any one of embodiments 1 to 33, and a pharmaceutically acceptable excipient.
37. Use of a compound according to any one of embodiments 1 to 33, or a composition according to embodiment 36, in the preparation of a medicament for the treatment or prevention of a respiratory disease in a subject.

The invention claimed is:
1. A compound of formula (I) or a salt, solvate, N-oxide, tautomer, stereoisomer, polymorph and/or prodrug thereof:

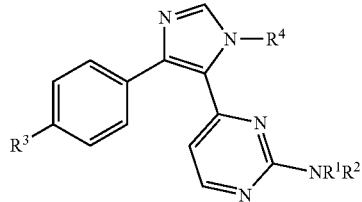

wherein:
$R^1$ is $C_{1-3}$alkyl$C_{3-6}$cycloalkyl;
$R^2$ is H;
$R^3$ is selected from the group consisting of H, F, Cl and $CH_3$;
$R^4$ is selected from the group consisting of —$C_{0-3}$alkyl$C_{3-12}$cycloalkyl and $C_{1-12}$alkyl;
wherein each of $R^1$ and $R^4$ is optionally substituted.
2. The compound according to claim 1 or a salt, solvate, N-oxide, tautomer, stereoisomer, polymorph and/or prodrug thereof, wherein $R^1$ is selected from the following groups:

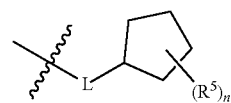

G3

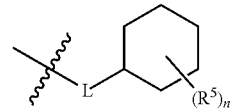

G4 wherein
each $R^5$ is selected from the group consisting of $C_{1-6}$alkyl, $C_{1-6}$haloalkyl, $C_{1-6}$ haloalkoxy, $C_{1-6}$hydroxyalkyl, $C_{3-7}$heterocyclyl, $C_{3-7}$cycloalkyl, $C_{2-6}$alkoxy, $C_{1-6}$alkylsulfanyl, $C_{1-6}$alkylsulfenyl, $C_{1-6}$alkylsulfonyl, $C_{1-6}$alkylsulfonylamino, arylsulfonoamino, alkylcarboxy, alkylcarboxyamide, oxo, hydroxy, mercapto, amino, acyl, carboxy, carbamoyl, aryl, aryloxy, heteroaryl, aminosulfonyl, aroyl, aroylamino, heteroaroyl, acyloxy, aroyloxy, heteroaroyloxy, alkoxycarbonyl, nitro, cyano, fluoro, iodo, bromo, ureido or $C_{1-6}$ perfluoroalkyl, each of which may be optionally substituted;
L is $(CR^7R^8)_m$;
$R^7$ and $R^8$ are independently selected from H and optionally substituted $C_{1-6}$alkyl;
n is selected from 0, 1, 2 and 3; and
m is selected from 1, 2 and 3.
3. The compound according to claim 2 or a salt, solvate, N-oxide, tautomer, stereoisomer, polymorph and/or prodrug thereof, wherein n is 0, 1 or 2.
4. The compound according to claim 2 or a salt, solvate, N-oxide, tautomer, stereoisomer, polymorph and/or prodrug thereof, wherein $R^1$ is G4.
5. The compound according to claim 2 or a salt, solvate, N-oxide, tautomer, stereoisomer, polymorph and/or prodrug thereof, wherein $R^1$ is G3.
6. The compound according to claim 2 or a salt, solvate, N-oxide, tautomer, stereoisomer, polymorph and/or prodrug thereof, wherein $R^4$ is selected from —$C_0$alkyl$C_{3-12}$cycloalkyl and $C_{1-12}$alkyl, wherein $R^4$ is optionally substituted with halo.

7. The compound according to claim 1 or a salt, solvate, N-oxide, tautomer, stereoisomer, polymorph and/or prodrug thereof, wherein $R^1$ is substituted $C_{1-3}$alkyl$C_{3-6}$cycloalkyl.

8. The compound according to claim 1 or a salt, solvate, N-oxide, tautomer, stereoisomer, polymorph and/or prodrug thereof, wherein $R^3$ is F.

9. The compound according to claim 1 or a salt, solvate, N-oxide, tautomer, stereoisomer, polymorph and/or prodrug thereof, wherein $R^4$ is $C_{0-3}$alkyl$C_{3-12}$cycloalkyl.

10. The compound according to claim 9 or a salt, solvate, N-oxide, tautomer, stereoisomer, polymorph and/or prodrug thereof, wherein $R^4$ is $C_{3-12}$cycloalkyl.

11. The compound of formula (I) according to claim 1 wherein the compound is selected from:

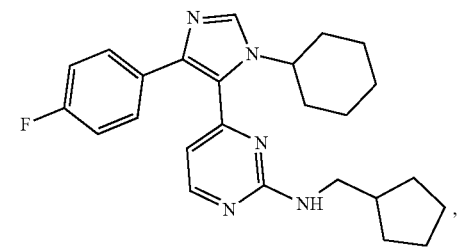,

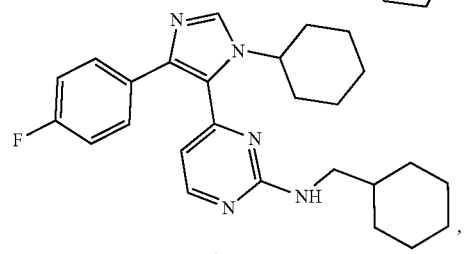,

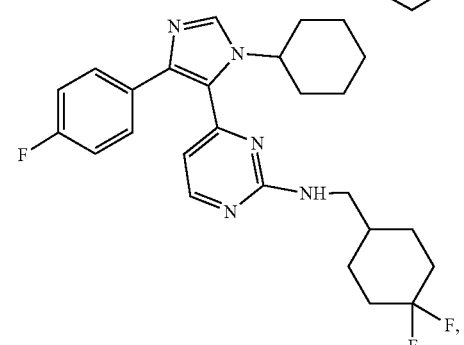,

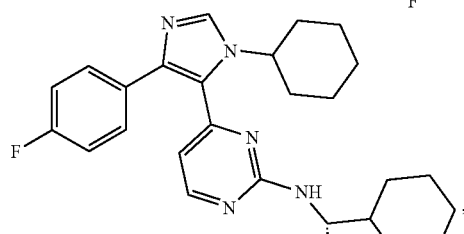,

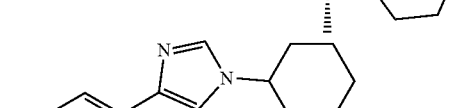,

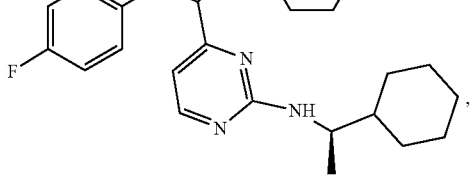,

-continued

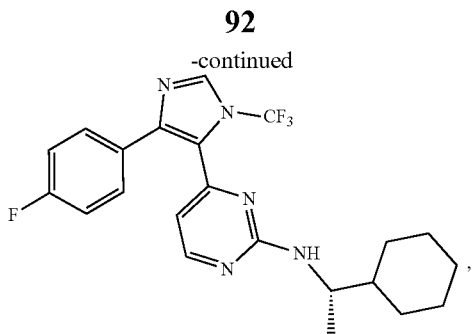,

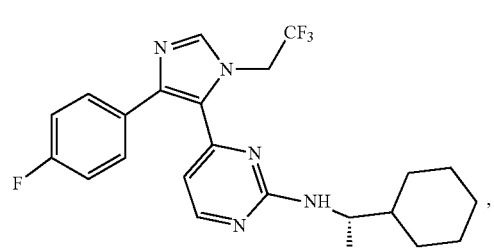,

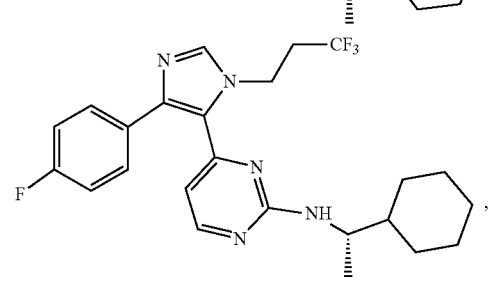,

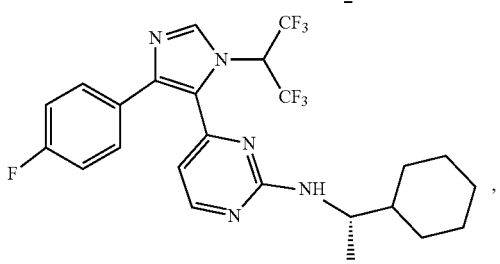,

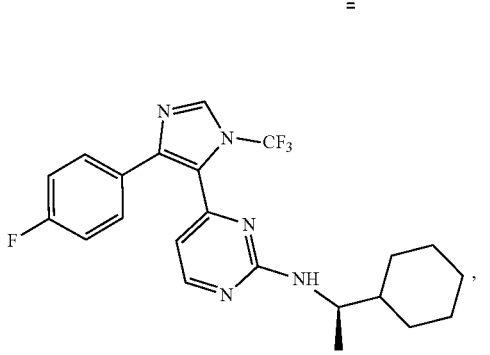,

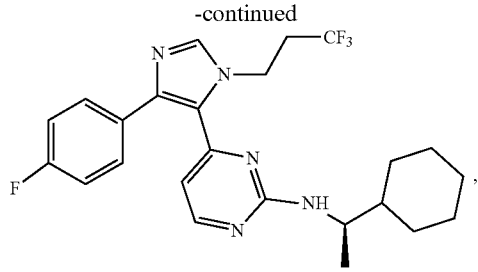
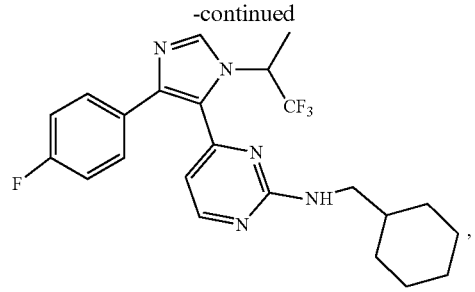
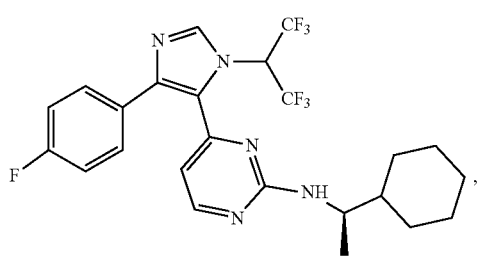
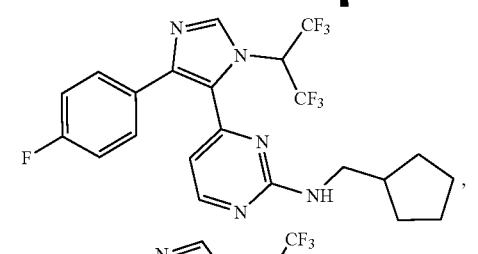
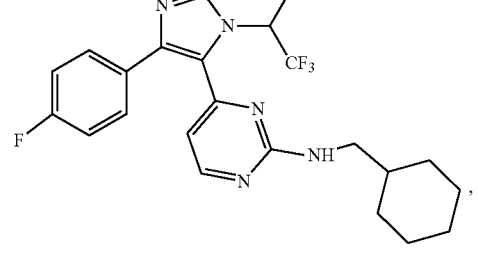
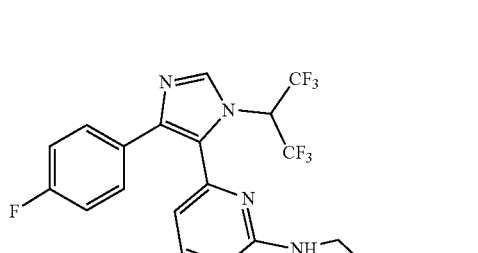
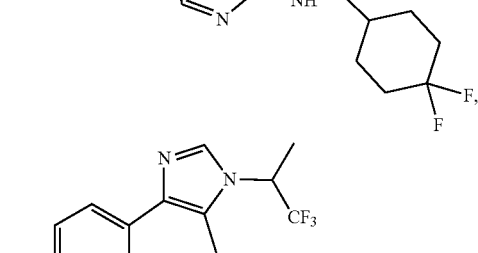
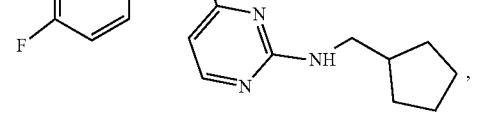
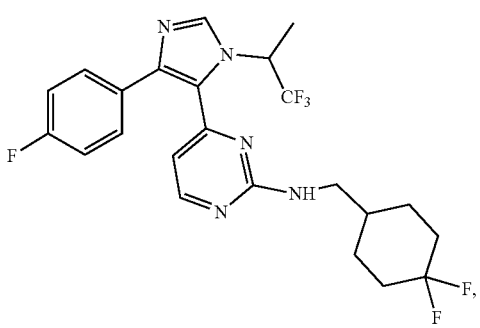
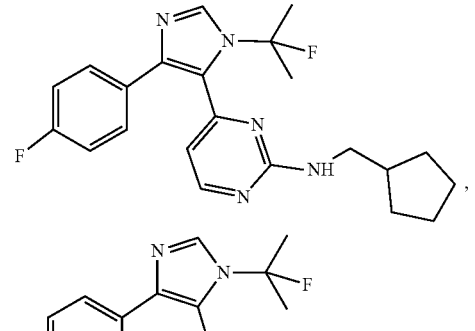
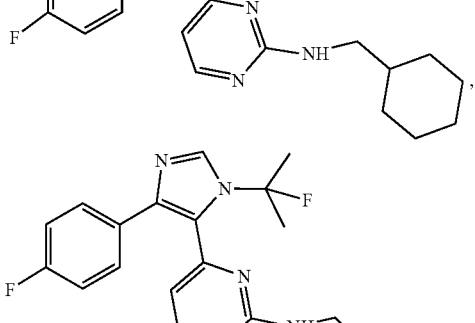
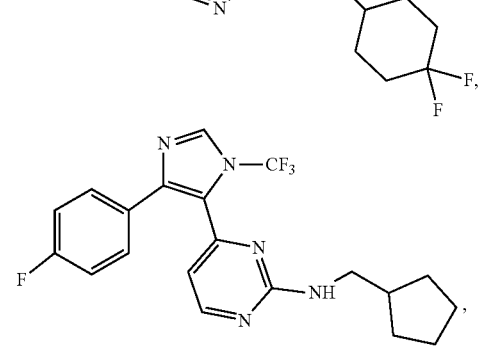

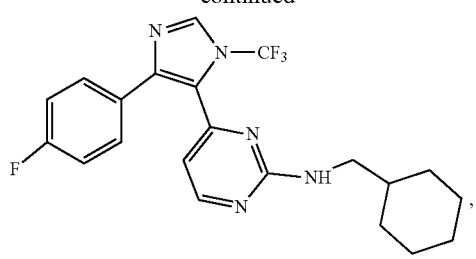
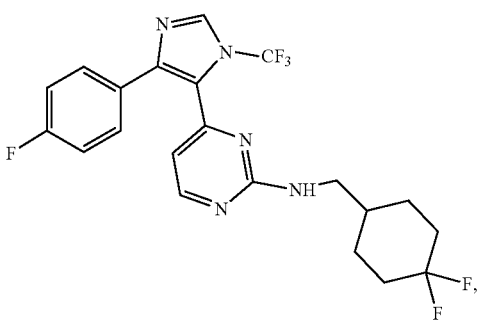
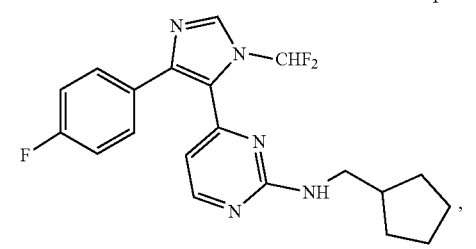
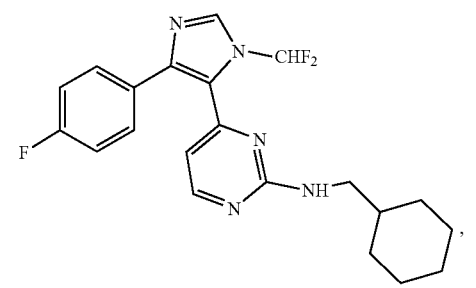
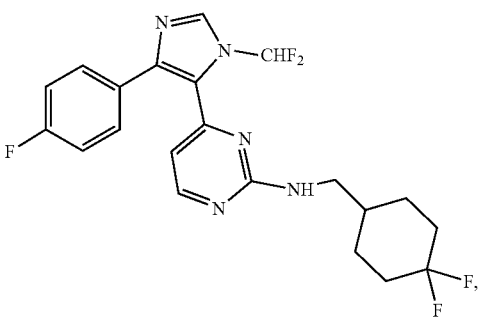
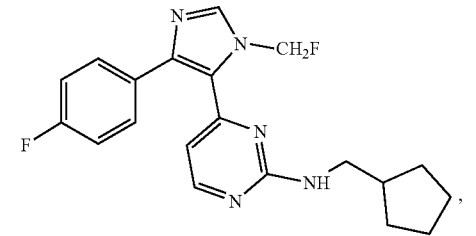
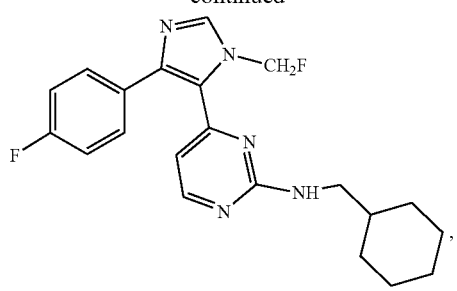
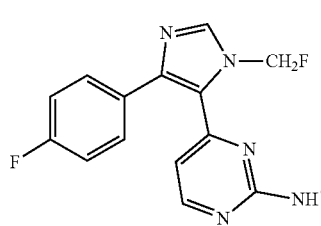
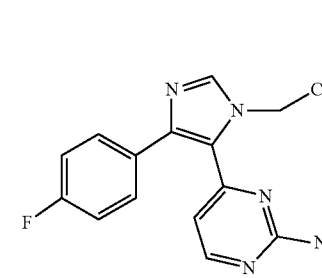
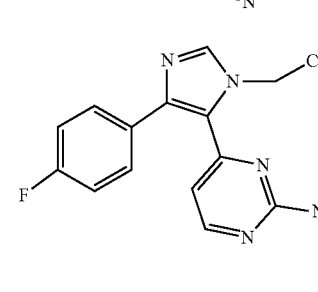
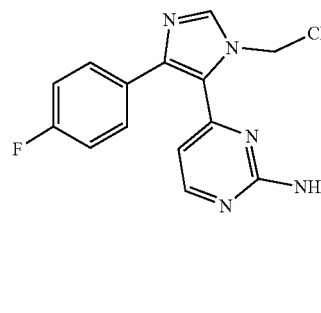
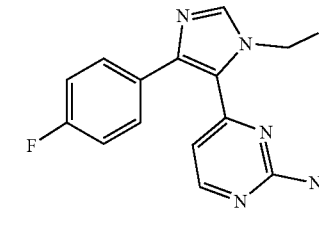

97
-continued
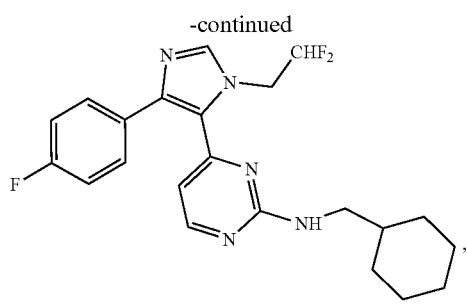
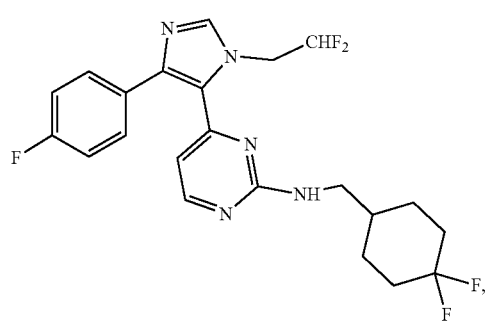
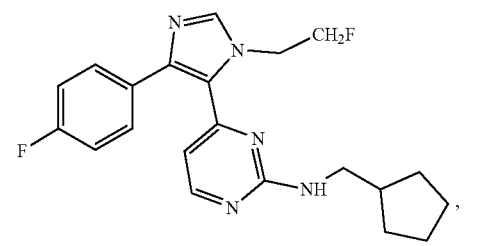
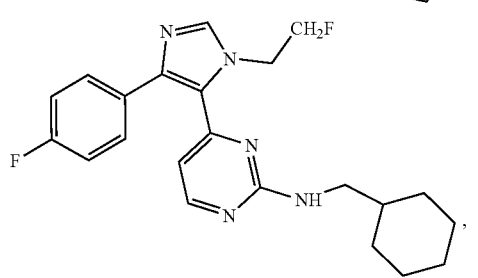
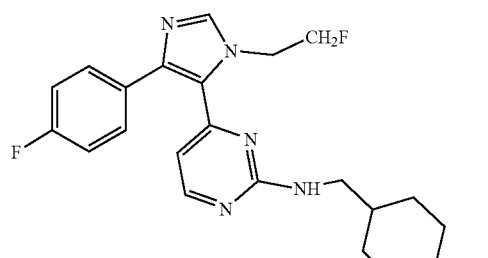
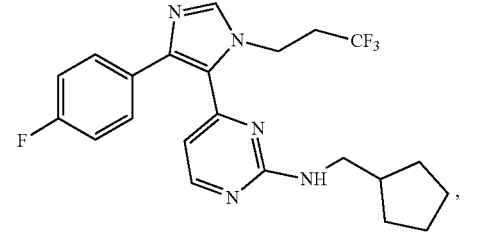
98
-continued
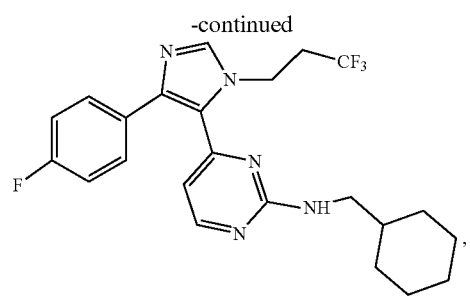
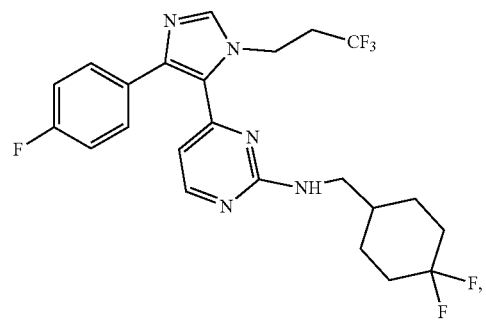
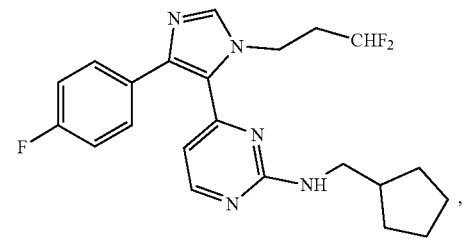
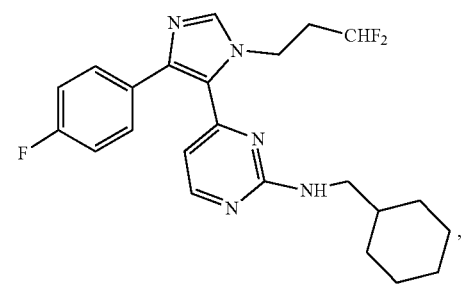
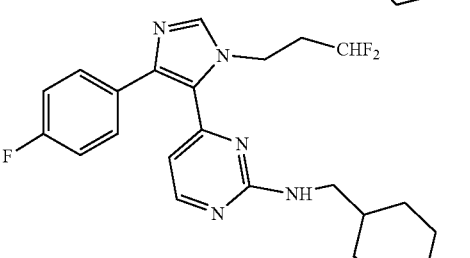
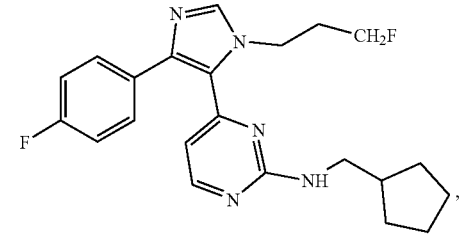

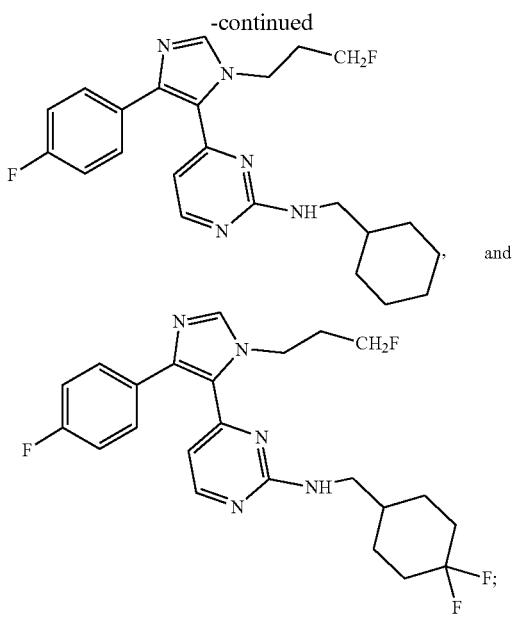

or a pharmaceutically acceptable salt, solvate, N-oxide, tautomer, stereoisomer, prodrug and/or polymorph thereof.

12. A pharmaceutical composition comprising the compound of formula (I) according to claim 1 or a pharmaceutically acceptable salt, solvate, N-oxide, tautomer, stereoisomer, prodrug and/or polymorph thereof, and a pharmaceutically acceptable excipient.

13. A method of treating or preventing a respiratory disease, the method comprising administering to a subject in need thereof a therapeutically effective amount of a compound of formula (I) as defined in claim 1 or a salt, solvate, N-oxide, tautomer, stereoisomer, polymorph and/or prodrug thereof.

14. A compound according to claim 1, or a salt, solvate, N-oxide, tautomer, stereoisomer, polymorph and/or prodrug thereof, wherein $R^4$ is optionally substituted with a substituent selected from the group consisting of $C_{1-6}$haloalkyl, $C_{1-6}$haloalkoxy, $C_{1-6}$hydroxyalkyl, $C_{3-7}$heterocyclyl, $C_{3-7}$cycloalkyl, $C_{1-6}$alkoxy, $C_{1-6}$alkylsulfanyl, $C_{1-6}$alkylsulfenyl, $C_{1-6}$alkylsulfonyl, $C_{1-6}$alkylsulfonylamino, arylsulfonoamino, alkylcarboxy, alkylcarboxyamide, oxo, hydroxy, mercapto, amino, acyl, carboxy, carbamoyl, aryl, aryloxy, heteroaryl, aminosulfonyl, aroyl, aroylamino, heteroaroyl, acyloxy, aroyloxy, heteroaroyloxy, alkoxycarbonyl, nitro, cyano, halo, ureido, $C_{1-6}$perfluoroalkyl, $C_{2-6}$alkenyl, $C_{2-6}$alkynyl, $C_{1-6}$alkoxyaryl, ester, substituted amino, disubstituted amino, acyl, ketone, substituted ketone, amide, aminoacyl, substituted amide, disubstituted amide, thiol, alkylthio, thioxo, sulfate, sulfonate, sulfinyl, substituted sulfinyl, sulfonyl, substituted sulfonyl, sulfonylamide, substituted sulfonamide, disubstituted sulfonamide, aryl$C_{1-6}$alkyl and $C_{3-7}$cycloalkyl$C_{1-6}$alkyl.

15. A compound according to claim 1, or a salt, solvate, N-oxide, tautomer, stereoisomer, polymorph and/or prodrug thereof, wherein the $C_{1-3}$alkyl of the $C_{1-3}$alkyl$C_{3-6}$cycloalkyl is straight chain.

16. A compound according to claim 15, or a salt, solvate, N-oxide, tautomer, stereoisomer, polymorph and/or prodrug thereof, wherein $R^1$ is optionally substituted with a substituent selected from the group consisting of $C_{1-6}$haloalkyl, $C_{1-6}$haloalkoxy, $C_{1-6}$hydroxyalkyl, $C_{3-7}$heterocyclyl, $C_{3-7}$cycloalkyl, $C_{1-6}$alkoxy, $C_{1-6}$alkylsulfanyl, $C_{1-6}$alkylsulfenyl, $C_{1-6}$alkylsulfonyl, $C_{1-6}$alkylsulfonylamino, arylsulfonoamino, alkylcarboxy, alkylcarboxyamide, oxo, hydroxy, mercapto, amino, acyl, carboxy, carbamoyl, aryl, aryloxy, heteroaryl, aminosulfonyl, aroyl, aroylamino, heteroaroyl, acyloxy, aroyloxy, heteroaroyloxy, alkoxycarbonyl, nitro, cyano, halo, ureido, $C_{1-6}$perfluoroalkyl, $C_{2-6}$alkenyl, $C_{2-6}$alkynyl, $C_{1-6}$alkoxyaryl, ester, substituted amino, disubstituted amino, acyl, ketone, substituted ketone, amide, aminoacyl, substituted amide, disubstituted amide, thiol, alkylthio, thioxo, sulfate, sulfonate, sulfinyl, substituted sulfinyl, sulfonyl, substituted sulfonyl, sulfonylamide, substituted sulfonamide, disubstituted sulfonamide, aryl$C_{1-6}$alkyl, heterocyclyl$C_{1-6}$alkyl, and $C_{3-7}$cycloalkyl$C_{1-6}$alkyl.

17. A compound according to claim 1, or a salt, solvate, N-oxide, tautomer, stereoisomer, polymorph and/or prodrug thereof, wherein $R^1$ is substituted $C_1$alkyl$C_{3-6}$cycloalkyl.

18. A compound according to claim 1, or a salt, solvate, N-oxide, tautomer, stereoisomer, polymorph and/or prodrug thereof, wherein $R^1$ is optionally substituted $C_1$alkyl$C_6$cycloalkyl.

19. A compound according to claim 17, or a salt, solvate, N-oxide, tautomer, stereoisomer, polymorph and/or prodrug thereof, wherein $R^1$ is substituted with one or more halo groups.

20. A compound according to claim 11, wherein the compound is:

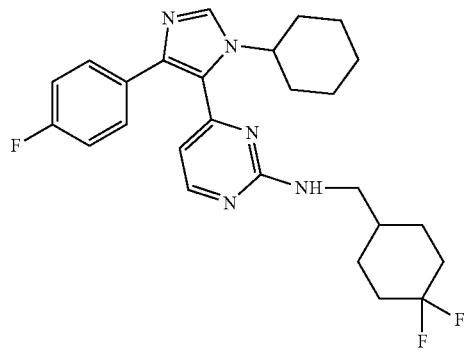 [SMILES: Fc1ccc(-c2ncn(C3CCCCC3)c2-c2ccnc(NCC3CCC(F)(F)CC3)n2)cc1]

or a salt, solvate, N-oxide, tautomer, stereoisomer, polymorph and/or prodrug thereof.

* * * * *